US008609338B2

(12) United States Patent
Mitchell et al.

(10) Patent No.: US 8,609,338 B2
(45) Date of Patent: *Dec. 17, 2013

(54) DETECTING FETAL CHROMOSOMAL ABNORMALITIES USING TANDEM SINGLE NUCLEOTIDE POLYMORPHISMS

(75) Inventors: Aoy Tomita Mitchell, Elm Grove, WI (US); Michael Mitchell, Elm Grove, WI (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 227 days.

This patent is subject to a terminal disclaimer.

(21) Appl. No.: 12/689,924

(22) Filed: Jan. 19, 2010

(65) Prior Publication Data

US 2011/0117548 A1 May 19, 2011

Related U.S. Application Data

(63) Continuation-in-part of application No. 11/713,069, filed on Feb. 28, 2007, now Pat. No. 7,799,531.

(60) Provisional application No. 60/777,865, filed on Feb. 28, 2006.

(51) Int. Cl.
*C12Q 1/68* (2006.01)
*C12P 19/34* (2006.01)

(52) U.S. Cl.
USPC .......... 435/6.11; 435/6.1; 435/6.12; 435/9.12

(58) Field of Classification Search
None
See application file for complete search history.

(56) References Cited

U.S. PATENT DOCUMENTS

| | | | |
|---|---|---|---|
| 6,258,540 B1 | 7/2001 | Lo et al. | |
| 6,979,541 B1 | 12/2005 | Pont-Kingdon et al. | |
| 7,799,531 B2 * | 9/2010 | Mitchell et al. | 435/6.12 |
| 8,399,195 B2 * | 3/2013 | Mitchell et al. | 435/6.11 |
| 2001/0048756 A1 | 12/2001 | Staub et al. | |
| 2003/0082606 A1 | 5/2003 | Lebo et al. | |
| 2003/0211522 A1 | 11/2003 | Landes et al. | |
| 2004/0137452 A1 | 7/2004 | Levett et al. | |
| 2004/0137470 A1 | 7/2004 | Dhallan | |
| 2005/0049793 A1 | 3/2005 | Paterlini-Brechot | |
| 2005/0164241 A1 | 7/2005 | Hahn et al. | |
| 2006/0121452 A1 | 6/2006 | Dhallan | |
| 2006/0160105 A1 | 7/2006 | Dhallan | |
| 2007/0207466 A1 | 9/2007 | Cantor et al. | |
| 2008/0318235 A1 | 12/2008 | Handyside | |

FOREIGN PATENT DOCUMENTS

| | | |
|---|---|---|
| WO | WO 00/34652 A1 | 6/2000 |
| WO | WO 02/068685 | 9/2002 |
| WO | WO 03/062441 | 7/2003 |
| WO | WO 2004/078999 | 9/2004 |
| WO | WO 2004/079011 | 9/2004 |
| WO | WO 2005/023091 A2 | 3/2005 |
| WO | WO 2005/035725 | 4/2005 |
| WO | WO 2005/044086 | 5/2005 |
| WO | WO 2006/011738 | 2/2006 |
| WO | WO 2011/057094 A1 | 5/2011 |

OTHER PUBLICATIONS

The Free Dictionary definition for "Aneuploidy", available via url: <medical-dictionary.thefreedictionary.com/aneuploidy>, printed Aug. 26, 2013.*
Andre, P. et al., *Fidelity and Mutational Spectrum of Pfu DNA Polymerase on a Human Mitochondrial DNA Sequence*, Genome Res., 1997. 7: p. 843-852.
Adams, K. et al., *Microchimerism an investigative Frontier in Autoimmunity and Transplantation*. JAMA. 2004, 291(9): p. 1127-1131.
Andonova, S., et al., *Introduction of the QF-PCR analysis for the purposes of prenatal diagnosis in Bulgaria—estimation of applicability of 6 STR markers on chromosomes 21 and 18*. Prenat. Diagn., 2004. 24(3): p. 202-208.
BBC News, *Safer test for unborn babies hope*. BBC News. Oct. 4, 2005. htt://news.bbc.co.uk/2/hi/health/4307628.stm.
Birch, L., et al., *Accurate and Robust Quantification of Circulating Fetal and Total DNA in Maternal Plasma from 5 to 41 Weeks of Gestation*. Clin. Chem., 2005. 51(2): p. 312-320.
Chim, S.C., et al., *Detection of the placental epigenetic signature of the maspin gene in maternal plasma*, PNAS 2005, 102(41): p. 14753-14758.
Cline, J. et al., *PCR fidlity of Pfu polymerase and other thermostable DNA polymerases*, Nucleic Acids Res. 1996, 24(18): p. 3546-3551.
Dhallan, R., et al., *A non-invasive test for prenatal diagnosis based on fetal DNA present in maternal blood: a preliminary study*. www.thelancet.com 2007. DO1:10.1016/S0140-6736(07)60115-9.
Dhallan, R. et al., *Methods to Increase the Percentage of Free Fetal DNA Recovered From the Maternal Circulation*. JAMA, 2004. 291(9): p. 1114-1119.
Ding, C. et al., *MS Analysis of single nucleotide differences in circulating nucleic acids: Application to noninvasive prenatal diagnosis*. PNAS, 2004, 101(29): p. 10762-10767.
Khrapko, K., et al., *Constant denaturant capillary electrophoresis (CDCE): a high resolution approach to mutational analysis*. Nucleic Acids Res., 1994. 22(3): p. 364-369.
Lerman, L.S. et al., *Computational simulation of DNA melting and its application to denaturing gradient gel electrophoresis*. Methods Enzymol., 1987. 155: p. 482-501.
Li, Y. et al., *Detection of Paternally Inherited Fetal Point Mutations for β-Thalessemia Using Size Fractionated Cell-Free DNA in Maternal Plasma*. JAMA., 2005. 293(7): p. 843-9. Corr: jama, 2006. 293(14): p. 1728.
Li, Y. et al., *Size Separation of Circulatory DNA in Maternal Plasma Permits Ready Detection of Fetal DNA Polymorphisms*. Clin. Chem., 2004. 50(6): p. 1002-1011.

(Continued)

*Primary Examiner* — Carla Myers
(74) *Attorney, Agent, or Firm* — Convergent Law Group LLP

(57) ABSTRACT

The invention provides tandem single nucleotide polymorphisms and methods for their use, for example, in diagnosing Down Syndrome.

8 Claims, 3 Drawing Sheets

(56) References Cited

OTHER PUBLICATIONS

Lim, E.I. et al., *Combination of Competitive Quantative PCR and Conatant Denaturant Capillary Electrophoresis for High-resolution Detection and Enumeration of Microbial Cells.* 2001. Appl. Environ. Microbiol. 67(9): p. 3897-3903.

Li-Sucholeiki, X.C. et al., *A sensitive scanning technology for low frequency nuclear point mutations in human genomic DNA.* Nucleic Acids Res., 2000. 28(9): p. E44. (8 pages).

Lo, Y.M.D. et al., *Quantitative analysis of Fetal DNA in Maternal Plasma and Serum: Implications for Noninvasive Prenatal Diagnosis.* Am J. Hum. Genet., 1998. 62(4): p. 768-775.

Lo, Y.M.D. et al., *Free Fetal DNA in Maternal Circulation.* 2004. JAMA 292(23): p. 2835-2836.

Lo, Y.M.D. et al., *Increased Fetal DNA Concentrations in the Plasma of Pregnant Women Carrying Fetuses with Trisomy 21.* Clin. Chem., 1999. 45(10): p. 1747-1751.

Malone, F.D. et al., *First-trimester sonographic screening for Down syndrome.* Obstet. Gynecol., 2003. 102(5 Pt 1): p. 1066-1079.

Parsons, B. et al., *Genotypic selection methods for the direct analysis of point mutations.* Mutation Research, 1997. 387: p. 97-121.

Pertl, B., et al., *Detection of male and female fetal DNA in maternal plasma by multiplex fluorescent polymerase chain reaction amplification of short tandem repeats.* Hum. Genet., 2000. 106: p. 45-49.

Poon, L.M. et al., *Differential DNA Methylation between Fetus and Mother as a Strategy for Detecting Fetal DNA in Maternal Plasma.* Clin. Chem., 2002. 48(1): p. 35-41.

Samura, O. et al., *Diagnosis of Trisomy 21 in Fetal Nucleated Erythrocytes from Maternal Blood by Use of Short Tandem Repeat Sequences.* Clin. Chem., 2001. 47(9): p. 1622-1626.

Simpson, J.L. et al., *Cell-Free Fetal DNA in Maternal Blood: Evolving Clinical Applications.* JAMA, 2004. 291(9): p. 1135-1137.

The International HapMap Consortium, *The International HapMap Project.* Nature, 2003. 426. p. 789-796.

The International HapMap Consortium, *A haplotype map of the human genome.* Nature, 2005. 437. p. 1299-1320.

Thompson, J.R., et al., *Heteroduplexes in mixed-template amplifications: formation consequence and elimination by 'reconditioning PCR'*, Nucleic Acids Res., 2002. 30(9): p. 2083-2088.

Thorisson, G.A., et al., *The International HapMap Project Web site.* Genome Res., 2005. 15: p. 1592-1593.

Wald, N.J., et al., *Antenatal screening for Down's syndrome with the quadruple test.* Lancet, 2003. 361(9360): p. 835-836.

Zheng, W. et al., *Origins fo human mitochondrial point mutations as DNA polymerase y-mediated errors*, Mutat. Res., 2006. 599(1-2): p. 11-20.

International Search Report for International Application No. PCT/US2007/005399 (2007).

Database SNP (Online) Retrieved from NCBI Database Accession No. rs2822654 Abstract (2004).

Antonarakis et al., *Analysis of DNA haplotypes suggests a genetic predisposition to trisomy 21 associated with DNA sequences on chromosome 21*, PNAS, 82(10), 3360-3364 (1985).

Nagy et al., *Rapid determination of trisomy 21 from amniotic fluid cells using single-nucleotide polymorphic loci*, Prenat. Diagn., 25(12). 1138-1141 (2005).

Pont-Kingdon et al., *Direct molecular haplotyping by melting curve analysis of hybridization probes: beta 2-adrenergic receptor haplotypes as an example*, Nucleic Acids Res., 33(10). e89 (2005).

Illanes et al., *Prenatal Diagnosis*, 2006. 26: 1216-1218.

Li et al., Journal of the Society for Gynecologic Investigation. 2003. 10: 503-508.

Zhong et al., Annals NY Acad Sci. 2006, 945: 250-257.

Human Chromosome 21 cSNP database, University of Geneva. Swiss Institute of Bioinformatics, HC21S00131, available via url: <csnp.unige.ch/cgi-bin/csnp_fetch?db=csnp&format=htmol&entry=HC21G00062>.

The EMBL-EBI Database. EBI Dbfetch, Accession No. F239726, Mar. 22, 2000.

Human Chromosome 21 cSNP database, University of Geneva. Swiss Institute of Bioinfomatics, HC21S00027, available via url: <csnp.unige.ch/cgi-bin/csnp_fetch?db=csnp&format=html&entry=HC21G00018>.

Howdy Database, Human Organized Whole Genome Database, Marker 5618, NM_003895, available via url: <howdy.jst.go.jp/HOWDYCL/HOWDY.pl?Cls_Marker&Key=UKEY&Val+5618>, Printed Oct. 14, 2008.

Puers, C., et al., *Identification of Repeat Sequence Heterogeneity at the Polymorphic Short Tandem Repeat Locus HUMTH01[AATG]$_n$ and Reassignment of Alleles in Population Analysis by Using a Locus-specific Allelic Ladder*, Am. J. Hum. Genet. 53:953-958, 1993.

\* cited by examiner

DETECTING FETAL CHROMOSOMAL ABNORMALITIES USING TANDEM SINGLE NUCLEOTIDE POLYMORPHISMS

CROSS REFERENCE TO RELATED APPLICATIONS

This application is a continuation-in-part of U.S. patent application Ser. No. 11/713,069, filed Feb. 28, 2007, which claims the benefit of priority of U.S. Provisional Patent Application No. 60/777,865, filed Feb. 28, 2006, each of which is hereby incorporated by reference in its entirety.

BACKGROUND

About 6.4 million women become pregnant in the U.S. each year, and about 70% of those women have maternal serum screening and/or an ultrasound test in an attempt to determine risks for common birth defects, such as those resulting from trisomy 13, 18, and 21 (Down Syndrome). Both the sensitivity and specificity of these common non-invasive screening tools are extremely poor. The best current non-invasive tests lead to a false positive rate between 7 and 20%. This high false positive rate has two catastrophic consequences for American families and society. First, it creates a large market for the two invasive diagnostic tests, chorionic villus sampling (CVS) and amniocentesis, which each carry a fetal loss rate of 0.5%-1%. These invasive tests directly result in the loss of thousands of normal fetuses annually. Second, the high false positive rate heightens maternal anxiety and stress in the large and fixed proportion of pregnant American women who receive false positive results. However, prenatal diagnosis are critical in managing a pregnancy with chromosomal abnormalities and localized genetic abnormalities, as the diagnosis can allow for interventional care during delivery and can prevent devastating consequences for the neonate. Non-invasive tests that rely on detection of short tandem repeat (STR) sequences and low complexity regions have low-sensitivity and are often riddled with false-positives and false-negatives. STR sequences and low complexity regions are highly susceptible to polymerase-induced stutters and therefore generate significant PCR-induced noise. This high background noise makes the detection and accurate quantification of low concentrations of fetal DNA in maternal plasma very unlikely, making these poor markers for use in non-invasive tests for fetal chromosomal abnormalities. Thus there is a tremendous need for the development of a sensitive and specific non-invasive test for chromosomal abnormalities, e.g., for prenatal diagnostics.

SUMMARY OF CERTAIN EMBODIMENTS OF THE INVENTION

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

BRIEF DESCRIPTION OF THE FIGURES

FIG. 3A illustrates the output that may result from a maternal buccal swab, which will comprise maternal nucleic acids but no fetal nucleic acids (upper graphs), and from a sample comprising fetal DNA but no maternal DNA, where the fetus has trisomy (lower graphs). As shown in FIG. 3A, a maternal buccal swab would be expected to show a 1:1 ratio for markers for which the maternal genome is heterozygous. The lower graphs in FIG. 3A illustrate that fetal output would show a ratio of 1:1:1 or 2:1. FIG. 3B illustrates the output that results from a sample comprising both maternal and fetal nucleic acids, where the fetus has trisomy. In this case, the output will either show two peaks of equal area and a third smaller peak or three peaks with different areas, where the areas are in a ratio of peak:x:peak+2x, where "x" represents the number of molecules of the allele inherited by the fetus from the father. FIG. 3C illustrates the output that results from a sample comprising both maternal and fetal nucleic acids, where the fetus is normal. Again, three alleles will be detected, and the peaks will be of different areas, but in this situation, the ratio of the peaks will be peak:x:peak+x.

DETAILED DESCRIPTION

Figure 1:
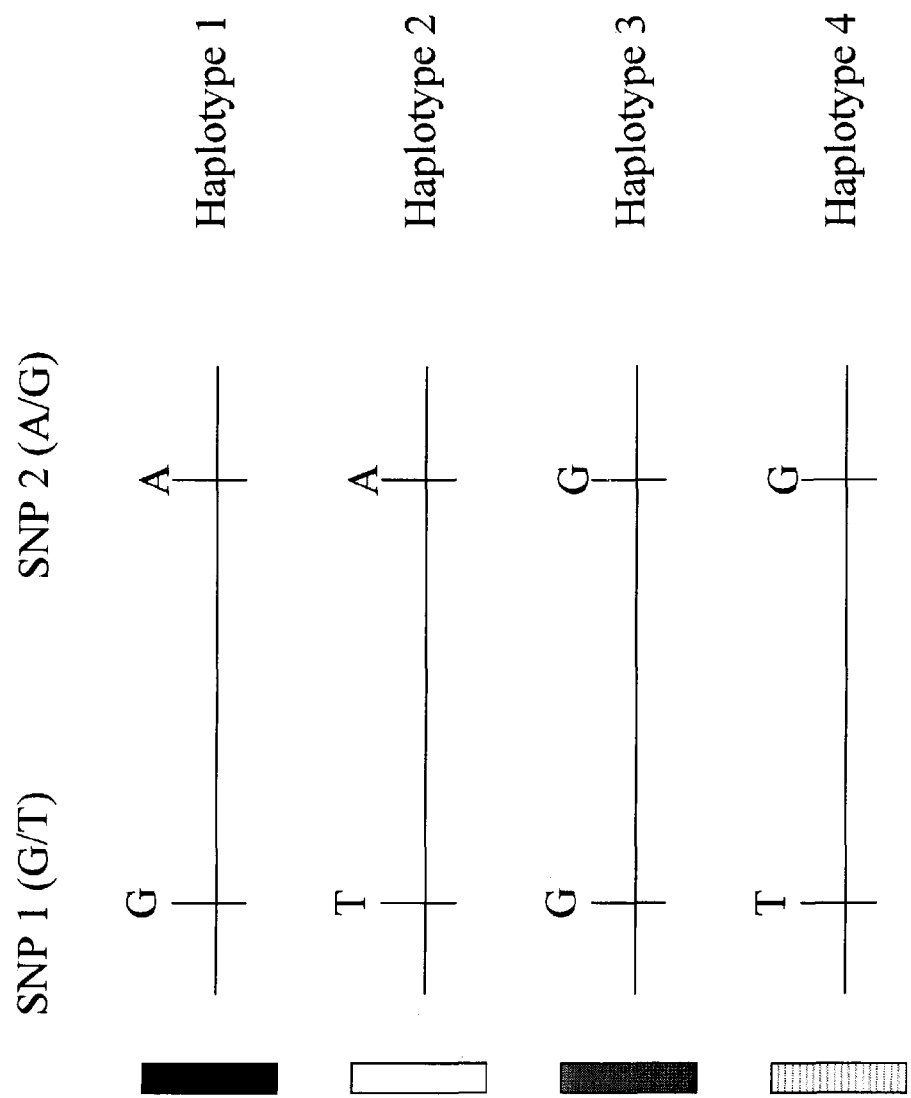
FIG. 1 depicts an example of a tandem SNP.

For years, it has been hoped that the use of fetal cells in maternal blood might be used to assess the genetic status of a developing embryo. Unfortunately, the extremely small amount of fetal cells in maternal blood (about 1 cell per ml) has proven a difficult obstacle to overcome when trying to isolate these cells for widespread clinical testing. However, cell-free fetal DNA is present in circulating maternal serum at higher percentages than fetal cells and has the potential to be assessed for chromosomal or gene defects. Cell-free fetal DNA can range from 1-47% of total DNA in maternal blood. However, a critical limitation that has yet to be successfully overcome is that maternal DNA contamination makes it difficult to differentiate fetal from maternal DNA.

As described herein, this limitation has been overcome by identifying tandem single nucleotide polymorphisms (SNPs) to detect chromosomes, e.g., to detect fetal chromosomal abnormalities. The tandem SNPs are combined with a sensitive DNA separation technology, e.g., high-fidelity PCR and constant denaturant capillary electrophoresis (CDCE), to detect fetal chromosomal abnormalities, e.g., through the simple sampling and comparison of maternal DNA to fetal DNA, e.g., from maternal serum and maternal buccal swabs. This approach substantially eliminates false positives and significantly reduces false negatives.

Accordingly, certain embodiments of the present invention provide a method for determining whether a fetus has at least one chromosomal abnormality, comprising using tandem single nucleotide polymorphisms to compare fetal DNA to maternal DNA so as to determine whether the fetus has at least one chromosomal abnormality.

In certain embodiments of the invention, fetal DNA is obtained from maternal blood. In certain embodiments of the invention, fetal DNA is cell-free fetal DNA. In certain embodiments of the invention, maternal DNA is obtained from a biological sample, e.g., maternal blood. In certain embodiments of the invention, maternal DNA is obtained from a buccal swab. In certain embodiments of the invention, maternal DNA is obtained from a biological sample that does not comprise fetal DNA.

In certain embodiments of the invention, fetal DNA is obtained from maternal blood, maternal urine, maternal sweat, maternal cells, or cell free DNA from the mother.

In certain embodiments, the biological sample is biological fluid. In certain embodiments, the biological sample is a maternal biological sample. In certain embodiments, samples may be whole blood, bone marrow, blood spots, blood serum, blood plasma, buffy coat preparations, saliva, cerebrospinal fluid, buccal swabs, solid tissues such as skin and hair, body waste products, such as feces and urine. In other embodiments, samples may be lysates, homogenates, or partially purified samples of biological materials. In other instances, biological materials can include crude or partially purified mixtures of nucleic acids. In certain embodiments, the biological sample is serum, urine, sweat, cells, or cell free DNA.

In certain embodiments of the invention, the comparison step comprises using high-fidelity PCR and constant denaturant capillary electrophoresis to compare the fetal DNA to maternal DNA. In certain embodiments of the invention, the comparison step comprises using at least about 96 tandem single nucleotide polymorphisms.

In certain embodiments of the invention, the method further comprises the step of converting the nucleic acid molecules to a homoduplex state, as opposed to being in heteroduplex form. This can be accomplished, e.g., by using an excess of primers and can aid in the tandem SNP analysis.

In certain embodiments of the invention, methods such as mutation detection technologies can be used to analyze the tandem SNPs. In certain embodiments of the invention, methods such as denaturing HPLC, denaturing capillary electrophoresis, cycling temperature capillary electrophoresis, allele-specific PCRs, quantitative real time PCR approaches such as TaqMan® PCR system, polony PCR approaches, and microarray approaches can be used to analyze the tandem SNPs.

In certain embodiments of the invention, the single nucleotide polymorphisms in each tandem single nucleotide polymorphism are each at most about 250 basepairs apart. In certain embodiments of the invention, the single nucleotide polymorphisms in each tandem single nucleotide polymorphism are each at most about 200 basepairs apart. In certain embodiments of the invention, the single nucleotide polymorphisms in each tandem single nucleotide polymorphism are each at most about 150 basepairs apart. In certain embodiments of the invention, the single nucleotide polymorphisms in each tandem single nucleotide polymorphism are each at most about 100 basepairs apart. In certain embodiments of the invention, the single nucleotide polymorphisms in each tandem single nucleotide polymorphism are each at most about 50 basepairs apart.

In certain embodiments of the invention, at least one tandem single nucleotide polymorphism is located on the p arm of chromosome 21. In certain embodiments of the invention, at least one tandem single nucleotide polymorphism is located on the q arm of chromosome 21.

In certain embodiments of the invention, the chromosomal abnormality is chromosomal aneuploidy. In certain embodiments of the invention, the chromosomal abnormality is trisomy 13, 18 or 21. In certain embodiments of the invention, the chromosomal abnormality is trisomy 21.

In certain embodiments of the invention, the chromosomal abnormality is an insertion mutation (e.g., a large insertion (≥3 megabasepair) or small insertion (<3 megabasepair). In certain embodiments of the invention, the chromosomal abnormality is a deletion mutation (e.g., a large deletion (≥3 megabasepair) or small deletion (<3 megabasepair)). The deleted region could include a deleted gene.

In certain embodiments of the invention, the methods can be used to detect copy number polymorphisms and/or copy number variants in the genome. In certain embodiments of the invention, the methods can be used to detect chromosome 22q11 deletion syndrome, which is associated with cardiac defects.

Chromosomal abnormalities include deletions associated with genetic syndromes and disorders such as the 22q11 deletion syndrome on chromosome 22, which is associated with cardiac defects. Other examples of chromosomal abnormalities include the 11q deletion syndrome on chromosome 11 and 8p deletion syndrome on chromosome 8, both of which are also associated with cardiac defects.

In certain embodiments of the invention, the fetus is a male fetus. In certain embodiments of the invention, the fetus is a female fetus. In certain embodiments of the invention, the fetus is a mammal. In certain embodiments of the invention, the fetus is a human. In certain embodiments of the invention, the fetus is a non-human mammal. In certain embodiments of the invention, the fetus has been determined to be at an elevated risk for having a chromosomal abnormality.

In certain embodiments of the invention, the method further comprises using tandem single nucleotide polymorphisms to compare paternal DNA to the fetal and/or maternal DNA.

In certain embodiments of the invention, the fetal DNA is subjected to an enrichment step. In certain embodiments of the invention, the fetal DNA is not subjected to an enrichment step.

Certain embodiments of the present invention provide a method for identifying chromosomes, comprising comparing tandem single nucleotide polymorphisms on the chromosomes so as to identify the chromosomes. Thus, the methods of the present invention are not limited to maternal-fetal analysis, but can also be applied to other situations, e.g., forensic analysis of blood samples.

In certain embodiments of the invention, the methods further comprises, prior to the comparison step, determining a set of tandem single nucleotide polymorphisms for a specific chromosome.

Certain embodiments of the present invention provide a system comprising packaging material and primers that specifically hybridize to each of the single nucleotide polymorphisms of at least one of the tandem single nucleotide polymorphisms identified herein.

Certain embodiments of the present invention provide a system comprising packaging material and primers that specifically hybridize flanking sequences of at least one of the tandem single nucleotide polymorphisms of the invention.

Certain embodiments of the present invention provide a system comprising packaging material and at least one oligonucleotide that specifically hybridizes to at least one of the tandem single nucleotide polymorphisms of the invention.

Certain embodiments of the present invention provide the use of high-fidelity PCR (HiFi-PCR) to amplify SNPs or tandem SNPs for the purpose of, e.g., determining chromosomal abnormalities.

Certain embodiments of the present invention provide the use of HiFi-PCR to amplify nucleic acids, e.g., DNA, isolated, e.g., from a maternal biological sample to analyze fetal DNA for chromosomal abnormalities.

In certain embodiments, HiFi-PCR is used to detect aneuploidy and large (≥3 megabasepairs) or small (<3 megabasepairs) deletions and/or insertions.

In certain embodiments, the maternal biological sample is serum, urine, sweat, cells, or cell free DNA.

Certain embodiments of the present invention provide an isolated nucleic acid sequence comprising at least one of SEQ ID NOs 1-357.

Certain embodiments of the present invention provide an isolated nucleic acid sequence of the invention (e.g., a nucleic acid sequence comprising a tandem SNP or a primer; e.g., at least one of SEQ ID NOs 1-357) for use in medical treatment or diagnosis.

In certain embodiments, the nucleic acid sequences may be, e.g., isolated nucleic acid sequences and may be, e.g., about 1000 or fewer, e.g., about 900 or fewer, e.g., about 800 or fewer, e.g., about 700 or fewer, e.g., about 600 or fewer, e.g., about 500 or fewer, e.g., about 400 or fewer, e.g., about 300 or fewer, e.g., about 250 or fewer, e.g., about 200 or fewer, e.g., about 150 or fewer, e.g., about 100 or fewer, or e.g., about 50 or fewer nucleic acids in length.

Thus, short haplotypes are used to detect fetal chromosomal abnormalities in maternal serum, e.g., for the most common of these defects, trisomy 21. To demonstrate this method, tandem SNPs for chromosome 21 are identified, heterozygosity of the tandem SNPs determined, the ability to detect fetal DNA from maternal serum demonstrated, and the ability to detect fetal chromosomal abnormalities in maternal serum demonstrated. 118 tandem SNPs have already been identified. These tandem SNPs are useful in the diagnosis of chromosomal abnormalities, for example, of trisomy 21. Thus, certain embodiments of the invention provide the specific tandem SNPs, or combinations thereof, as well as their use in diagnostic and therapeutic applications.

The output of these experiments, e.g., assays based on a set of tandem SNPs for chromosome 21, can be used in the clinic as an alternative to invasive diagnostic tests like amniocentesis and CVS, using, e.g., CDCE or other techniques capable of detecting the tandem SNPs. These diagnostics are sensitive and specific. The tandem SNP assay is particularly suited for fetal DNA analysis because fetal DNA present in maternal serum is generally present as short fragments (e.g., an average of 300 basepairs or fewer).

Thus, certain embodiments of the present invention are directed to each of these tandem SNPs individually, and certain embodiments are directed to combinations of any and/or all of the tandem SNPs. Certain embodiments of the invention are directed to methods of using the tandem SNPs for diagnosing chromosomal abnormalities. Certain embodiments of the invention are directed to compilations of the tandem SNPs (e.g., reference tables) that are useful for diagnosing chromosomal abnormalities. Certain embodiments of the invention are also directed to primers for each of these tandem SNPs individually, and certain embodiments are directed to combinations of primers for any and/or all of the tandem SNPs. Certain embodiments of the invention provide isolated nucleic acid sequences that comprise at least one of the tandem SNPs and compositions that comprise the isolated nucleic acid sequences.

Prenatal Screening

An increasing number of fetal medical conditions can be successfully managed during the neonatal period if an early diagnosis is made. A variety of prenatal screening tools are available for chromosomal and birth defects. The two most commonly utilized non-invasive tools are ultrasound and measurements of maternal serum markers. Both of these "tests" have inadequate sensitivity and specificity for screening the most common of the defects, Down Syndrome (trisomy 21).

An ultrasound screening called the nuchal translucency test is becoming more common. However, this test has an overall sensitivity of 77% for trisomy 21 with a false positive rate of 6% (Malone et al., Obstet Gynecol, 2003. 102(5 Pt 1): p. 1066-79). The most advanced serum marker test is the "quad" screen, which measures the levels of alpha-fetoprotein (AFP), human chorionic gonadotropin (hCG), unconjugated estriol (E3), and inhibin-A. The biological reason for these markers to be elevated or reduced in a percentage of mothers carrying children with trisomy 21 is not understood. Further, the test is only capable of assigning risk categories (i.e., 1 in 250, 1 in 100, 1 in 10), and not in making specific diagnoses. The quad screen is associated with a false positive rate of 7% and a sensitivity of less than 80%, rates which do not approach those achieved by invasive prenatal diagnostic tests (Wald et al., Lancet, 2003. 361(9360): p. 835-6).

Because of the inadequate sensitivity and specificity of currently available non-invasive tools, amniocentesis and chorionic villus sampling (CVS), both invasive procedures, remain the standard for the definitive detection of fetal chromosomal abnormalities. Both of these procedures carry a 0.5%-1% fetal loss rate, which translate into the death of thousands of normal fetuses annually. To solve this problem and meet the overwhelming need for an accurate non-invasive test, several strategies have been previously proposed by other investigators. However, those studies have been limited by their ability to detect and differentiate fetal DNA from maternal DNA.

A PCR-based approach for detecting aneuploidy relies on a method called quantitative fluorescent polymerase chain reaction (QF-PCR) of short tandem repeats (STRs). However, polymerase errors are frequently made in the repeat sequences, generating a high background "noise" for each STR assay. These PCR errors (stutters) make peak area measurements difficult and thus the detection and quantification of low frequency fetal DNA in maternal serum not possible (Dhallan et al., JAMA, 2004. 291(9): p. 1114-9).

In 1994, a technology called constant denaturant capillary electrophoresis (CDCE) combined with high-fidelity PCR (HiFi-PCR) was developed to allow researchers to detect and quantify low frequency somatic mutations present in heterogeneous cell populations (Khrapko et al., Nucleic Acids Res, 1994. 22(3): p. 364-9). Compared to other DNA separation methods, CDCE permits the highest resolution separation of DNA sequences differing by even a single base pair. The separation is based on differences in the melting temperature and the resulting electrophoretic mobility differences as the DNA molecules migrate through a linear polyacrylamide matrix under partially denaturing conditions (Khrapko et al., 1994). CDCE coupled with HiFi-PCR has been demonstrated to detect mutations in ~100 bp sequences with a sensitivity of at least $2 \times 10^{-6}$ in human cells and tissues (Li-Sucholeiki et al., Nucleic Acids Res, 2000. 28(9): p. E44). As described herein, this technology can be applied to single nucleotide polymorphisms (SNPs), natural single basepair variations present in the genome, to separate alleles. CDCE is used in the present invention to screen tandem SNPs to increase the informativeness (or heterozygosity) of each CDCE assay by increasing the number of possible alleles (or haplotypes) available. Through the use of tandem SNPs, a highly specific and sensitive assay for detecting fetal chromosomal abnormalities by simply comparing maternal serum to maternal buccal swabs has been created.

High-Fidelity PCR is an amplification method resulting in an error rate (in per basepair doubling) equal to or better than standard PCR. For example, Taq polymerase has an error rate of $~10^{-4}$ per basepair doubling. As an example, Pyrococcus furiosus (Pfu) is a high-fidelity polymerase. The published error rate for Pfu is $1.3 \times 10^{-6}$ per basepair doubling (Cline et al, Nucleic Acids Res. 1996 Sep. 15; 24(18): 3546-3551).

Methods for improving PCR fidelity include, among others: A) using a high-fidelity polymerase enzyme; and B) the addition of chemical reagents (e.g., betaine) that can lower temperatures required during the PCR process. The prolonged heating of DNA and nucleotides during PCR can lead to damaged products, such as deaminated cytosines (uracils) and thus lead to misincorporation errors and miscopying errors during PCR (Andre, Kim, Khrapko, Thilly. Genome Res. 1997 7: 843-852. Zheng, Khrapko, Coller, Thilly, Copeland. Mutat Res. 2006 Jul. 25; 599(1-2):11-20). Examples of high-fidelity enzymes include Pfu and its derivations, or other enzymes with similar proofreading 3'→5' exonucleases.

In certain embodiments of the invention, amplification, e.g., HiFi-PCR, is performed with primers being in molar excess (e.g., $10^{12}$ copies/µl of primer vs $10^6$ or less of the template) so that it is more likely that primers will anneal with template DNA than with each other (see, e.g., Li-Sucholeiki X C, Thilly W G. Nucleic Acids Res. 2000 May 1; 28(9):E44; Thompson J R, Marcelino L, Polz M. Nucleic Acids Res. 2002 May 1; 30(9): 2083-2088.). This can significantly reduce the creation of heteroduplexes.

A "single nucleotide polymorphism (SNP)" is a single basepair variation in a nucleic acid sequence. A "tandem SNP" is a pair of SNPs that are located in a nucleic acid sequence, e.g. on a chromosome, in a manner that allows for the detection of both of the SNPs. The distance between SNPs generally is about 250 basepairs or fewer, e.g., about 200 basepairs or fewer, e.g., about 150 basepairs or fewer, e.g., about 100 basepairs or fewer, e.g., about 50 basepairs or fewer. The tandem SNPs can be detected by a variety of means that are capable of detecting the tandem SNPs. In one embodiment of the invention, constant denaturant capillary electrophoresis (CDCE) can be combined with high-fidelity PCR (HiFi-PCR) to detect the tandem SNP. In another embodiment, hybridization on a microarray is used. In another embodiment, high-fidelity PCR is used and another method capable of detecting SNPs present at low frequencies is used (e.g., denaturing HPLC, denaturing capillary electrophoresis, cycling temperature capillary electrophoresis, allele-specific PCRs, quantitative real time PCR approaches such as TaqMan® PCR system, polony sequencing approaches, microarray approaches, and mass spectrometry). In another embodiment, high-throughput sequencing approaches, e.g., at a single molecule level, are used.

The term "nucleic acid" refers to deoxyribonucleotides or ribonucleotides and polymers thereof in either single- or double-stranded form, made of monomers (nucleotides) containing a sugar, phosphate and a base that is either a purine or pyrimidine. Unless specifically limited, the term encompasses nucleic acids containing known analogs of natural nucleotides that have similar binding properties as the reference nucleic acid and are metabolized in a manner similar to naturally occurring nucleotides. Unless otherwise indicated, a particular nucleic acid sequence also encompasses conservatively modified variants thereof (e.g., degenerate codon substitutions) and complementary sequences, as well as the sequence explicitly indicated. Specifically, degenerate codon substitutions may be achieved by generating sequences in which the third position of one or more selected (or all) codons is substituted with mixed-base and/or deoxyinosine residues.

The term "nucleotide sequence" refers to a polymer of DNA or RNA which can be single-stranded or double-stranded, optionally containing synthetic, non-natural or altered nucleotide bases capable of incorporation into DNA or RNA polymers. The terms "nucleic acid," "nucleic acid molecule," or "polynucleotide" are used interchangeably.

Certain embodiments of the invention encompass isolated or substantially purified nucleic acid compositions. In the context of the present invention, an "isolated" or "purified" DNA molecule or RNA molecule is a DNA molecule or RNA molecule that exists apart from its native environment and is therefore not a product of nature. An isolated DNA molecule or RNA molecule may exist in a purified form or may exist in a non-native environment such as, for example, a transgenic host cell. For example, an "isolated" or "purified" nucleic acid molecule is substantially free of other cellular material or culture medium when produced by recombinant techniques, or substantially free of chemical precursors or other chemicals when chemically synthesized. In one embodiment, an "isolated" nucleic acid is free of sequences that naturally flank the nucleic acid (i.e., sequences located at the 5' and 3' ends of the nucleic acid) in the genomic DNA of the organism from which the nucleic acid is derived.

The following terms are used to describe the sequence relationships between two or more nucleic acids or polynucleotides: (a) "reference sequence," (b) "comparison window," (c) "sequence identity," (d) "percentage of sequence identity," and (e) "substantial identity."

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well-known in the art. Thus, the determination of percent identity between any two sequences can be accomplished using a mathematical algorithm. Non-limiting examples of such mathematical algorithms are the algorithm of Myers and Miller (Myers and Miller, CABIOS, 4, 11 (1988)); the local homology algorithm of Smith et al. (Smith et al., Adv. Appl. Math., 2, 482 (1981)); the homology alignment algorithm of Needleman and Wunsch (Needleman and Wunsch, JMB, 48, 443 (1970)); the search-for-similarity-method of Pearson and Lipman (Pearson and Lipman, Proc. Natl. Acad. Sci. USA, 85, 2444 (1988)); the algorithm of Karlin and Altschul (Karlin and Altschul, Proc. Natl. Acad. Sci. USA, 87, 2264 (1990)), modified as in Karlin and Altschul (Karlin and Altschul, Proc. Natl. Acad. Sci. USA 90, 5873 (1993)).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters. The CLUSTAL program is well described by Higgins et al. (Higgins et al., CABIOS, 5, 151 (1989)); Corpet et al.

(Corpet et al., Nucl. Acids Res., 16, 10881 (1988)); Huang et al. (Huang et al., CABIOS, 8, 155 (1992)); and Pearson et al. (Pearson et al., Meth. Mol. Biol., 24, 307 (1994)). The ALIGN program is based on the algorithm of Myers and Miller, supra. The BLAST programs of Altschul et al. (Altschul et al., JMB, 215, 403 (1990)) are based on the algorithm of Karlin and Altschul supra.

Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold. These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when the cumulative alignment score falls off by the quantity X from its maximum achieved value, the cumulative score goes to zero or below due to the accumulation of one or more negative-scoring residue alignments, or the end of either sequence is reached.

In addition to calculating percent sequence identity, the BLAST algorithm also performs a statistical analysis of the similarity between two sequences. One measure of similarity provided by the BLAST algorithm is the smallest sum probability (P(N)), which provides an indication of the probability by which a match between two nucleotide or amino acid sequences would occur by chance. For example, a test nucleic acid sequence is considered similar to a reference sequence if the smallest sum probability in a comparison of the test nucleic acid sequence to the reference nucleic acid sequence is less than about 0.1, less than about 0.01, or even less than about 0.001.

To obtain gapped alignments for comparison purposes, Gapped BLAST (in BLAST 2.0) can be utilized. Alternatively, PSI-BLAST (in BLAST 2.0) can be used to perform an iterated search that detects distant relationships between molecules. When utilizing BLAST, Gapped BLAST, PSI-BLAST, the default parameters of the respective programs (e.g., BLASTN for nucleotide sequences, BLASTX for proteins) can be used. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix. Alignment may also be performed manually by inspection.

For purposes of the present invention, comparison of nucleotide sequences for determination of percent sequence identity to the promoter sequences disclosed herein may be made using the BlastN program (version 1.4.7 or later) with its default parameters or any equivalent program. By "equivalent program" is intended any sequence comparison program that, for any two sequences in question, generates an alignment having identical nucleotide or amino acid residue matches and an identical percent sequence identity when compared to the corresponding alignment generated by the program.

(c) As used herein, "sequence identity" or "identity" in the context of two nucleic acid or polypeptide sequences makes reference to a specified percentage of residues in the two sequences that are the same when aligned for maximum correspondence over a specified comparison window, as measured by sequence comparison algorithms or by visual inspection. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity." Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even at least 95%, 96%, 97%, 98%, or 99% sequence identity, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 70%, 80%, 90%, or even at least 95%.

Another indication that nucleotide sequences are substantially identical is if two molecules hybridize to each other under stringent conditions. Generally, stringent conditions are selected to be about 5° C. lower than the thermal melting point ($T_m$) for the specific sequence at a defined ionic strength and pH. However, stringent conditions encompass temperatures in the range of about 1° C. to about 20° C., depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

(e)(ii) The term "substantial identity" in the context of a peptide indicates that a peptide comprises a sequence with at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, or 94%, or even 95%, 96%, 97%, 98% or 99%, sequence identity to the reference sequence over a specified comparison window. In certain embodiments, optimal alignment is conducted using the homology alignment algorithm of Needleman and Wunsch (Needleman and Wunsch, JMB, 48, 443 (1970)). An indication that two peptide sequences are substantially identical is that one peptide is immunologically reactive with antibodies raised against the second peptide. Thus, a peptide is substantially identical to a second peptide, for example, where the two peptides differ only by a conservative substitution. Thus, certain embodiments of the invention provide nucleic acid molecules that are substantially identical to the nucleic acid molecules described herein.

For sequence comparison, typically one sequence acts as a reference sequence to which test sequences are compared. When using a sequence comparison algorithm, test and reference sequences are input into a computer, subsequence coordinates are designated if necessary, and sequence algorithm program parameters are designated. The sequence comparison algorithm then calculates the percent sequence identity for the test sequence(s) relative to the reference sequence, based on the designated program parameters.

As noted above, another indication that two nucleic acid sequences are substantially identical is that the two molecules hybridize to each other under stringent conditions. The phrase "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. The thermal melting point (Tm) is the temperature (under defined ionic strength and pH) at which 50% of the target sequence hybridizes to a perfectly matched probe. Specificity is typically the function of post-hybridization washes, the critical factors being the ionic strength and temperature of the final wash solution. For DNA-DNA hybrids, the $T_m$ can be approximated from the equation of Meinkoth and Wahl (1984); $T_m$ 81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is reduced by about 1° C. for each 1% of mismatching; thus, $T_m$, hybridization, and/or wash conditions can be adjusted to hybridize to sequences of the desired identity. For example, if sequences with >90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14, 15, or 20° C. lower than the $T_m$. Using the equation, hybridization and wash compositions, and desired temperature, those of ordinary skill will understand that variations in the stringency of hybridization and/or wash solutions are inherently described. If the desired degree of mismatching results in a temperature of less than 45° C. (aqueous solution) or 32° C. (formamide solution), the SSC concentration is increased so that a higher temperature can be used. Generally, highly stringent hybridization and wash conditions are selected to be about 5° C. lower than the $T_m$ for the specific sequence at a defined ionic strength and pH.

An example of highly stringent wash conditions is 0.15 M NaCl at 72° C. for about 15 minutes. An example of stringent wash conditions is a 0.2×SSC wash at 65° C. for 15 minutes. Often, a high stringency wash is preceded by a low stringency wash to remove background probe signal. An example medium stringency wash for a duplex of, e.g., more than 100 nucleotides, is 1×SSC at 45° C. for 15 minutes. For short nucleotide sequences (e.g., about 10 to 50 nucleotides), stringent conditions typically involve salt concentrations of less than about 1.5 M, less than about 0.01 to 1.0 M, Na ion concentration (or other salts) at pH 7.0 to 8.3, and the temperature is typically at least about 30° C. and at least about 60° C. for long probes (e.g., >50 nucleotides). Stringent conditions may also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

Very stringent conditions are selected to be equal to the $T_m$ for a particular probe. An example of stringent conditions for hybridization of complementary nucleic acids that have more than 100 complementary residues on a filter in a Southern or Northern blot is 50% formamide, e.g., hybridization in 50% formamide, 1 M NaCl, 1% SDS at 37° C., and a wash in 0.1×SSC at 60 to 65° C. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C.

In addition to the chemical optimization of stringency conditions, analytical models and algorithms can be applied to hybridization data-sets (e.g. microarray data) to improve stringency.

The term "treatment" or "treating," to the extent it relates to a disease or condition includes preventing the disease or condition from occurring, inhibiting the disease or condition, eliminating the disease or condition, and/or relieving one or more symptoms of the disease or condition.

The invention will now be illustrated by the following non-limiting Examples.

Example 1

Tandem SNPs for Chromosome 21

96 allelic markers on chromosome 21 are selected by examining tandem SNPs. These tandem SNPs will cover both q and p arms of the chromosome. Using heterozygosity data available through dbSNP, DCC Genotype Database and through the HapMap Project, SNPs that appear to be promising for high heterozygosity (≥25%) are selected. Because all four possibilities may not exist in nature due to haplotype blocks in regions of low recombination, those that suggest less than three haplotypes are screened out. FIG. 1 depicts an example of tandem SNPs (SNP 1=rs2839416, average estimated heterozygosity 0.444 and SNP2=rs2839417, average estimated heterozygosity 0.414).

Target sequences covering tandem SNPs are designed using Vector NTI and WinMelt software. As an example, the melting map of a CDCE target covering two tandem SNPs (dbSNP rs2839416 and rs2839417) on chromosome 21 was calculated using WinMelt according to the algorithm of Lerman and Silverstein (Lerman et al., Methods Enzymol, 1987. 155: p. 482-501) and is depicted in FIG. 2.

Figure 2:
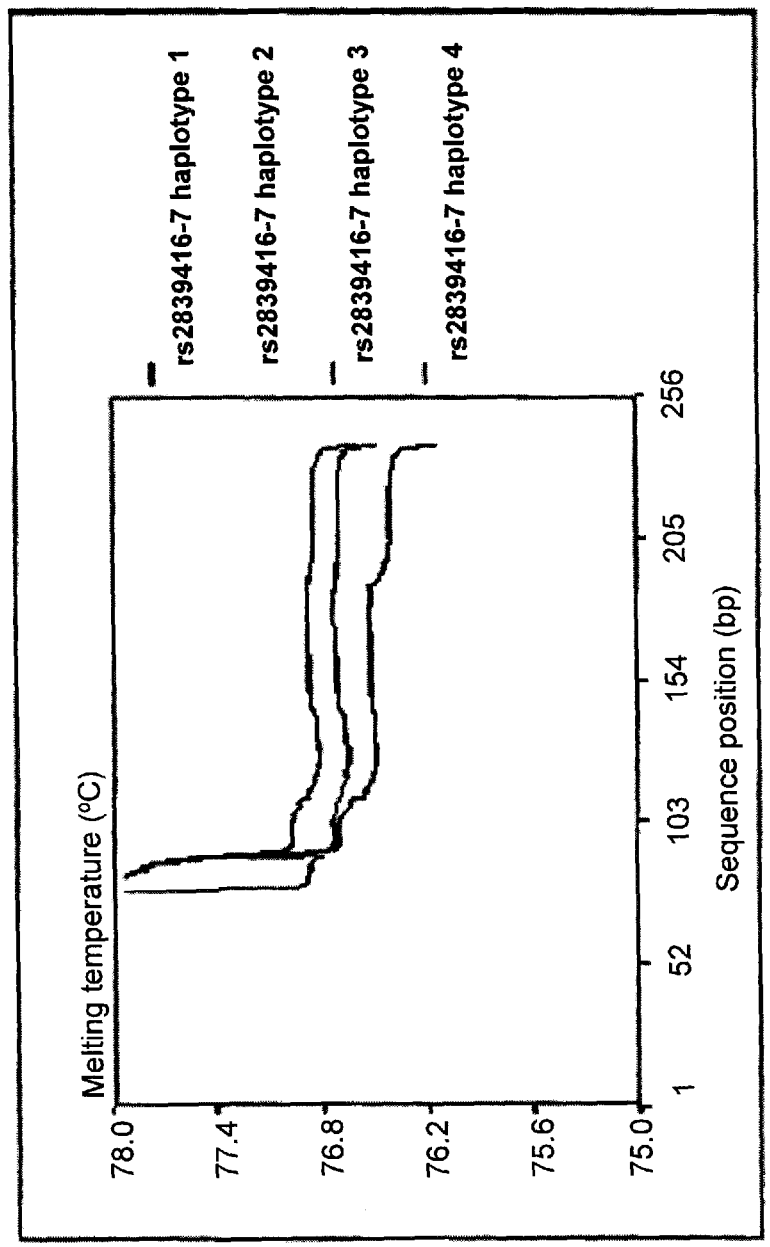
FIG. 2 depicts a DNA melting map of a constant denaturant capillary electrophoresis target sequence covering a tandem SNP.

FIG. 2 depicts a DNA melting map of a CDCE target sequence covering tandem SNPs. All four haplotypes can be theoretically separated according to DNA melting temperature. The black line indicates haplotype 1 (G,A). The yellow line indicates haplotype 2 (T,A). The red line indicates haplotype 3 (G,G). The green line indicates haplotype 4 (T,G).

HiFi PCR optimization for each target sequence is performed using Pfu polymerase. One of primers flanking the target sequence is ~20 bases in length and labeled 5' with a fluorescein molecule. The other primer is about 74 bases including a ~20-base target specific sequence and the 54-base clamp sequence. A standard HiFi PCR condition is applied to all target sequences, varying only annealing temperatures. These PCR amplicons are subjected to CDCE electrophoretic separation. The resulting electropherogram are analyzed for yield and purity of the PCR products. The purity is evaluated by comparing the peak area of the desired products to that of the byproducts and nonspecific amplification. Target sequences that can be amplified with a high PCR efficiency (≥45% per cycle) and low levels of byproducts and nonspecific amplification (≥0.1% of the desired products) are immediately be subjected to CDCE optimization. For those target sequences that do not have acceptable PCR products in the first stage, increasing amounts of $Mg^{+2}$ concentrations (up to about 7 mM) in combination with different annealing temperatures are tested. For the remaining target sequences that still do not work, primer positions are changed and the entire optimization process is repeated.

For CDCE optimization, the relevant haplotypes are created for the targets. The optimal separation condition for each haplotype should provide the greatest resolution among the observed peaks. Initial optimization is done around the theoretical melting temperature ($T_m$) in a 2° C. temperature range in increments of 0.2° C. which covers ($T_m-1$° C.±a predetermined offset) to ($T_m+1$° C.±a predetermined offset).

Electropherogram and peak measurements are transferred to a spreadsheet for analysis. To ensure the quality of the data, minimum and maximum peak heights are used. Individual markers are failed if electrophoretic spikes occur. Peak areas are used to calculate allele ratios. A check for allelic preferential amplification is performed on all 96 tandem SNPs.

Results

In the fall of 2005, the International HapMap Project publicly released genotypes and frequencies from 270 people of four ethnic populations. Chromosome 21 haplotype data from approximately 40,000 SNPs genotyped across four populations, including U.S. residents with northern and western European ancestry, residents of Ibadan, Nigeria, of Tokyo, Japan, and of Beijing, China, were downloaded (2005-10-24: HapMap Public Release #19) and converted to the +orientation. Tandem SNP candidates fell within 100 basepairs from each other and at least three haplotypes existed in all four ethnic populations. CDCE target sequences and primers are designed for the tandem SNPs identified through the HapMap Project. The neighboring sequences for each of the tandem SNPs are imported into a software program, e.g., Sequencher (Gene Codes, Ann Arbor, Mich.) and/or Vector NTI (Invitrogen, Carlsbad, Calif.) for sequence alignment and primer design, and into Winmelt (Medprobe, Oslo, Norway) or Poland software (available on the world wide web at biophys.uniduesseldorf.de/local/POLAND/poland.html) where the algorithm for computing DNA melting temperatures given the Gotoh-Tagashira values for the enthalpy of melting DNA sequences are used to calculate melting temperatures of target sequences. CDCE candidates generally have a high melting region adjacent to a low melting region, lie in a low melting region, melting temperatures of the low melting region fall below 80° C., and no "valleys" occur between the high melting region and the low melting region.

All of the 40,000 genotypes on chromosome 21 have been analyzed for tandem SNP/CDCE marker suitability. 118 tandem SNPs/CDCE targets meeting our requirements have been identified (see Table 1 for the first 42 identified and Table 2 for all 118).

Primer sequences for these 118 tandem SNP/CDCE targets have been designed. These will be optimized as described herein using HiFi PCR and CDCE. These optimizations are described herein and include the creation of relevant haplotypes for all targets, a check for allelic preferential amplification during HiFi PCR, and obtaining the greatest resolution among peaks during CDCE. Haplotypes may be separated as homoduplex peaks. However, if certain targets cannot be separated out as homoduplexes, maternal DNA can be separated from fetal DNA as heteroduplexes.

TABLE 1

| Tandem SNP #/Observed haplotypes | dbSNP Name | Chromosome | Chromosome Position | bp dif |
|---|---|---|---|---|
| 1 | rs10482852 | A/C Chr21 | 14613855 | 86 |
| CC/CT/AC | rs2822567 | C/T Chr21 | 14613941 | |
| 2 | rs2822654 | A/C Chr21 | 14687773 | 13 |
| AA/AG/CG/CA | rs1882882 | A/G Chr21 | 14687786 | |
| 3 | rs2822785 | A/G Chr21 | 14876399 | 65 |
| AG/GG/AA/GA | rs2822786 | A/G Chr21 | 14876464 | |
| 4 | rs2822786 | A/G Chr21 | 14876464 | 67 |
| GC/AC/GT | rs2822787 | C/T Chr21 | 14876531 | |
| 5 | rs2822816 | A/G Chr21 | 14948471 | 97 |
| AA/GT/GA | rs2822817 | A/T Chr21 | 14948568 | |

TABLE 1-continued

| Tandem SNP #/Observed haplotypes | dbSNP Name | Chromosome | Chromosome Position | bp dif |
|---|---|---|---|---|
| 6<br>CA/CG/TG | rs2822878<br>rs2822879 | C/T Chr21<br>A/G Chr21 | 15033311<br>15033401 | 90 |
| 7<br>AT/GT/AC | rs2223163<br>rs2822963 | A/G Chr21<br>C/T Chr21 | 15149849<br>15149921 | 72 |
| 8<br>GG/AG/GT/AT | rs1297213<br>rs1297214 | A/G Chr21<br>G/T Chr21 | 15253641<br>15253724 | 83 |
| 9<br>CT/CC/TT | rs2142450<br>rs10482863 | C/T Chr21<br>C/T Chr21 | 15257273<br>15257340 | 67 |
| 10<br>TC/CC/TT | rs10482863<br>rs1041403 | C/T Chr21<br>C/T Chr21 | 15257340<br>15257386 | 46 |
| 11<br>TA/CA/TG | rs2823333<br>rs2823334 | C/T Chr21<br>A/G Chr21 | 15825896<br>15825985 | 89 |
| 12<br>GG/AC/GC | rs2823335<br>rs992557 | A/G Chr21<br>C/G Chr21 | 15826379<br>15826457 | 78 |
| 13<br>AA/GG/AG | rs2823348<br>rs2823349 | A/G Chr21<br>A/G Chr21 | 15833575<br>15833601 | 26 |
| 14<br>AT/AC/CT/CC | rs2823502<br>rs2823503 | A/C Chr21<br>C/T Chr21 | 16124651<br>16124683 | 32 |
| 15<br>CC/CA/TC/TA | rs960391<br>rs13049140 | C/T Chr21<br>A/C Chr21 | 17034864<br>17034893 | 29 |
| 16<br>CA/TA/TG | rs2824078<br>rs10482886 | C/T Chr21<br>A/G Chr21 | 17134418<br>17134448 | 30 |
| 17<br>CT/CC/TC | rs1999288<br>rs208897 | C/T Chr21<br>C/T Chr21 | 17696177<br>17696269 | 92 |
| 18<br>GG/GA/AA/AG | rs2824310<br>rs6517774 | A/G Chr21<br>A/G Chr21 | 17744045<br>17744144 | 99 |
| 19<br>GG/AA/AG/GA | rs728015<br>rs728014 | A/G Chr21<br>A/G Chr21 | 17968624<br>17968657 | 33 |
| 20<br>GG/CG/CC/GC | rs1047978<br>rs2824495 | C/G Chr21<br>C/G Chr21 | 18091026<br>18091089 | 63 |
| 21<br>GT/GC/AT/AC | rs157058<br>rs150141 | A/G Chr21<br>C/T Chr21 | 18355312<br>18355365 | 53 |
| 22<br>GG/GT/AG/AT | rs2824733<br>rs2824734 | A/G Chr21<br>G/T Chr21 | 18610953<br>18611032 | 79 |
| 23<br>AA/GT/GA/AT | rs963638<br>rs963639 | A/G Chr21<br>A/T Chr21 | 19009158<br>19009214 | 56 |
| 24<br>AC/TA/TC/AA | rs2187166<br>rs2156203 | A/T Chr21<br>A/C Chr21 | 19081111<br>19081210 | 99 |
| 25<br>CT/TC/CC/TT | rs2825470<br>rs2825471 | C/T Chr21<br>C/T Chr21 | 19567109<br>19567169 | 60 |
| 26<br>TT/GC/GT | rs2407581<br>rs2825926 | G/T Chr21<br>C/T Chr21 | 20272611<br>20272639 | 28 |
| 27<br>GT/AT/GC/AC | rs377685<br>rs420778 | A/G Chr21<br>C/T Chr21 | 20272988<br>20273021 | 33 |
| 28<br>AG/CT/CG | rs2826058<br>rs2826059 | A/C Chr21<br>G/T Chr21 | 20464969<br>20465061 | 92 |
| 29<br>CT/CC/TT | rs2826072<br>rs2826073 | C/T Chr21<br>C/T Chr21 | 20487958<br>20488053 | 95 |
| 30<br>CC/TC/TT | rs2032203<br>rs2826152 | C/T Chr21<br>C/T Chr21 | 20598845<br>20598943 | 98 |

TABLE 1-continued

| Tandem SNP #/Observed haplotypes | dbSNP Name | Chromosome | Chromosome Position | bp dif |
|---|---|---|---|---|
| 31 CA/TA/CG/TG | rs1735808 rs1786400 | C/T Chr21 A/G Chr21 | 20766284 20766329 | 45 |
| 32 TG/CA/CG/GA | rs2014509 rs2014519 | C/T Chr21 A/G Chr21 | 21113081 21113160 | 79 |
| 33 GA/AA/GG | rs2155798 rs2155799 | A/G Chr21 A/G Chr21 | 21471022 21471097 | 75 |
| 34 GA/GG/CA | rs1475881 rs7275487 | C/G Chr21 A/G Chr21 | 21748820 21748916 | 96 |
| 35 CG/GG/GC/CC | rs2522558 rs12627388 | C/G Chr21 C/G Chr21 | 21916691 21916714 | 23 |
| 36 GC/GT/CC/CT | rs12627388 rs2522559 | C/G Chr21 C/T Chr21 | 21916714 21916762 | 48 |
| 37 AC/GC/GT | rs1735934 rs2826958 | A/G Chr21 C/T Chr21 | 21995555 21995633 | 78 |
| 38 AC/GT/AT/GC | rs994676 rs2826982 | A/G Chr21 C/T Chr21 | 22043945 22043979 | 34 |
| 39 AA/GC/AC | rs1735976 rs2827016 | A/G Chr21 A/C Chr21 | 22054777 22054808 | 31 |
| 40 AA/GA/AG/GG | rs1013069 rs2827307 | A/G Chr21 A/G Chr21 | 22545627 22545694 | 67 |
| 41 AT/GT/AC/GC | rs244260 rs244261 | A/G Chr21 C/T Chr21 | 23311737 23311825 | 88 |
| 42 CG/CC/AG/AC | rs2051265 rs198061 | A/C Chr21 C/G Chr21 | 23334109 23334156 | 47 |

Example 2

Determining Heterozygosity of the Tandem SNPs

As a complement to Example 1, genomic DNA samples from 300 anonymous subjects have been obtained from healthy young adults who are less than 35 years old. The samples are anonymous as the only data obtained were the geographic location of the Red Cross blood donor center, donor gender, and whether or not the donor was 35 and under. These samples were spot-checked to look for the haplotypes seen in the HapMap project.

Example 3

Detecting Fetal DNA from Maternal Serum

A cohort of patients who have been confirmed to have trisomy 21 by traditional karyotype analysis are examined. Tandem SNPs are used to demonstrate detection of trisomy in patients. DNA from 20 patients who have been characterized by traditional karyotype analysis to have trisomy 21 are analyzed with the tandem SNP panel.

Biological samples, including a buccal (cheek) swab and a blood sample are collected from a cohort of pregnant women. Maternal buccal swab samples are compared to maternal serum to demonstrate that a third (paternal) peak is observed in several of the tandem SNP assays. Approximately 20 maternal buccal swab to maternal serum comparisons are made. To control for experimental artifacts, genomic DNA samples from maternal buccal swabs are utilized for each target sequence. The buccal samples are subjected to the process in parallel with the maternal blood sample. Any artifacts generated by the CDCE/HiFi-PCR procedure (including nonspecific PCR amplification and polymerase-induced mutations) are revealed as background peaks in the buccal swab samples.

Example 4

Detecting Fetal Chromosomal Abnormalities

Figure 3:
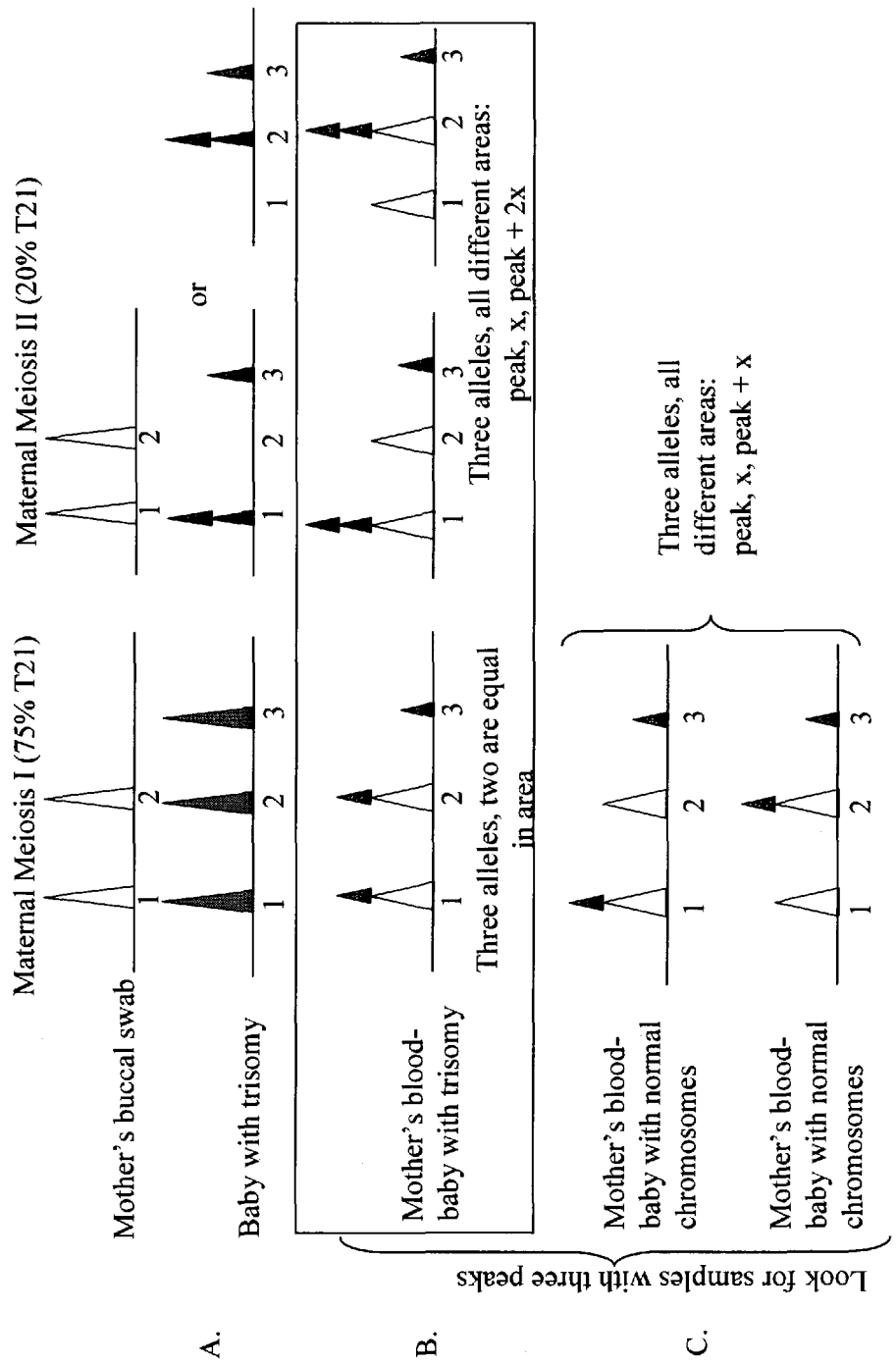
FIG. 3 depicts an example of a constant denaturant capillary electrophoresis electropherogram output. Each peak in these graphs represents the number of molecules of each allele for a marker detected in a sample.

A blinded study is performed where the goal is to detect 20 known trisomy 21 fetuses by assaying maternal serum from 40 patients (previously determined by amniocentesis or CVS) (see FIG. 3).

FIG. 3 depicts an example of a CDCE electropherogram output with the peaks at full scale. FIG. 3A depicts a sample from maternal buccal swab. Markers exhibiting two alleles are pursued. A baby with trisomy is expected to show either three alleles, evident by three peaks in a 1:1:1 ratio or two alleles in a 2:1 ratio. FIG. 3B depicts a sample from maternal serum. Markers exhibiting three alleles are informative. Maternal serum from a woman carrying a baby with trisomy is expected to exhibit three alleles, evident by two equal peaks with a third smaller peak if the trisomy occurred during meiosis I (75% of T21 cases) or three alleles with different areas if the trisomy occurred during meiosis II (20% of T21 cases) where areas are: peak, x, and peak+2x. FIG. 3C depicts analysis of a sample from maternal serum. Markers exhibiting three alleles are informative. Maternal serum from a woman with a normal baby with three alleles has three different areas where areas are: peak, x, and peak +x.

Interpretation of Results

For the case of the minimum heterozygosity, where both SNP1 and SNP2 are heterozygous at their respective loci at a rate of 25%, if 96 tandem SNPs are assayed, an average of 43 markers (44.5%) are expected to be heterozygous (two haplotypes) in the mother. The mother's expected heterozygosity is calculated using the following formula:

$$H=1-\Sigma p_i^2$$

for i=1 to k alleles where $p_i$=estimated allele frequency.

The allele frequencies at each SNP loci are expected to be 85% and 15% for the majority and minority alleles, respectively, assuming Hardy-Weinberg equilibrium. The desired third haplotype is expected to be present at an average of 6.4 markers (15%) of per maternal-fetal sample tested. Because most loci have a heterozygosity value greater than 25%, for every maternal-fetal sample tested using the panel of 96 tandem SNP assays, greater than about 6.4 markers are most informative. Thus, while a panel of 96 tandem SNPs may be used, 6 or 7 of those tandem SNPs may be informative for any one specific maternal-fetal sample tested, and a 'positive' result from any one of those tandem SNPs is informative.

Finally, in order to diagnose a trisomy, a "positive" tandem SNPs should be identified on both the p and the q arm of chromosome 21. Because of the comparative nature of the basic approach, the tandem SNP assay is predicted to have a detection rate of 95% (those that occur during maternal meiosis) for trisomy 21. If paternal samples are available, non-disjunctions that occur during paternal meiosis can also be detected. Thus, detection rates would be higher (about ~99%) with a 0% false positive rate.

Example 5

Tandem SNPs and Primers

Table 2 provides exemplary tandem SNPs of the invention and primers that can be used in the methods of the invention to detect the tandem SNPs. Certain embodiments of the present invention provide primers that can be used to amplify at least one of the SNPs. Certain embodiments of the present invention provide nucleic acid sequences that comprise at least one of the SNPs, e.g., at least one of the tandem SNPs.

TABLE 2

```
1) Whole sequence ::: rs432114-rs365433 CC/CT/GC/GT
AACAAATCTTCATCTTGGAATAGCCTGTGAGAATGCCTAATCATCTACGAATgTTACTTT GGCACCATCTACTGGACAgATTAAATAACAACCAACTCACTGTGGATTAGACCTACTTCT

ATTTCAG (SEQ ID NO: 1)

OLIGO start len tm gc % any c:\Documents and Settings\RamakrishnaMulpuri\Desktop\first 10
primers-redesigned\primer3_www_results_help.cgi-
PRIMER_THREE 3' seq (SEQ ID NOs: 2, 3)
LEFT PRIMER    20 20  55.08  45.00  3.00  2.00 ATAGCCTGTGAGAATGCCTA
RIGHT PRIMER  107 20  55.30  45.00  5.00  0.00 ATCCACAGTGAGTTGGTTGT
SEQUENCE SIZE: 127
INCLUDED REGION SIZE: 127
PRODUCT SIZE: 88, PAIR ANY COMPL: 5.00, PAIR 3' COMPL: 1.00

1 AACAAATCTTCATCTTGGAATAGCCTGTGAGAATGCCTAATCATCTACGAATgTTACTTT
               >>>>>>>>>>>>>>>>>>>>

61 GGCACCATCTACTGGACAgATTAAATAACAACCAACTCACTGTGGATTAGACCTACTTCT
                  <<<<<<<<<<<<<<<<<<<<

121 ATTTCAG

2) Whole sequence ::: rs7277033-rs2110153 CC/CT/TC/TT
PCR did not work
TTCCTGGAAAACAAAAGTATTTCTTTCATAGCCCAGCTAGCAtGATAAATCAGCgAGTCA

GAATTCTAGCTTTGTTGTAAGGTT (SEQ ID NO: 4)

OLIGO start len tm gc % any C:\Documents and Settings\RamakrishnaMulpuri\Desktop\first 10
primers-redesigned\primer3_www_results_help.cgi-PRIMER_THREE 3' seq (SEQ ID NOs: 5, 6)
LEFT PRIMER    2 20  51.63  30.00  5.00  3.00 TCCTGGAAAACAAAAGTATT
RIGHT PRIMER  84 21  51.36  33.33  4.00  0.00 AACCTTACAACAAAGCTAGAA
SEQUENCE SIZE: 84
INCLUDED REGION SIZE: 84
PRODUCT SIZE: 83, PAIR ANY COMPL: 3.00, PAIR 3' COMPL: 2.00

1 TTCCTGGAAAACAAAAGTATTTCTTTCATAGCCCAGCTAGCAtGATAAATCAGCgAGTCA
         >>>>>>>>>>>>>>>>>>>>

61 GAATTCTAGCTTTGTTGTAAGGTT
         <<<<<<<<<<<<<<<<<<<<<

3) Whole sequence ::: rs2822654-rs1882882 AA/AG/CA/CG
CACTAAGCCTTGGGGATCCAGCTGCTTaAGGACTAAGACCgTATCTAGCTCCTTTTAGTA

TTTCCACAGCA (SEQ ID NO: 7)

OLIGO start len tm gc % any c:\Documents and Settings\RamakrishnaMulpuri\Desktop\first 10
primers-redesigned\primer3_www_results_help.cgi-PRIMER_THREE 3' seq (SEQ ID NOs: 8, 9)
LEFT PRIMER    2 20  60.46  55.00  6.00  2.00 ACTAAGCCTTGGGGATCCAG
```

TABLE 2-continued

```
RIGHT PRIMER   71 21  54.78  38.10  3.00  0.00 TGCTGTGGAAATACTAAAAGG
SEQUENCE SIZE: 71
INCLUDED REGION SIZE: 71
PRODUCT SIZE: 70, PAIR ANY COMPL: 4.00, PAIR 3' COMPL: 0.00

1 CACTAAGCCTTGGGGATCCAGCTGCTTaAGGACTAAGACCgTATCTAGCTCCTTTTAGTA
     >>>>>>>>>>>>>>>>>>>>           <<<<<<<<<<

61 TTTCCACAGCA
     <<<<<<<<<<

4) Whole sequence ::: rs368657-rs376635 AA/AG/GA/GG
TCCTCCAGAGGTAATCCTGTGATCAGCACTAACaCCACATACCAGCCCTTTCATCAGCTT GTTGGAGAAGCATCTTTACTTCCCgCCAAGCAGTGACCTagataccatctcacaccagtt agaatcaggatcattaaaaagtcaagaaaaaacag (SEQ ID NO: 10)

OLIGO start len tm gc % any c:\Documents and Settings\RamakrishnaMulpuri\Desktop\first 10
primers-redesigned\primer3_www_results_help.cgi-PRIMER_THREE 3' seq (SEQ ID NOs: 11, 12)
LEFT PRIMER    3 20  55.20  50.00  5.00  3.00 CTCCAGAGGTAATCCTGTGA
RIGHT PRIMER 117 21  55.10  47.62  5.00  2.00 tggtgtgagatggtatctAGG
SEQUENCE SIZE: 155
INCLUDED REGION SIZE: 155
PRODUCT SIZE: 115, PAIR ANY COMPL: 3.00, PAIR 3' COMPL: 2.00

1 TCCTCCAGAGGTAATCCTGTGATCAGCACTAACaCCACATACCAGCCCTTTCATCAGCTT
     >>>>>>>>>>>>>>>>>>>>

61 GTTGGAGAAGCATCTTTACTTCCCgCCAAGCAGTGACCTagataccatctcacaccagtt
                                            <<<<<<<<<<<<<<<<<<<<<

121 agaatcaggatcattaaaaagtcaagaaaaaacag

5) Whole sequence ::: rs2822731-rs2822732 AA/AG/GA/GG
TCCAAGTATAATCCATGAATCTTGTTTAAATATAGATCAAaTAAACCACTATACCAAAAA CATCAAAAGACAACTGGGTAAATTTTTTAAATGACTAGCTATTTGATGTTAAgGAAGTAA

TGTTACTCTCTTATATACAATTTGAA (SEQ ID NO: 13)

OLIGO start len tm gc % any c:\Documents and Settings\RamakrishnaMulpuri\Desktop\first 10
primers-redesigned\primer3_www_results_help.cgi-PRIMER_THREE 3' seq (SEQ ID NOs: 14, 15)
LEFT PRIMER    6 22  50.35  27.27  6.00  3.00 GTATAATCCATGAATCTTGTTT
RIGHT PRIMER 146 22  45.69  22.73  6.00  1.00 TTCAAATTGTATATAAGAGAGT
SEQUENCE SIZE: 146
INCLUDED REGION SIZE: 146
PRODUCT SIZE: 141, PAIR ANY COMPL: 4.00, PAIR 3' COMPL: 2.00

1 TCCAAGTATAATCCATGAATCTTGTTTAAATATAGATCAAaTAAACCACTATACCAAAAA
          >>>>>>>>>>>>>>>>>>>>>>

61 CATCAAAAGACAACTGGGTAAATTTTTTAAATGACTAGCTATTTGATGTTAAgGAAGTAA

121 TGTTACTCTCTTATATACAATTTGAA
     <<<<<<<<<<<<<<<<<<<<<<

6) Whole sequence ::: rs6516899-rs455221 CC/CT/TC/TT
ATGGAACCGAAACTTCAAGTAGTTTCATAcGTATCACATTGACAGTTTTCTCTAAGTTTT CtGGTCTTATGACTCGTTGTTTCATTATTAAAACTGTGCCAGTGTATGCATAGGGCTTAG

AAATTTTTTAAT (SEQ ID NO: 16)

OLIGO start len tm gc % any c:\Documents and Settings\RamakrishnaMulpuri\Desktop\first 10
primers-redesigned\primer3_www_results_help.cgi-PRIMER_THREE 3' seq (SEQ ID NOs: 17, 18)
LEFT PRIMER    1 18  53.87  38.89  4.00  3.00 ATGGAACCGAAACTTCAA
RIGHT PRIMER  91 22  52.84  27.27  5.00  1.00 TTAATAATGAAACAACGAGTCA
SEQUENCE SIZE: 132
INCLUDED REGION SIZE: 132
PRODUCT SIZE: 91, PAIR ANY COMPL: 4.00, PAIR 3' COMPL: 0.00
   1 ATGGAACCGAAACTTCAAGTAGTTTCATAcGTATCACATTGACAGTTTTCTCTAAGTTTT
     >>>>>>>>>>>>>>>>>>

61 CtGGTCTTATGACTCGTTGTTTCATTATTAAAACTGTGCCAGTGTATGCATAGGGCTTAG
          <<<<<<<<<<<<<<<<<<<<<<

121 AAATTTTTTAAT
```

TABLE 2-continued

7) Whole sequence ::: rs7275381-rs12627144 GA/GG/TA/TG
acaggatccttcctgaagacaccaccttggggagggtgaagGataaagaatttgatcaga aatcaagggtggtgagatacatgttaaggatgaataaactggccttttaggattcttgct aaaAttagacaatgcagaggcaaccacagagtccaag (SEQ ID NO: 19)

OLIGO start len tm gc % any c:\Documents and Settings\RamakrishnaMulpuri\Desktop\first 10
primers-redesigned\primer3_www_results_help.cgi-PRIMER_THREE 3' seq (SEQ ID NOs: 20, 21)
LEFT PRIMER    10 19  55.53  47.37  4.00 0.00 ttcctgaagacaccacctt
RIGHT PRIMER  157 18  54.94  55.56  3.00 2.00 cttggactctgtggttgc
SEQUENCE SIZE: 157
INCLUDED REGION SIZE: 157
PRODUCT SIZE: 148, PAIR ANY COMPL: 5.00, PAIR 3' COMPL: 1.00

1 acaggatccttcctgaagacaccaccttggggagggtgaagGataaagaatttgatcaga
        >>>>>>>>>>>>>>>>>>>

61 aatcaagggtggtgagatacatgttaaggatgaataaactggccttttaggattcttgct 121 aaaAttagacaatgcagaggcaaccacagagtccaag
                  <<<<<<<<<<<<<<<<<<

8) Whole sequence ::: rs1999288-rs208897 CC/CT/TC
AATTTCCATTAAATCTTGTTCGTTGCTTTACTGAGGCACTGAAGTTACCAATGTTcCACT

GGTTGACCTGCGGGGCTATCTCTAGGTTATGTTACTCCAGAAAATGAATTGTGTATAAAA

GAGGCCTTGGAGGAAGGCGTTTTATTCaCATCAGTTGTTTTGCACATTGCTTA (SEQ ID NO: 22)

OLIGO start len tm gc % any c:\Documents and Settings\RamakrishnaMulpuri\Desktop\first 10
primers-redesigned\primer3_www_results_help.cgi-PRIMER_THREE 3' seq (SEQ ID NOs: 23, 24)
LEFT PRIMER    30 20  54.40  50.00  4.00 2.00 ACTGAGGCACTGAAGTTACC
RIGHT PRIMER  173 20  54.96  35.00  4.00 0.00 TAAGCAATGTGCAAAACAAC
SEQUENCE SIZE: 173
INCLUDED REGION SIZE: 173
PRODUCT SIZE: 144, PAIR ANY COMPL: 4.00, PAIR 3' COMPL: 0.00

1 AATTTCCATTAAATCTTGTTCGTTGCTTTACTGAGGCACTGAAGTTACCAATGTTcCACT
                                  >>>>>>>>>>>>>>>>>>>>

61 GGTTGACCTGCGGGGCTATCTCTAGGTTATGTTACTCCAGAAAATGAATTGTGTATAAAA

121 GAGGCCTTGGAGGAAGGCGTTTTATTCaCATCAGTTGTTTTGCACATTGCTTA
                  <<<<<<<<<<<<<<<<<<<<

9) Whole sequence ::: rs1475881-rs7275487 CA/CG/GA/GG
PCR did not work
TCGGTTTCAGCAGGAAAGTTATTTTTAATAACTTCCCTGTATTTcTTGGTTTCAGTTATTAATTAACTCA

TTAATGCTAAACTTTGTGATCCTAGGTTAAAAAACATATTCAAGATAGCTTCAGAATGTTTGGTATACA

AgTAGGTCTGGCTAAATATAAGTGTTAGCTTT CTCAAGCATC TAAATGCTGG (SEQ ID NO: 25)

OLIGO start len tm gc % any http://frodo.wi.mit.edu/cgi-bin/primer3/
primer3_www_results_help.cgi-PRIMER_THREE 3' seq (SEQ ID NOs: 26, 27)
LEFT PRIMER    10 20  48.49  25.00  5.00 3.00 GCAGGAAAGTTATTTTTAAT
RIGHT PRIMER  179 21  54.70  38.10  4.00 1.00 TGCTTGAGAAAGCTAACACTT
SEQUENCE SIZE: 191
INCLUDED REGION SIZE: 191
PRODUCT SIZE: 170, PAIR ANY COMPL: 5.00, PAIR 3' COMPL: 2.00

1 TCGGTTTCAGCAGGAAAGTTATTTTTAATAACTTCCCTGTATTTCTTGGTTTCAGTTATT
        >>>>>>>>>>>>>>>>>>>>

61 AATTAACTCATTAATGCTAAACTTTGTGATCCTAGGTTAAAAAACATATTCAAGATAGCT

121 TCAGAATGTTTGGTATACAAgTAGGTCTGGCTAAATATAAGTGTTAGCTTTCTCAAGCAT
                  <<<<<<<<<<<<<<<<<<<<<

181 CTAAATGCTGG

ALTERNATIVE:: (LESS THAN 5 bp APART)
AAGTTATTTTTAATAACTTCCCTGTATTTcTTGGTTTCAGTTATTAATTAACTCATTAAT

GCTAAACTTTGTGATCCTAGGTTAAAAAACATATTCAAGATAGCTTCAGAATGTTTGGTA

TACAAgTAGGTCTGGCTAAATATAAGTGTTAGCTTTCTCAAGCATC (SEQ ID NO: 28)

TABLE 2-continued

```
OLIGO      start len    tm   gc %  any http://frodo.wi.mit.edu/cgi-bin/primer3/
primer3_www_results_help.cgi-PRIMER_THREE 3' seq (SEQ ID NOs: 29, 30)
LEFT PRIMER     6  20 47.68 25.00 6.00 0.00 ATTTTTAATAACTTCCCTGT
RIGHT PRIMER  148  20 49.30 40.00 4.00 0.00 CACTTATATTTAGCCAGACC
SEQUENCE SIZE: 166
INCLUDED REGION SIZE: 166
PRODUCT SIZE: 143, PAIR ANY COMPL: 4.00, PAIR 3' COMPL: 1.00

1 AAGTTATTTTTAATAACTTCCCTGTATTTcTTGGTTTCAGTTATTAATTAACTCATTAAT
     >>>>>>>>>>>>>>>>>>>>

61 GCTAAACTTTGTGATCCTAGGTTAAAAAACATATTCAAGATAGCTTCAGAATGTTTGGTA

121 TACAAgTAGGTCTGGCTAAATATAAGTGTTAGCTTTCTCAAGCATC
        <<<<<<<<<<<<<<<<<<<<

10) Whole sequence ::: rs1735976-rs2827016 AA/AC/GA/GC
ATTCATTGTGTAGAAAGTGCCTGACTCAGTGTTTGGAAATTGTCTGACTTTTCCTCATAT aTAGTGTGGTTTCATGTTATTGTATATAAGAaCTGACATGAACTCTGTTTACAATAATCT

CCCAGTGCCATAAAGACCATAATAAATAATAT (SEQ ID NO: 31)

OLIGO      start len    tm   gc %  any c:\Documents and Settings\RamakrishnaMulpuri\Desktop\first 10
primers-redesigned\primer3_www_results_help.cgi-PRIMER_THREE 3' seq (SEQ ID NOs: 32, 33)
LEFT PRIMER    27  20 54.11 40.00 4.00 1.00 CAGTGTTTGGAAATTGTCTG
RIGHT PRIMER  129  20 55.17 45.00 3.00 2.00 GGCACTGGGAGATTATTGTA
SEQUENCE SIZE: 152
INCLUDED REGION SIZE: 152
PRODUCT SIZE: 103, PAIR ANY COMPL: 5.00, PAIR 3' COMPL: 1.00

1 ATTCATTGTGTAGAAAGTGCCTGACTCAGTGTTTGGAAATTGTCTGACTTTTCCTCATAT
                                >>>>>>>>>>>>>>>>>>>>

61 aTAGTGTGGTTTCATGTTATTGTATATAAGAaCTGACATGAACTCTGTTTACAATAATCT
                    <<<<<<<<<<

121 CCCAGTGCCATAAAGACCATAATAAATAATAT
        <<<<<<<<<<

2nd group of primers
11) Whole sequence ::: rs447349-rs2824097 CT/TC/TT (156 long)
CACTGGGTCCTGTTGTTAAGTACACATAATACCACaCAGGAGAAAATCAGGCTAATTGTA AATGGGCAACCTACTTAATTGTTTCATTAAAAAGCATACAGATTACATTTACACTAtAGC

TAGTCTTGTTTGTTTTTTATTTTGCAAAAGTAATTACGGCCC (SEQ ID NO: 34)

OLIGO      start len    tm   gc %  any http://frodo.wi.mit.edu/cgi-bin/primer3/
primer3_www_results_help.cgi-PRIMER_THREE 3' seq (SEQ ID NOs: 35, 36)
LEFT PRIMER     8  20 47.79 35.00 6.00 2.00 TCCTGTTGTTAAGTACACAT
RIGHT PRIMER  163  18 53.29 44.44 8.00 2.00 GGGCCGTAATTACTTTTG
SEQUENCE SIZE: 163
INCLUDED REGION SIZE: 163
PRODUCT SIZE: 156, PAIR ANY COMPL: 5.00, PAIR 3' COMPL: 1.00

1 CACTGGGTCCTGTTGTTAAGTACACATAATACCACaCAGGAGAAAATCAGGCTAATTGTA
             >>>>>>>>>>>>>>>>>>>>

61 AATGGGCAACCTACTTAATTGTTTCATTAAAAAGCATACAGATTACATTTACACTAtAGC

121 TAGTCTTGTTTGTTTTTTATTTTGCAAAAGTAATTACGGCCC
                  <<<<<<<<<<<<<<<<<<

12) Whole sequence ::: rs418989-rs13047336 AC/AT/CC
CTACTCAGTAGGCACTTTGTGTCTAGAAACTTCTGTGTCAACgGTTTTCCCTCTCTCTGG AATTCaTCAGGACAGAAGTGATTGGTGTGGTGGAAGAGGGTTGTGSTA (SEQ ID NO: 37)

OLIGO      start len    tm   gc %  any http://frodo.wi.mit.edu/cgi-bin/primer3/
primer3_www_results_help.cgi-PRIMER_THREE 3' seq (SEQ ID NOs: 38, 39)
LEFT PRIMER     3  21 54.50 47.62 5.00 3.00 ACTCAGTAGGCACTTTGTGTC
RIGHT PRIMER   97  18 54.95 50.00 2.00 0.00 TCTTCCACCACACCAATC
SEQUENCE SIZE: 108
INCLUDED REGION SIZE: 108
PRODUCT SIZE: 95, PAIR ANY COMPL: 5.00, PAIR 3' COMPL: 2.00
```

TABLE 2-continued

```
  1 CTACTCAGTAGGCACTTTGTGTCTAGAAACTTCTGTGTCAACgGTTTTCCCTCTCTCTGG
    >>>>>>>>>>>>>>>>>>>

61 AATTCaTCAGGACAGAAGTGATTGGTGTGGTGGAAGAGGGTTGTGSTA
            <<<<<<<<<<<<<<<<
```

13) Whole sequence ::: rs987980-rs987981 AG/GG/GT
TGGCTTTTCAAAGGTAAAATTTACTaAGTGTATTAATATTTTACCAATTTCCAGCCAGGA GAGTATGAATGTTGCATTATTACATTGCTTTGAAACAAAGCATTAgTCTTAATTCAGAAG

TTTAAATTCAGATGTTAACGTTGC (SEQ ID NO: 40)

```
OLIGO start len tm    gc %   any http://frodo.wi.mit.edu/cgi-bin/primer3/
primer3_www_results_help.cgi-PRIMER_THREE 3' seq (SEQ ID NOs: 41, 42)
LEFT PRIMER      1 19 53.67 31.58 6.00 2.00 TGGCTTTTCAAAGGTAAAA
RIGHT PRIMER   144 21 54.59 33.33 6.00 3.00 GCAACGTTAACATCTGAATTT
SEQUENCE SIZE: 144
INCLUDED REGION SIZE: 144
PRODUCT SIZE: 144, PAIR ANY COMPL: 6.00, PAIR 3' COMPL: 3.00

1 TGGCTTTTCAAAGGTAAAATTTACTaAGTGTATTAATATTTTACCAATTTCCAGCCAGGA
    >>>>>>>>>>>>>>>>>>>

61 GAGTATGAATGTTGCATTATTACATTGCTTTGAAACAAAGCATTAgTCTTAATTCAGAAG

121 TTTAAATTCAGATGTTAACGTTGC
           <<<<<<<<<<<<<<<<<<<<<
```

14) Whole sequence ::: rs4143392-rs4143391 CA/CG/GA/GG
TAAGTATTGAAGAAAGGAGAATTTAAATTACTTCATATACctgataaaggaaaacatata

CAAGGCAAATAAACATCTTAGATCATGACATATAAAATAATAGATTATTA (SEQ ID NO: 43)

```
OLIGO start len tm    gc %   any http://frodo.wi.mit.edu/cgi-bin/primer3/
primer3_www_results_help.cgi-PRIMER_THREE 3' seq (SEQ ID NOs: 44, 45)
LEFT PRIMER      7 20 49.56 25.00 4.00 4.00 TTGAAGAAAGGAGAATTTAA
RIGHT PRIMER    98 22 45.86 22.73 6.00 3.00 ATTTTATATGTCATGATCTAAG
SEQUENCE SIZE: 110
INCLUDED REGION SIZE: 110
PRODUCT SIZE: 92, PAIR ANY COMPL: 4.00, PAIR 3' COMPL: 1.00

1 TAAGTATTGAAGAAAGGAGAATTTAAATTACTTCATATACctgataaaggaaaacatata
         >>>>>>>>>>>>>>>>>>>>

61 CAAGGCAAATAAACATCTTAGATCATGACATATAAAATAATAGATTATTA
             <<<<<<<<<<<<<<<<<<<<<<
```

15) Whole sequence ::: rs1691324-rs13050434 CG/TA/TG (4 bp apart for right primer)
TGCAGAGATTACAGGTGTGAGCCACCGTGCCCAGCCTCATAACcGTTTCAACTACTTTTT

CACTTGACAAGCAGATGTGAAGTTAACAAAGTCACCCATATTTGAAATAAAGATAGTATA

TTCCTGGGGtAGGCAGAGGCAGTTGAGGATCATGAAATAACTATG (SEQ ID NO: 46)

```
OLIGO start len tm    gc %   any http://frodo.wi.mit.edu/cgi-bin/primer3/
primer3_www_results_help.cgi-PRIMER_THREE 3' seq (SEQ ID NOs: 47, 48)
LEFT PRIMER      4 19 49.78 47.37 4.00 4.00 AGAGATTACAGGTGTGAGC
RIGHT PRIMER   153 19 54.61 47.37 4.00 0.00 ATGATCCTCAACTGCCTCT
SEQUENCE SIZE: 165
INCLUDED REGION SIZE: 165
PRODUCT SIZE: 150, PAIR ANY COMPL: 4.00, PAIR 3' COMPL: 2.00

1 TGCAGAGATTACAGGTGTGAGCCACCGTGCCCAGCCTCATAACcGTTTCAACTACTTTTT
      >>>>>>>>>>>>>>>>>>>

61 CACTTGACAAGCAGATGTGAAGTTAACAAAGTCACCCATATTTGAAATAAAGATAGTATA

121 TTCCTGGGGtAGGCAGAGGCAGTTGAGGATCATGAAATAACTATG
              <<<<<<<<<<<<<<<<<<<
```

16) Whole sequence ::: rs11909758-rs9980111 (159 bp long) AG/AT/GT
TGCAATGAAACTCAAAAGAGAAAAGTTAACAGGTGCAAaAGGTAGTTTTATTATAAAAGG AGGGTAGGCAACAAGAATATGTTTAATTTTTCTTCCTTTTCATGAGTAAGGACAAGAGTg TCATATATGTGaatattttttatttaattttaaGTAGAAATCTGTTTTTAAAATATGGG (SEQ ID NO: 49)

TABLE 2-continued

```
OLIGO   start len  tm    gc %  any http://frodo.wi.mit.edu/cgi-bin/primer3/
primer3_www_results_help.cgi-PRIMER_THREE 3' seq (SEQ ID NOs: 50, 51)
LEFT PRIMER      6 20  49.91 30.00 3.00 0.00 TGAAACTCAAAAGAGAAAAG
RIGHT PRIMER   164 20  42.77 20.00 6.00 4.00 ACAGATTTCTACttaaaatt
SEQUENCE SIZE: 178
INCLUDED REGION SIZE: 178
PRODUCT SIZE: 159, PAIR ANY COMPL: 6.00, PAIR 3' COMPL: 3.00

1 TGCAATGAAACTCAAAAGAGAAAAGTTAACAGGTGCAAaAGGTAGTTTTATTATAAAAGG
     >>>>>>>>>>>>>>>>>>>>

61 AGGGTAGGCAACAAGAATATGTTTAATTTTTCTTCCTTTTCATGAGTAAGGACAAGAGTg

121 TCATATATGTGaatattttttatttaattttaaGTAGAAATCTGTTTTTAAAATATGGG
              <<<<<<<<<<<<<<<<<<<<

17) Whole sequence :::  rs854613-rs854614 AA/AG/TG
CCACCATTCATCAAAACTTTGATACTGGACTCAATTGTGAATTTGaCTTGAAATTTGATA ATGCTTTTGTTTTACTgTTCTGCTCAGCAAAATAGTACATGT (SEQ ID NO: 52)

OLIGO   start len  tm    gc %  any http://frodo.wi.mit.edu/cgi-bin/primer3/
primer3_www_results_help.cgi-PRIMER_THREE 3' seq (SEQ ID NOs: 53, 54)
LEFT PRIMER     12 20  49.40 35.00 6.00 1.00 CAAAACTTTGATACTGGACT
RIGHT PRIMER   102 19  46.05 31.58 6.00 1.00 ACATGTACTATTTTGCTGA
SEQUENCE SIZE: 102
INCLUDED REGION SIZE: 102
PRODUCT SIZE: 91, PAIR ANY COMPL: 5.00, PAIR 3' COMPL: 1.00

1 CCACCATTCATCAAAACTTTGATACTGGACTCAATTGTGAATTTGaCTTGAAATTTGATA
              >>>>>>>>>>>>>>>>>>>>

61 ATGCTTTTGTTTTACTgTTCTGCTCAGCAAAATAGTACATGT
              <<<<<<<<<<<<<<<<<<<

3rd group--order primers from 18-25
18) Whole sequence :::  rs2826225-rs2826226 AA/GA/GC
GCCTGCATAAAGTGAGGATGGTGTAGTAATTGGGTATCTCCAGTTATAAACACAAaAAGC ATGATAGAGCTGGGAcTGTGATTGCAGGAAAGCAATAGTCACTCCAAAAGGAGATCCTCA

TGATATGAATACGGAAGAAACAATATTTCCTGCTAATGTAGTAGCC (SEQ ID NO: 55)

OLIGO   start len  tm    gc %  any http://frodo.wi.mit.edu/cgi-bin/primer3/
primer3_www_results_help.cgi-PRIMER_THREE 3' seq (SEQ ID NOs: 56, 57)
LEFT PRIMER      2 20  58.17 50.00 4.00 0.00 CCTGCATAAAGTGAGGATGG
RIGHT PRIMER   120 21  59.27 47.62 6.00 0.00 TGAGGATCTCCTTTTGGAGTG
SEQUENCE SIZE: 166
INCLUDED REGION SIZE: 166
PRODUCT SIZE: 119, PAIR ANY COMPL: 6.00, PAIR 3' COMPL: 3.00

1 GCCTGCATAAAGTGAGGATGGTGTAGTAATTGGGTATCTCCAGTTATAAACACAAaAAGC
     >>>>>>>>>>>>>>>>>>>>

61 ATGATAGAGCTGGGAcTGTGATTGCAGGAAAGCAATAGTCACTCCAAAAGGAGATCCTCA
                                     <<<<<<<<<<<<<<<<<<<<<

121 TGATATGAATACGGAAGAAACAATATTTCCTGCTAATGTAGTAGCC

19) Whole sequence :::  rs2826842-rs232414 CA/CG/TA/TG
GCAAAGGGGTACTCTATGTAATGAAcATgacctggcagtactgacatctcctgagggact gttagaagtgcagactcttgtatcttttctcaagtctatgaaatctagacttcattttaa caagatgacccgatatttacatacacattaaagt
(SEQ ID NO: 58)

OLIGO   start len  tm    gc %  any http://frodo.wi.mit.edu/cgi-bin/primer3/
primer3_www_results_help.cgi-PRIMER_THREE 3' seq (SEQ ID NOs: 59, 60)
LEFT PRIMER      1 20  52.04 45.00 4.00 2.00 GCAAAGGGGTACTCTATGTA
RIGHT PRIMER   135 20  53.29 35.00 4.00 3.00 tatcgggtcatcttgttaaa
SEQUENCE SIZE: 154
INCLUDED REGION SIZE: 154
PRODUCT SIZE: 135, PAIR ANY COMPL: 3.00, PAIR 3' COMPL: 2.00
```

TABLE 2-continued

```
  1GCAAAGGGGTACTCTATGTAATGAAcATgacctggcagtactgacatctcctgagggact
    >>>>>>>>>>>>>>>>>>>>

61gttagaagtgcagactcttgtatcttttctcaagtctatgaaatctagacttcattttaa
                                             <<<<<

121caagatgacccgatatttacatacacattaaagt
    <<<<<<<<<<<<<<
20) Whole sequence ::: rs1980969-rs1980970 AA/AG/TA/TG
GTATCTAACAAAGCTCTGTCCAAAATTTTGAATTTCTCGTTAAAaGCATCATGATTATAG AACAGAGGTTACAATCAATTATTCAGTCACACAATCACTCTCATCAGTCATTAAGGTGCg

TACCTGGTGTTCCAGTTATTCAGTGTGGTATAACAAACTACCTGGAACTTAATG (SEQ ID NO: 61)

OLIGO start len tm gc % any http://frodo.wi.mit.edu/cgi-bin/primer3/
primer3_www_results_help.cgi-PRIMER_THREE 3' seq (SEQ ID NOs: 62, 63)
LEFT PRIMER    4 22  56.88  36.36  8.00  2.00 TCTAACAAAGCTCTGTCCAAAA
RIGHT PRIMER 148 21  56.12  42.86  3.00  1.00 CCACACTGAATAACTGGAACA
SEQUENCE SIZE: 174
INCLUDED REGION SIZE: 174
PRODUCT SIZE: 145, PAIR ANY COMPL: 4.00, PAIR 3' COMPL: 1.00

1GTATCTAACAAAGCTCTGTCCAAAATTTTGAATTTCTCGTTAAAaGCATCATGATTATAG
    >>>>>>>>>>>>>>>>>>>>>>

61AACAGAGGTTACAATCAATTATTCAGTCACACAATCACTCTCATCAGTCATTAAGGTGCg

121TACCTGGTGTTCCAGTTATTCAGTGTGGTATAACAAACTACCTGGAACTTAATG
        <<<<<<<<<<<<<<<<<<<<

4th group
21) Whole sequence ::: rs189900-rs2221492
AGAGTGGTTAAGTGACTTGATCAATTCCTCA GGTGGGGATTCAAGCTCTTAAAGCTGTAG ACTATGTCGTCCAAACAAAcACTGACATGAATATGACTTCCAATAGGCAAGAAAAGAGGC CTAGGTCgAGATACTGCAAGACATGCAAGCAATCTAGTAATGGCATAAAACCTGCTATCC

GAATTGGCTAAAATTATGTATT (SEQ ID NO: 64)

OLIGO start len tm gc % any http://fokker.wi.mit.edu/cgi-bin/primer3/
primer3_www_results_help.cgi-PRIMER_THREE 3' seq (SEQ ID NOs: 65, 66)
LEFT PRIMER   32 20  59.13  50.00  4.00  2.00 GGTGGGGATTCAAGCTCTTA
RIGHT PRIMER 180 22  59.38  40.91  5.00  3.00 GGATAGCAGGTTTTATGCCATT
SEQUENCE SIZE: 202
INCLUDED REGION SIZE: 202
PRODUCT SIZE: 149, PAIR ANY COMPL: 4.00, PAIR 3' COMPL: 1.00

1AGAGTGGTTAAGTGACTTGATCAATTCCTCAGGTGGGGATTCAAGCTCTTAAAGCTGTAG
                                   >>>>>>>>>>>>>>>>>>>>

61ACTATGTCGTCCAAACAAAcACTGACATGAATATGACTTCCAATAGGCAAGAAAAGAGGC

121CTAGGTCgAGATACTGCAAGACATGCAAGCAATCTAGTAATGGCATAAAACCTGCTATCC
                                         <<<<<<<<<<<<<<<<<<<<<<

181GAATTGGCTAAAATTATGTATT

22) Whole sequence ::: rs2827920-rs2827921
TTCTTTCTCACACAATGGGTTCCATTCCCACTACTACTCCATTCAAATTGAAGTGCCTTC aATGATTATTAAAAAACTCTCTTTAAAATAGCTCACGTAACCTTACATCCTTTGACTGAG

GCTCAACTCATGTCAATGCTTCAGTATCAACTTTTC (SEQ ID NO: 67)

OLIGO start len tm gc % any http://frodo.wi.mit.edu/cgi-bin/primer3/
primer3_www_results_help.cgi-PRIMER_THREE 3' seq (SEQ ID NOs: 68, 69)
LEFT PRIMER   14 21  59.93  47.62  7.00  0.00 AATGGGTTCCATTCCCACTAC
RIGHT PRIMER 125 20  58.96  50.00  7.00  1.00 TGAGCCTCAGTCAAAGGATG
SEQUENCE SIZE: 156
INCLUDED REGION SIZE: 156
PRODUCT SIZE: 112, PAIR ANY COMPL: 4.00, PAIR 3' COMPL: 1.00
```

TABLE 2-continued

```
  1 TTCTTTCTCACACAATGGGTTCCATTCCCACTACTACTCCATTCAAATTGAAGTGCCTTC
      >>>>>>>>>>>>>>>>>>>>>>

61 aATGATTATTAAAAAACTCTCTTTAAAATAGCTCAcGTAACCTTACATCCTTTGACTGAG
                    <<<<<<<<<<<<<<

121 GCTCAACTCATGTCAATGCTTCAGTATCAACTTTTC
       <<<<<

23) Whole sequence ::: rs198047-rs2827935
ATTTGTAATAACATTTAGTAAGTATTTATTTGAGGAGTTTGAATTTTGTTCTTGTTTATC TTGTTCTCTTTCTTcGTAGATTAGTTGGTGTTAACATCAATAGGATAACCCTTTCTTTCA GCATATGTGAATGAAATaAACCAATTATTGCCACTTTCCAGGTTAACCAGAATATACATA

GATACGAGGACAGTGGACTGTT (SEQ ID NO: 70)

OLIGO start len tm gc % any http://fokker.wi.mit.edu/cgi-bin/primer3/
primer3_www_results_help.cgi-PRIMER_THREE 3' seq (SEQ ID NOs: 71, 72)
LEFT PRIMER    30 22 56.07 31.82 4.00 1.00 TTGAGGAGTTTGAATTTTGTTC
RIGHT PRIMER  164 20 57.22 40.00 3.00 1.00 AACCTGGAAAGTGGCAATAA
SEQUENCE SIZE: 202
INCLUDED REGION SIZE: 202
PRODUCT SIZE: 135, PAIR ANY COMPL: 3.00, PAIR 3' COMPL: 2.00

1 ATTTGTAATAACATTTAGTAAGTATTTATTTGAGGAGTTTGAATTTTGTTCTTGTTTATC
                                  >>>>>>>>>>>>>>>>>>>>>>

61 TTGTTCTCTTTCTTcGTAGATTAGTTGGTGTTAACATCAATAGGATAACCCTTTCTTTCA

121 GCATATGTGAATGAAATaAACCAATTATTGCCACTTTCCAGGTTAACCAGAATATACATA
                   <<<<<<<<<<<<<<<<<<<<

181 GATACGAGGACAGTGGACTGTT

24) Whole sequence ::: rs9978999-rs9979175
tagggcagagagagcaagcaagctctctaccttctcatataagggcactaatcccaccat gaaggcgccactgtcatgacCtgattatgtcacaaagaccccggggcaaatattaccact Gtgaggagtacagttttagcatgtgaattttggaagaacacaaacatttag (SEQ ID NO: 73)

OLIGO start len tm gc % any http://frodo.wi.mit.edu/cgi-bin/primer3/
primer3_www_results_help.cgi-PRIMER_THREE 3' seq (SEQ ID NOs: 74, 75)
LEFT PRIMER    14 21 58.50 52.38 4.00 0.00 gcaagcaagctctctaccttc
RIGHT PRIMER  160 22 59.98 36.36 4.00 2.00 tgttcttccaaaattcacatgc
SEQUENCE SIZE: 171
INCLUDED REGION SIZE: 171
PRODUCT SIZE: 147, PAIR ANY COMPL: 3.00, PAIR 3' COMPL: 0.00

1 tagggcagagagagcaagcaagctctctaccttctcatataagggcactaatcccaccat
            >>>>>>>>>>>>>>>>>>>>>

61 gaaggcgccactgtcatgacCtgattatgtcacaaagaccccggggcaaatattaccact

121 Gtgaggagtacagttttagcatgtgaattttggaagaacacaaacatttag
                 <<<<<<<<<<<<<<<<<<<<<<

25) Whole sequence ::: rs1034346-rs12481852
ATTCTAATTTTAAATATCATTGATGTAGAACATTCTATTTCACTATTCCTTCATTTTATT aTTATGGGAAATTATATACAGTTCTCCAGATTTTTAAAGCCTTGCTAACATGTTTTAAGT CACACAAATATTCTcCTGTGGGAAAATGACAGTAATTTAGTGTGCAACAATTATATAGAA

CTATTTTTCAAACTT (SEQ ID NO: 76)

OLIGO start len tm gc % any http://frodo.wi.mit.edu/cgi-bin/primer3/
primer3_www_results_help.cgi-PRIMER_THREE 3' seq (SEQ ID NOs: 77, 78)
LEFT PRIMER    37 21 50.04 23.81 2.00 0.00 ATTTCACTATTCCTTCATTTT
RIGHT PRIMER  173 22 50.19 27.27 6.00 3.00 TAATTGTTGCACACTAAATTAC
SEQUENCE SIZE: 195
INCLUDED REGION SIZE: 195
PRODUCT SIZE: 137, PAIR ANY COMPL: 4.00, PAIR 3' COMPL: 2.00
```

TABLE 2-continued

```
  1 ATTCTAATTTTAAATATCATTGATGTAGAACATTCTATTTCACTATTCCTTCATTTTATT
      >>>>>>>>>>>>>>>>>>>>

61 aTTATGGGAAATTATATACAGTTCTCCAGATTTTTAAAGCCTTGCTAACATGTTTTAAGT

121 CACACAAATATTCTcCTGTGGGAAAATGACAGTAATTTAGTGTGCAACAATTATATAGAA
                                         <<<<<<<<<<<<<<<<<<<<

181 CTATTTTTCAAACTT
```

5<sup>th</sup> group
26) Whole sequence ::: rs7509629-rs2828358
ACTGTCATGGACTTAAACAATTGTCTTTGAATTGTCTTTTTTCATACTTTTATTTGCATC TTTcCACTAAAAAGATGgCACAAAGTAATCCTAGTTTACATTTTTTACCATGTAATTCCA

TATTACTTTTTCCTGAAA (SEQ ID NO: 79)

OLIGO start len tm gc % any http://frodo.wi.mit.edu/cgi-bin/primer3/
primer3_www_results_help.cgi-PRIMER_THREE 3' seq (SEQ ID NOs: 80, 81)
LEFT PRIMER     1 20 50.46 35.00 4.00 0.00 ACTGTCATGGACTTAAACAA
RIGHT PRIMER  137 22 53.49 27.27 4.00 0.00 TTCAGGAAAAAGTAATATGGAA
SEQUENCE SIZE: 138
INCLUDED REGION SIZE: 138
PRODUCT SIZE: 137, PAIR ANY COMPL: 4.00, PAIR 3' COMPL: 0.00

```
  1 ACTGTCATGGACTTAAACAATTGTCTTTGAATTGTCTTTTTTCATACTTTTATTTGCATC
      >>>>>>>>>>>>>>>>>>>>

61 TTTcCACTAAAAAGATGgCACAAAGTAATCCTAGTTTACATTTTTTACCATGTAATTCCA
                                                        <<<<<

121 TATTACTTTTTCCTGAAA
      <<<<<<<<<<<<<<<<<
```

6<sup>th</sup> group
27) Whole sequence ::: rs4817013-rs7277036
aaagaaaaaaaagccacagaaatcagtcctagagaaaacCgatctatgagctgcctgaAa ataattataaaataactatcataaaaatgcccagtgagatataagaaaacacagacaac (SEQ ID NO: 82)

OLIGO start len tm gc % any http://frodo.wi.mit.edu/cgi-bin/primer3/
primer3_www_results_help.cgi-PRIMER_THREE 3' seq (SEQ ID NOs: 83, 84)
LEFT PRIMER     8 21 56.10 38.10 4.00 2.00 aaaaagccacagaaatcagtc
RIGHT PRIMER  107 22 55.60 36.36 4.00 2.00 ttcttatatctcactgggcatt
SEQUENCE SIZE: 119
INCLUDED REGION SIZE: 119
PRODUCT SIZE: 100, PAIR ANY COMPL: 5.00, PAIR 3' COMPL: 1.00

```
  1 aaagaaaaaaaagccacagaaatcagtcctagagaaaacCgatctatgagctgcctgaAa
         >>>>>>>>>>>>>>>>>>>>>

61 ataattataaaataactatcataaaaatgcccagtgagatataagaaaacacagacaac
                              <<<<<<<<<<<<<<<<<<<<<<
```

28) Whole sequence ::: rs9981121-rs2829696
CAAGGTCAGAGAAGTTATCTTGGATGGTAGAAGAGAAGAAAGGAGAAGAAaGGATAAGCA GAAAATCAAAAAGGGCATAAAAAAATTACTGGgGAAAATAATTCTTAGTCACTCACCATT

TCTTATGTTTGTGAAAACAGAAA (SEQ ID NO: 85)

OLIGO start len tm gc % any http://frodo.wi.mit.edu/cgi-bin/primer3/
primer3_www_results_help.cgi-PRIMER_THREE 3' seq (SEQ ID NOs: 86, 87)
LEFT PRIMER    22 22 56.24 45.45 2.00 0.00 GGATGGTAGAAGAGAAGAAAGG
RIGHT PRIMER  134 22 55.74 31.82 4.00 1.00 TCACAAACATAAGAAATGGTGA
SEQUENCE SIZE: 143
INCLUDED REGION SIZE: 143
PRODUCT SIZE: 113, PAIR ANY COMPL: 3.00, PAIR 3' COMPL: 0.00

```
  1 CAAGGTCAGAGAAGTTATCTTGGATGGTAGAAGAGAAGAAAGGAGAAGAAaGGATAAGCA
                           >>>>>>>>>>>>>>>>>>>>>>

61 GAAAATCAAAAAGGGCATAAAAAAATTACTGGgGAAAATAATTCTTAGTCACTCACCATT
                                                    <<<<<<<

121 TCTTATGTTTGTGAAAACAGAAA
      <<<<<<<<<<<<<<<<<
```

TABLE 2-continued

29) Whole sequence ::: rs455921-rs2898102
gaccacaattcacaaatgcaaagatgcagaaccaacctaagtggccaCtgactaatgaga ggataaagaagatgtggcatatataTatcagggactactactcagccattacaaggaaca aaataatgtcttttgc (SEQ ID NO: 88)

OLIGO start len tm gc % any http://frodo.wi.mit.edu/cgi-bin/primer3/
primer3_www_results_help.cgi-PRIMER_THREE 3' seq (SEQ ID NOs: 89, 90)
LEFT PRIMER    17 20  59.85  45.00  4.00  0.00 tgcaaagatgcagaaccaac
RIGHT PRIMER  123 22  59.63  36.36  2.00  1.00 ttttgttccttgtaatggctga
SEQUENCE SIZE: 136
INCLUDED REGION SIZE: 136
PRODUCT SIZE: 107, PAIR ANY COMPL: 5.00, PAIR 3' COMPL: 1.00

1 gaccacaattcacaaatgcaaagatgcagaaccaacctaagtggccaCtgactaatgaga
                     >>>>>>>>>>>>>>>>>>>>

61 ggataaagaagatgtggcatatataTatcagggactactactcagccattacaaggaaca
                                       <<<<<<<<<<<<<<<<<<<

121 aaataatgtcttttgc
       <<<

30) Whole sequence ::: rs2898102-rs458848
gaccacaattcacaaatgcaaagatgcagaaccaacctaagtggccactgactaatgaga ggataaagaagatgtggcatatataCatcagggactactTctcagccattacaaggaaca aaataatgtcttttgcaacaacttggatagagctggaggc (SEQ ID NO: 91)

OLIGO start len tm gc % any http://frodo.wi.mit.edu/cgi-bin/primer3/
primer3_www_results_help.cgi-PRIMER_THREE 3' seq (SEQ ID NOs: 92, 93)
LEFT PRIMER    17 20  59.85  45.00  4.00  0.00 tgcaaagatgcagaaccaac
RIGHT PRIMER  160 21  59.86  52.38  4.00  3.00 gcctccagctctatccaagtt
SEQUENCE SIZE: 160
INCLUDED REGION SIZE: 160
PRODUCT SIZE: 144, PAIR ANY COMPL: 4.00, PAIR 3' COMPL: 3.00

1 gaccacaattcacaaatgcaaagatgcagaaccaacctaagtggccactgactaatgaga
                     >>>>>>>>>>>>>>>>>>>>

61 ggataaagaagatgtggcatatataCatcagggactactTctcagccattacaaggaaca 121 aaataatgtcttttgcaacaacttggatagagctggaggc
                        <<<<<<<<<<<<<<<<<<<<<

31) Whole sequence ::: rs961301-rs2830208
AATCCTAGACCTTGGATTGCAAGAGACTCCTTAATATCTTCCCATGTCCACATTTcCTTC ACATAGTTTGAATGTGGCTTCTATTATATACAGATACAAGATTCAAATCCAACCTCTAtG

ATGACTGGTCTTGTGAATAAGCAGAAGAGGCACTAACAAT (SEQ ID NO: 94)

OLIGO start len tm gc % any http://frodo.wi.mit.edu/cgi-bin/primer3/
primer3_www_results_help.cgi-PRIMER_THREE 3' seq (SEQ ID NOs: 95, 96)
LEFT PRIMER    29 22  57.95  40.91  4.00  2.00 CCTTAATATCTTCCCATGTCCA
RIGHT PRIMER  160 22  57.35  40.91  3.00  0.00 ATTGTTAGTGCCTCTTCTGCTT
SEQUENCE SIZE: 160
INCLUDED REGION SIZE: 160
PRODUCT SIZE: 132, PAIR ANY COMPL: 3.00, PAIR 3' COMPL: 1.00

1 AATCCTAGACCTTGGATTGCAAGAGACTCCTTAATATCTTCCCATGTCCACATTTcCTTC
                                 >>>>>>>>>>>>>>>>>>>>>>

61 ACATAGTTTGAATGTGGCTTCTATTATATACAGATACAAGATTCAAATCCAACCTCTAtG

121 ATGACTGGTCTTGTGAATAAGCAGAAGAGGCACTAACAAT
                        <<<<<<<<<<<<<<<<<<<<<<

32) Whole sequence ::: rs2174536-rs458076
AAGAGAAGTGAGGTCAGCAGCTGCAAGCCACCTCCGTCATTTAGAAAAGCTTCaTGATGT AGTGTGTCGTTTCGATGTGACACTGTCTCACAGAGTTAAAATGATGTtAAGGAACTGTTC

AATGGAAATTTAGAAATTTCTCTTTTTCTCAATTTTAGTGTA (SEQ ID NO: 97)

TABLE 2-continued

```
OLIGO start len tm gc % any http://frodo.wi.mit.edu/cgi-bin/primer3/
primer3_www_results_help.cgi-PRIMER_THREE 3' seq (SEQ ID NOs: 98, 99)
LEFT PRIMER     3 20 57.31 55.00  5.00 5.00 GAGAAGTGAGGTCAGCAGCT
RIGHT PRIMER  136 22 53.92 27.27  6.00 2.00 TTTCTAAATTTCCATTGAACAG
SEQUENCE SIZE: 162
INCLUDED REGION SIZE: 162
PRODUCT SIZE: 134, PAIR ANY COMPL: 4.00, PAIR 3' COMPL: 2.00

1 AAGAGAAGTGAGGTCAGCAGCTGCAAGCCACCTCCGTCATTTAGAAAAGCTTCaTGATGT
     >>>>>>>>>>>>>>>>>>>>

61 AGTGTGTCGTTTCGATGTGACACTGTCTCACAGAGTTAAAATGATGTtAAGGAACTGTTC
                                                    <<<<<<

121 AATGGAAATTTAGAAATTTCTCTTTTTCTCAATTTTAGTGTA
       <<<<<<<<<<<<<<<<

33) Whole sequence ::: rs432557-rs1012766
ATGGCTGAATAGTATTCCCTTGTGTATATATCTaTTTATCCTTTTATTCATTGATGGACA

CTTAGGCTGATTTTCTCTCTTCTCATGGCTGGCTTCTCATCACCCTTTGGTCCTCCTGTA

TCCTCgTGTAATAAAGCTCTTCCCCAATATCTCGATAGAT (SEQ ID NO: 100)

OLIGO start len tm gc % any http://frodo.wi.mit.edu/cgi-bin/primer3/
primer3_www_results_help.cgi-PRIMER_THREE 3' seq (SEQ ID NOs: 101, 102)
LEFT PRIMER     3 22 57.77 45.45  9.00 0.00 GGCTGAATAGTATTCCCTTGTG
RIGHT PRIMER  155 20 59.22 50.00  4.00 2.00 TCGAGATATTGGGGAAGAGC
SEQUENCE SIZE: 160
INCLUDED REGION SIZE: 160
PRODUCT SIZE: 153, PAIR ANY COMPL: 5.00, PAIR 3' COMPL: 1.00

1 ATGGCTGAATAGTATTCCCTTGTGTATATATCTaTTTATCCTTTTATTCATTGATGGACA
       >>>>>>>>>>>>>>>>>>>>>>

61 CTTAGGCTGATTTTCTCTCTTCTCATGGCTGGCTTCTCATCACCCTTTGGTCCTCCTGTA

121 TCCTCgTGTAATAAAGCTCTTCCCCAATATCTCGATAGAT
         <<<<<<<<<<<<<<<<<<<<

34) Whole sequence ::: rs10222076-rs10222075
cattttaacttgatta cctccacaaagactattccagaataaggttatgttctgaggtat tagggggttacAacttcaacatatgaattttgagtggacacaattcaacccatagcaCCTC

CGTGTAAGAGCTGGGAAGGGAAAGTGGCTAAGTTGTGCAAATGTGCACATTGGTTGGAGA

TGATTAACTTCTGGCATGT (SEQ ID NO: 103)

OLIGO start len tm gc % any http://frodo.wi.mit.edu/cgi-bin/primer3/
primer3_www_results_help.cgi-PRIMER_THREE 3' seq (SEQ ID NOs: 104, 105)
LEFT PRIMER    17 22 58.32 45.45  4.00 2.00 cctccacaaagactattccaga
RIGHT PRIMER  146 20 60.76 55.00  4.00 2.00 CACTTTCCCTTCCCAGCTCT
SEQUENCE SIZE: 199
INCLUDED REGION SIZE: 199
PRODUCT SIZE: 130, PAIR ANY COMPL: 4.00, PAIR 3' COMPL: 3.00

1 cattttaacttgattacctccacaaagactattccagaataaggttatgttctgaggtat
                     >>>>>>>>>>>>>>>>>>>>>>

61 tagggggttacAacttcaacatatgaattttgagtggacacaattcaacccatagcaCCTC

121 CGTGTAAGAGCTGGGAAGGGAAAGTGGCTAAGTTGTGCAAATGTGCACATTGGTTGGAGA
         <<<<<<<<<<<<<<<<<<<<

181 TGATTAACTTCTGGCATGT

35) Whole sequence ::: rs11088023-rs11088024
aggggggaaattggcaatctgattctaaaattcataCggaaaaaaacaatggagttagaat aactaaaacaagtccgaaaaagaaaaagaaatggaggactaatgctacctgatttcaagt cttatcTtataaaatctacatcaataaaggacaagttg (SEQ ID NO: 106)
```

TABLE 2-continued

```
OLIGO start len tm gc % any http://frodo.wi.mit.edu/cgi-bin/primer3/
primer3_www_results_help.cgi-PRIMER_THREE 3' seq (SEQ ID NOs: 107, 108)
LEFT PRIMER     6 20 54.34 35.00 7.00 3.00 gaaattggcaatctgattct
RIGHT PRIMER  157 21 51.94 33.33 5.00 0.00 caacttgtcctttattgatgt
SEQUENCE SIZE: 157
INCLUDED REGION SIZE: 157
PRODUCT SIZE: 152, PAIR ANY COMPL: 4.00, PAIR 3' COMPL: 0.00

1 aggggggaaattggcaatctgattctaaaattcataCggaaaaaaacaatggagttagaat
       >>>>>>>>>>>>>>>>>>>>

61 aactaaaacaagtccgaaaaagaaaaagaaatggaggactaatgctacctgatttcaagt 121 cttatcTtataaatctacatcaataaaggacaagttg
              <<<<<<<<<<<<<<<<<<<<<

36) Whole sequence ::: rs1011734-rs1011733
TCTGTGTTTGTCTATGTTGATAAAACATTGAAATGCCAaATAGCTCAAAGGTCATTCACT

TAAGAAATCTAAGTACTGATAACATCTTAGCCCCGATTCTTCATAGGCATTGTTAAGCCT

ATTATAATTTTGGTtCAGAGAGAAGGTAAACTATATTCCAGACAGGCATATAA (SEQ ID NO: 109)

OLIGO start len tm gc % any http://frodo.wi.mit.edu/cgi-bin/primer3/
primer3_www_results_help.cgi-PRIMER_THREE 3' seq (SEQ ID NOs: 110, 111)
LEFT PRIMER    12 22 50.06 22.73 6.00 2.00 CTATGTTGATAAAACATTGAAA
RIGHT PRIMER  167 20 51.09 40.00 4.00 2.00 GCCTGTCTGGAATATAGTTT
SEQUENCE SIZE: 173
INCLUDED REGION SIZE: 173
PRODUCT SIZE: 156, PAIR ANY COMPL: 5.00, PAIR 3' COMPL: 3.00

1 TCTGTGTTTGTCTATGTTGATAAAACATTGAAATGCCAaATAGCTCAAAGGTCATTCACT
           >>>>>>>>>>>>>>>>>>>>>>

61 TAAGAAATCTAAGTACTGATAACATCTTAGCCCCGATTCTTCATAGGCATTGTTAAGCCT

121 ATTATAATTTTGGTtCAGAGAGAAGGTAAACTATATTCCAGACAGGCATATAA
                <<<<<<<<<<<<<<<<<<<<

37) Whole sequence ::: rs2831244-rs9789838
TGCAGGGCATATAATCTAAGCTGTAAACGTCCTGTcAGAAGACAACATATTCATCTTGCT AAGGTtTAAGCTATATGACTGGCACTGTGCTCAACTCAGAGTCATTGAATGAACAGTATT

TATTTA (SEQ ID NO: 112)

OLIGO start len tm gc % any
http://frodo.wi.mit.edu/cgi-bin/primer3/primer3_www_results_help.cgi - PRIMER_THREE 3' seq
(SEQ ID NOs: 113, 114)

LEFT PRIMER     3 22 55.40 40.91 5.00 3.00 CAGGGCATATAATCTAAGCTGT
RIGHT PRIMER  107 21 55.99 47.62 7.00 2.00 CAATGACTCTGAGTTGAGCAC
SEQUENCE SIZE: 126
INCLUDED REGION SIZE: 126
PRODUCT SIZE: 105, PAIR ANY COMPL: 4.00, PAIR 3' COMPL: 2.00

1 TGCAGGGCATATAATCTAAGCTGTAAACGTCCTGTcAGAAGACAACATATTCATCTTGCT
        >>>>>>>>>>>>>>>>>>>>>>

61 AAGGTtTAAGCTATATGACTGGCACTGTGCTCAACTCAGAGTCATTGAATGAACAGTATT
              <<<<<<<<<<<<<<<<<<<<<

121 TATTTA

38) Whole sequence ::: rs8132769-rs2831440
TTCACATTATTCCCTTAAAATAAACTCTCTCCCTCCCCTCTCCCGTCTCAaCCTTGTCCC TTTCTTTATATAATGGGTAATtCGTTAATGTCAGCAGAATAGTTTTGGGGCCATAATGGC

AAGTATCACGTG (SEQ ID NO: 115)

OLIGO start len tm gc % any
http://frodo.wi.mit.edu/cgi-bin/primer3/primer3_www_results_help.cgi - PRIMER_THREE 3' seq
(SEQ ID NOs: 116, 117)

LEFT PRIMER    23 19 56.84 57.89 1.00 0.00 AACTCTCTCCCTCCCCTCT
RIGHT PRIMER  115 20 56.24 40.00 4.00 2.00 TATGGCCCCAAAACTATTCT
SEQUENCE SIZE: 132
INCLUDED REGION SIZE: 132
PRODUCT SIZE: 93, PAIR ANY COMPL: 2.00, PAIR 3' COMPL: 0.00
```

TABLE 2-continued

```
  1 TTCACATTATTCCCTTAAAATAAACTCTCTCCCTCCCCTCTCCCGTCTCAaCCTTGTCCC
         >>>>>>>>>>>>>>>>>>>>

61 TTTCTTTATATAATGGGTAATtCGTTAATGTCAGCAGAATAGTTTTGGGGCCATAATGGC
                  <<<<<<<<<<<<<<<<<<<

121 AAGTATCACGTG
```

39) Whole sequence ::: rs8134080-rs2831524
TCAGGAAGCAACAAGTACTGGGCAGATTGATACTGTAGCTaGGCTCTAGCTCTATACCTC TAGAATaaatgttacaaactagcaacttgaaagctaaacctggcccacag (SEQ ID NO: 118)

OLIGO   start len tm gc % any
http://frodo.wi.mit.edu/cgi-bin/primer3/primer3_www_results_help.cgi - PRIMER_THREE 3' seq
(SEQ ID NOs: 119, 120)

LEFT PRIMER    11 20 55.75 45.00 6.00 2.00 ACAAGTACTGGGCAGATTGA
RIGHT PRIMER  104 20 56.27 45.00 4.00 2.00 gccaggtttagctttcaagt
SEQUENCE SIZE: 110
INCLUDED REGION SIZE: 110
PRODUCT SIZE: 94, PAIR ANY COMPL: 4.00, PAIR 3' COMPL: 3.00

```
  1 TCAGGAAGCAACAAGTACTGGGCAGATTGATACTGTAGCTaGGCTCTAGCTCTATACCTC
         >>>>>>>>>>>>>>>>>>>>

61 TAGAATaaatgttacaaactagcaacttgaaagctaaacctggcccacag
               <<<<<<<<<<<<<<<<<<<
```

40) Whole sequence ::: rs4817219-rs4817220
tggttcttgagaatttttatatcaggagaaacactgtcagtCtgtattgaaaggaacagag aaaatTcgaaattaaagaagactattaaacctccaaaattctggca (SEQ ID NO: 121)

OLIGO   start len tm gc % any
http://frodo.wi.mit.edu/cgi-bin/primer3/primer3_www_results_help.cgi - PRIMER_THREE 3' seq
(SEQ ID NOs: 122, 123)

LEFT PRIMER    14 22 51.54 31.82 4.00 3.00 ttttatatcaggagaaacactg
RIGHT PRIMER  104 21 55.03 33.33 8.00 2.00 ccagaattttggaggtttaat
SEQUENCE SIZE: 106
INCLUDED REGION SIZE: 106
PRODUCT SIZE: 91, PAIR ANY COMPL: 4.00, PAIR 3' COMPL: 2.00

```
  1 TggttcttgagaatttttatatcaggagaaacactgtcagtCtgtattgaaaggaacagag
             >>>>>>>>>>>>>>>>>>>>>>

61 aaaatTcgaaattaaagaagactattaaacctccaaaattctggca
                <<<<<<<<<<<<<<<<<<<<<
```

41) Whole sequence ::: rs2250911-rs2250997
GCATCAAACTACACACTGTCATTCCTCCTTTATCTCCAAAAGCTTGAAAATTCCTCACTT GTaTCTCATTCTTTCTCTCTTAGAAAACTGATCACCTCTGATGAATTAgAACGGAATGAC

CAAGCTTTGGGAGAGGCAAAAGAATCTCGGTGTTAAAGACTCAGAGTTTAA (SEQ ID NO: 124)

OLIGO   start len tm gc % any
http://frodo.wi.mit.edu/cgi-bin/primer3/primer3_www_results_help.cgi - PRIMER_THREE 3' seq
(SEQ ID NOs: 125, 126)

LEFT PRIMER    17 22 58.65 40.91 3.00 0.00 TGTCATTCCTCCTTTATCTCCA
RIGHT PRIMER  144 20 59.42 45.00 4.00 2.00 TTCTTTTGCCTCTCCCAAAG
SEQUENCE SIZE: 171
INCLUDED REGION SIZE: 171
PRODUCT SIZE: 128, PAIR ANY COMPL: 4.00, PAIR 3' COMPL: 0.00

```
  1 GCATCAAACTACACACTGTCATTCCTCCTTTATCTCCAAAAGCTTGAAAATTCCTCACTT
               >>>>>>>>>>>>>>>>>>>>>>

61 GTaTCTCATTCTTTCTCTCTTAGAAAACTGATCACCTCTGATGAATTAgAACGGAATGAC

121 CAAGCTTTGGGAGAGGCAAAAGAATCTCGGTGTTAAAGACTCAGAGTTTAA
         <<<<<<<<<<<<<<<<<<<<
```

TABLE 2-continued

42) Whole sequence ::: rs2831899-rs2831900
TTGAAAATTAAGAAACCCTGGCACAGTGTTGACTGGAGCCaCTTACCTTAATAGAAAATA

AAGCTCACATATATCCATAATGAAAAGCAGAGACCAGCACAACCATAGTCACCTGACAGT

TTtAAAATCCAAGGCCAGGATCTTCTCAACTCAGGCCCACTCA (SEQ ID NO: 127)

OLIGO start len tm gc % any
http://frodo.wi.mit.edu/cgi-bin/primer3/primer3_www_results_help.cgi - PRIMER_THREE 3' seq
(SEQ ID NOs: 128, 129)

LEFT PRIMER    15 20  60.63  55.00  6.00 2.00 ACCCTGGCACAGTGTTGACT
RIGHT PRIMER  159 20  59.80  50.00  4.00 2.00 TGGGCCTGAGTTGAGAAGAT
SEQUENCE SIZE: 163
INCLUDED REGION SIZE: 163
PRODUCT SIZE: 145, PAIR ANY COMPL: 5.00, PAIR 3' COMPL: 1.00

1 TTGAAAATTAAGAAACCCTGGCACAGTGTTGACTGGAGCCaCTTACCTTAATAGAAAATA
        >>>>>>>>>>>>>>>>>>>>

61 AAGCTCACATATATCCATAATGAAAAGCAGAGACCAGCACAACCATAGTCACCTGACAGT

121 TTtAAAATCCAAGGCCAGGATCTTCTCAACTCAGGCCCACTCA
            <<<<<<<<<<<<<<<<<<<<

43) Whole sequence ::: rs2831902-rs2831903
CACATAACTAATAAATTTGTAAGTATGTGCAACGGCTCACaCTTGCTTCCAGAATGGCAC

CTAAAAAACAGATTTACCTCTCCCCAAATTCAGATATGGAATTAAATGTAATGTCAGGAA

AAcTGTCTAAGAGTTGGAAATGGGAAAAAAATGTTCTTTTGGT (SEQ ID NO: 212)

OLIGO start len tm gc % any
http://frodo.wi.mit.edu/cgi-bin/primer3/primer3_www_results_help.cgi - PRIMER_THREE 3' seq
(SEQ ID NOs: 213, 130)

LEFT PRIMER    14 21  53.16  33.33  4.00 2.00 AATTTGTAAGTATGTGCAACG
RIGHT PRIMER  149 20  56.27  35.00  2.00 0.00 TTTTTCCCATTTCCAACTCT
SEQUENCE SIZE: 163
INCLUDED REGION SIZE: 163
PRODUCT SIZE: 136, PAIR ANY COMPL: 4.00, PAIR 3' COMPL: 2.00

1 CACATAACTAATAAATTTGTAAGTATGTGCAACGGCTCACaCTTGCTTCCAGAATGGCAC
         >>>>>>>>>>>>>>>>>>>>>

61 CTAAAAAACAGATTTACCTCTCCCCAAATTCAGATATGGAATTAAATGTAATGTCAGGAA

121 AAcTGTCTAAGAGTTGGAAATGGGAAAAAAATGTTCTTTTGGT
            <<<<<<<<<<<<<<<<<<<<

44) Whole sequence ::: rs11088086-rs2251447
AAAAAAAAGATGAGACAGGCAGGTGCGAAAGAAATAAAAGTCAaAACTGATCCAGTTGG GAAACTCAGAATTGACAGTTAcGTGTCCTTTCATTTATTGATATTTTGAGATTCACAGGG

GT (SEQ ID NO: 131)

OLIGO start len tm gc % any
http://frodo.wi.mit.edu/cgi-bin/primer3/primer3_www_results_help.cgi - PRIMER_THREE 3' seq
(SEQ ID NOs: 132, 133)

LEFT PRIMER     6 20  56.41  45.00  2.00 2.00 AAAAGATGAGACAGGCAGGT
RIGHT PRIMER  122 20  55.99  40.00  5.00 2.00 ACCCCTGTGAATCTCAAAAT
SEQUENCE SIZE: 122
INCLUDED REGION SIZE: 122
PRODUCT SIZE: 117, PAIR ANY COMPL: 5.00, PAIR 3' COMPL: 2.00

1 AAAAAAAAGATGAGACAGGCAGGTGCGAAAGAAATAAAAGTCAaAACTGATCCAGTTGG
        >>>>>>>>>>>>>>>>>>>>

61 GAAACTCAGAATTGACAGTTAcGTGTCCTTTCATTTATTGATATTTTGAGATTCACAGGG
                     <<<<<<<<<<<<<<<<<<<<

121 GT
     <<

TABLE 2-continued

45) Whole sequence ::: rs2832040-rs11088088
GAGTTAAATAAAGCACTTGCTTCTATTGTTTGTACCTAAACTTAACAGAAcACAGTAAGT AACAAGTCATTGGGATGCAGAAAAGAAAAAAGAGAGTGAAGGAAGGAGAaAAGGTGAAGG

GAGAATGGAAGAGAGGAAGGGAGGGAGGAA (SEQ ID NO: 134)

OLIGO     start len  tm    gc %  any
http://frodo.wi.mit.edu/cgi-bin/primer3/primer3_www_results_help.cgi - PRIMER_THREE 3' seq
(SEQ ID NOs: 135, 136)

LEFT PRIMER     13 21  54.81 38.10 4.00 0.00 GCACTTGCTTCTATTGTTTGT
RIGHT PRIMER   141 20  57.37 50.00 2.00 0.00 CCCTTCCTCTCTTCCATTCT
SEQUENCE SIZE: 150
INCLUDED REGION SIZE: 150
PRODUCT SIZE: 129, PAIR ANY COMPL: 2.00, PAIR 3' COMPL: 0.00

1 GAGTTAAATAAAGCACTTGCTTCTATTGTTTGTACCTAAACTTAACAGAAcACAGTAAGT
             >>>>>>>>>>>>>>>>>>>>>

61 AACAAGTCATTGGGATGCAGAAAAGAAAAAAGAGAGTGAAGGAAGGAGAaAAGGTGAAGG

121 GAGAATGGAAGAGAGGAAGGGAGGGAGGAA
        <<<<<<<<<<<<<<<<<<<<

46) Whole sequence ::: rs2832141-rs2246777
aaacgagccaccagtgggAGCACTGCAGGTATCTGTGTGAGACCcGTACTTCACAACTCC TGCTTTCCCTCCATAAAGtAGCTTGCATTTTCCACATTGACTTTGCAGTTCTTTGGTATC

TGTATTGGT (SEQ ID NO: 137)

OLIGO     start len  tm    gc %  any
http://frodo.wi.mit.edu/cgi-bin/primer3/primer3_www_results_help.cgi - PRIMER_THREE 3' seq
(SEQ ID NOs: 138, 139)

LEFT PRIMER     14 18  58.28 61.11 6.00 2.00 gtgggAGCACTGCAGGTA
RIGHT PRIMER   123 21  55.05 38.10 4.00 2.00 ACAGATACCAAAGAACTGCAA
SEQUENCE SIZE: 129
INCLUDED REGION SIZE: 129
PRODUCT SIZE: 110, PAIR ANY COMPL: 5.00, PAIR 3' COMPL: 3.00

1 aaacgagccaccagtgggAGCACTGCAGGTATCTGTGTGAGACCcGTACTTCACAACTCC
                 >>>>>>>>>>>>>>>>>>

61 TGCTTTCCCTCCATAAAGtAGCTTGCATTTTCCACATTGACTTTGCAGTTCTTTGGTATC
                          <<<<<<<<<<<<<<<<<

121 TGTATTGGT
      <<<

47) Whole sequence ::: rs2832959-rs9980934
TGGACACCTTTCAACTTAGAAATCATAAACAGATTCATTTcCTTAAAGTTAATGaaaaga attaacagaccctcctcaaaaaagacatatatgcagcctacaatcatatgaaaaaaagtt caacattactgttcagcaaatcaaa (SEQ ID NO: 140)

OLIGO     start len  tm    gc %  any
http://frodo.wi.mit.edu/cgi-bin/primer3/primer3_www_results_help.cgi - PRIMER_THREE 3' seq
(SEQ ID NOs: 141, 142)

LEFT PRIMER      1 20  53.30 40.00 3.00 3.00 TGGACACCTTTCAACTTAGA
RIGHT PRIMER   134 22  50.67 27.27 8.00 3.00 gaacagtaatgttgaactttt
SEQUENCE SIZE: 145
INCLUDED REGION SIZE: 145
PRODUCT SIZE: 134, PAIR ANY COMPL: 7.00, PAIR 3' COMPL: 3.00

1 TGGACACCTTTCAACTTAGAAATCATAAACAGATTCATTTcCTTAAAGTTAATGaaaaga
      >>>>>>>>>>>>>>>>>>>>

61 attaacagaccctcctcaaaaaagacatatatgcagcctacaatcatatgaaaaaaagtt
                                 <<<<<<<

121 caacattactgttcagcaaatcaaa
      <<<<<<<<<<<<<<<

TABLE 2-continued

7th group
48) Whole sequence ::: rs2833734-rs2833735
TGGATACATTCCTAGAAATAGATGGAAACTGCTCTTGCAAAAAGCTTAGCACATGTTAAA aATTTTAGAAACAATTTGCCAAAGTTTATTTAGTCTAGTGATTTtGACAGGTTAAATGGA

CCCTTTGAGATCTTTTTTCCTCAAGTACAAAGGCT (SEQ ID NO: 143)

OLIGO start len tm gc % any
http://frodo.wi.mit.edu/cgi-bin/primer3/primer3_www_results_help.cgi - PRIMER_THREE 3' seq
(SEQ ID NOs: 144, 145)

LEFT PRIMER    33 21 58.90 38.10 6.00 2.00 TCTTGCAAAAAGCTTAGCACA
RIGHT PRIMER 137 21 57.77 38.10 6.00 1.00 AAAAAGATCTCAAAGGGTCCA
SEQUENCE SIZE: 155
INCLUDED REGION SIZE: 155
PRODUCT SIZE: 105, PAIR ANY COMPL: 4.00, PAIR 3' COMPL: 0.00

1 TGGATACATTCCTAGAAATAGATGGAAACTGCTCTTGCAAAAAGCTTAGCACATGTTAAA
                                    >>>>>>>>>>>>>>>>>>>>>

61 aATTTTAGAAACAATTTGCCAAAGTTTATTTAGTCTAGTGATTTtGACAGGTTAAATGGA
                                                <<<<

121 CCCTTTGAGATCTTTTTTCCTCAAGTACAAAGGCT
         <<<<<<<<<<<<<<<<<

49) Whole sequence ::: rs933121-rs933122
GCTTTTGCTGAACATCAAGTGGTGAGCCAGGACTCAAaGCCAGATCTTCTTGTTTCCCTG TTAGGTGTtTGTAGCACAACTGGTATCTGCAGACTATGCTGCTGGAAGGGCTAGCCGTC (SEQ ID NO: 146)

OLIGO start len tm gc % any
http://frodo.wi.mit.edu/cgi-bin/primer3/primer3_www_results_help.cgi - PRIMER_THREE 3' seq
(SEQ ID NOs: 147, 148)

LEFT PRIMER    1 20 55.61 40.00 6.00 3.00 GCTTTTGCTGAACATCAAGT
RIGHT PRIMER 109 19 55.56 52.63 3.00 3.00 CCTTCCAGCAGCATAGTCT
SEQUENCE SIZE: 119
INCLUDED REGION SIZE: 119
PRODUCT SIZE: 109, PAIR ANY COMPL: 5.00, PAIR 3' COMPL: 1.00

1 GCTTTTGCTGAACATCAAGTGGTGAGCCAGGACTCAAaGCCAGATCTTCTTGTTTCCCTG
      >>>>>>>>>>>>>>>>>>>>

61 TTAGGTGTtTGTAGCACAACTGGTATCTGCAGACTATGCTGCTGGAAGGGCTAGCCGTC
                                       <<<<<<<<<<<<<<<<<<<

50) Whole sequence ::: rs2834140-rs12626953
ACTGTCCTAGAAAATCCAGGATGTGCAGTGATCAtGTATGAATGCATGGACCTGCACACA

CAGGAGTGAACAAAAGACCCACCCCTGCCAGGTCACCACTCATATCTCACCCCAGCCCAC

GCTAGCTCACaCTCCTCCCCACACACCACTGACCTCATCAT (SEQ ID NO: 149)

OLIGO start len tm gc % any
http://frodo.wi.mit.edu/cgi-bin/primer3/primer3_www_results_help.cgi - PRIMER_THREE 3' seq
(SEQ ID NOs: 150, 151)

LEFT PRIMER   12 18 53.64 44.44 7.00 1.00 AAATCCAGGATGTGCAGT
RIGHT PRIMER 161 19 53.29 47.37 4.00 0.00 ATGATGAGGTCAGTGGTGT
SEQUENCE SIZE: 161
INCLUDED REGION SIZE: 161
PRODUCT SIZE: 150, PAIR ANY COMPL: 3.00, PAIR 3' COMPL: 0.00

1 ACTGTCCTAGAAAATCCAGGATGTGCAGTGATCAtGTATGAATGCATGGACCTGCACACA
                 >>>>>>>>>>>>>>>>>>

61 CAGGAGTGAACAAAAGACCCACCCCTGCCAGGTCACCACTCATATCTCACCCCAGCCCAC

121 GCTAGCTCACaCTCCTCCCCACACACCACTGACCTCATCAT
                       <<<<<<<<<<<<<<<<<<<

51) Whole sequence ::: rs2834485-rs3453
CACATCACAGATCATAGTAAATGGCTTTAATTTTTTAaCGAAATCTCACTACTGCAAATG CATTGTTGTCCTAGCTAATGAATGCAtAGAGTATTGCCTGCAAAATAATAATTGAGATTC

TATT (SEQ ID NO: 152)

TABLE 2-continued

```
OLIGO start len tm gc % any
http://frodo.wi.mit.edu/cgi-bin/primer3/primer3_www_results_help.cgi - PRIMER_THREE 3' seq
(SEQ ID NOs: 153, 154)

LEFT PRIMER     3 22 52.35 36.36 4.00 0.00 CATCACAGATCATAGTAAATGG
RIGHT PRIMER  113 21 53.50 23.81 6.00 4.00 AATTATTATTTTGCAGGCAAT
SEQUENCE SIZE: 124
INCLUDED REGION SIZE: 124
PRODUCT SIZE: 111, PAIR ANY COMPL: 5.00, PAIR 3' COMPL: 2.00

1 CACATCACAGATCATAGTAAATGGCTTTAATTTTTTAaCGAAATCTCACTACTGCAAATG
       >>>>>>>>>>>>>>>>>>>>>>

61 CATTGTTGTCCTAGCTAATGAATGCAtAGAGTATTGCCTGCAAAATAATAATTGAGATTC
                   <<<<<<<<<<<<<<<<<<<<<

121 TATT

8th group
52) Whole sequence ::: rs9974986-rs2834703
TTATCCTCCACATCCTCATGAGGCAAACACCTTTCCTACCTTACCGCTCCcCAGTGGCCT CCCTGTTGCCTTCTTATTCAAGACTAAGACtCTCTAGAATGTTCTTTATCCTGAGTCCAG

CTGATTGTCTATACTAATATCAGTACGGGGT (SEQ ID NO: 155)

OLIGO start len tm gc % any
http://frodo.wi.mit.edu/cgi-bin/primer3/primer3_www_results_help.cgi - PRIMER_THREE 3' seq
(SEQ ID NOs: 156, 157)

LEFT PRIMER    17 20 60.50 50.00 4.00 2.00 CATGAGGCAAACACCTTTCC
RIGHT PRIMER  121 22 58.46 45.45 3.00 0.00 GCTGGACTCAGGATAAAGAACA
SEQUENCE SIZE: 151
INCLUDED REGION SIZE: 151
PRODUCT SIZE: 105, PAIR ANY COMPL: 4.00, PAIR 3' COMPL: 1.00

1 TTATCCTCCACATCCTCATGAGGCAAACACCTTTCCTACCTTACCGCTCCcCAGTGGCCT
                     >>>>>>>>>>>>>>>>>>>>

61 CCCTGTTGCCTTCTTATTCAAGACTAAGACtCTCTAGAATGTTCTTTATCCTGAGTCCAG
                       <<<<<<<<<<<<<<<<<<<<

121 CTGATTGTCTATACTAATATCAGTACGGGGT
        <

53) Whole sequence ::: rs12482353-rs2205032
ATCACCTGGTTTGGTGCATCCTCGCAGAAAGAGAGCCATACAGTGAAGTGGAAACACACCCAAAAGC TCTGCAATATTCCTAGAAGTTCTCGAATCTCCTCCTTAAcAGAGCTGCAGAAGGGAAACACAGACAGG AAGCACCTGTTTGACTCAgACAGCAGCCCTAATGCAGTGCCACTCAGGAGCATTCCCTCATTTGAAG

ACCCCCCAATTACATGAAATTATCAACCCC (SEQ ID NO: 346)

OLIGO start len tm gc % any
http://frodo.wi.mit.edu/cgi-bin/primer3/primer3_www_results_help.cgi - PRIMER_THREE 3' seq
(SEQ ID NOs: 347, 348)

LEFT PRIMER    56 20 59.74 45.00 4.00 2.00 ACACCCAAAAGCTCTGCAAT
RIGHT PRIMER  199 20 60.59 50.00 4.00 2.00 CAAATGAGGGAATGCTCCTG
SEQUENCE SIZE: 232
INCLUDED REGION SIZE: 232
PRODUCT SIZE: 144, PAIR ANY COMPL: 3.00, PAIR 3' COMPL: 0.00

1 ATCACCTGGTTTGGTGCATCCTCGCAGAAAGAGAGCCATACAGTGAAGTGGAAACACACC
                                                        >>>>>

61 CAAAAGCTCTGCAATATTCCTAGAAGTTCTCGAATCTCCTCCTTAAcAGAGCTGCAGAAG
         >>>>>>>>>>>>>>>

121 GGAAACACAGACAGGAAGCACCTGTTTGACTCAgACAGCAGCCCTAATGCAGTGCCACTC
                                    <

181 AGGAGCATTCCCTCATTTGAAGACCCCCCAATTACATGAAATTATCAACCCC
        <<<<<<<<<<<<<<<<<<<<
```

TABLE 2-continued

54) Whole sequence ::: rs2776266-rs2835001
agggtgcagcactttattatggaagcctgagctgactaatacaGGTGTCTcTATATCTCA CTGAGGGAAAGTGACAGGAAAGTAAGAACCATTTaTGTCCAAGAGTCCAGAGGAGTCAAC

CAGATTCTGGGGGAAAAGAAGGTAC (SEQ ID NO: 158)

OLIGO start len tm gc % any
http://frodo.wi.mit.edu/cgi-bin/primer3/primer3_www_results_help.cgi - PRIMER_THREE 3' seq
(SEQ ID NOs: 159, 160)

LEFT PRIMER    20 20  58.75  50.00  4.00 1.00 tggaagcctgagctgactaa
RIGHT PRIMER  142 20  59.87  50.00  4.00 3.00 CCTTCTTTTCCCCCAGAATC
SEQUENCE SIZE: 145
INCLUDED REGION SIZE: 145
PRODUCT SIZE: 123, PAIR ANY COMPL: 4.00, PAIR 3' COMPL: 0.00

```
  1 agggtgcagcactttattatggaagcctgagctgactaatacaGGTGTCTcTATATCTCA
                         >>>>>>>>>>>>>>>>>>>>

61 CTGAGGGAAAGTGACAGGAAAGTAAGAACCATTTaTGTCCAAGAGTCCAGAGGAGTCAAC

121 CAGATTCTGGGGGAAAAGAAGGTAC
       <<<<<<<<<<<<<<<<<<<<
```

55) Whole sequence ::: rs1984014-rs1984015
TGAGAAT TTAGGAGAACAGAAGATCAGAGGGCTGCACaGGCTAAACTAGACAATGAGCCC ATGCAAGTAAGTTAAGAGGAGAAGCGGGTAAGTATGCACCTGCTTTGTCTAGGtGACCAG

CAAGCATTTAGCAATAGTCTTT TCAAAACAACAG (SEQ ID NO: 161)

OLIGO start len tm gc % any
http://frodo.wi.mit.edu/cgi-bin/primer3/primer3_www_results_help.cgi - PRIMER_THREE 3' seq
(SEQ ID NOs: 162, 163)

LEFT PRIMER     8 22  53.09  40.91  4.00 1.00 TTAGGAGAACAGAAGATCAGAG
RIGHT PRIMER  142 22  53.52  31.82  4.00 2.00 AAAGACTATTGCTAAATGCTTG
SEQUENCE SIZE: 154
INCLUDED REGION SIZE: 154
PRODUCT SIZE: 135, PAIR ANY COMPL: 4.00, PAIR 3' COMPL: 2.00

```
  1 TGAGAATTTAGGAGAACAGAAGATCAGAGGGCTGCACaGGCTAAACTAGACAATGAGCCC
            >>>>>>>>>>>>>>>>>>>>>>

61 ATGCAAGTAAGTTAAGAGGAGAAGCGGGTAAGTATGCACCTGCTTTGTCTAGGtGACCAG

121 CAAGCATTTAGCAATAGTCTTTTCAAAACAACAG
       <<<<<<<<<<<<<<<<<<<<<<
```

56) Whole sequence ::: rs1014593-rs9305569
GGAACTGCAGGAGATCCCTGCTGCCTTCCAGTTCATGGGATGATGGCCTCCACTTCTGCCCCTGTTT GCTTCTCCTTTTCAaATCTTACATGAAGGTATACAGTTTGAAGAAGCCAGTTTGACTCCAATATCTGTGC AATGGAATACTGCTCATTAAAAAGgAATTAAACTATTGATACACACAACATGGGTGAAGATCAAACTGT

CTCCTTCCCTTTGATTCAAGGGAATCTGAGAAATG (SEQ ID NO: 349)

OLIGO start len tm gc % any
http://frodo.wi.mit.edu/cgi-bin/primer3/primer3_www_results_help.cgi - PRIMER_THREE 3' seq
(SEQ ID NOs: 350, 351)

LEFT PRIMER    51 19  59.86  52.63  2.00 0.00 ACTTCTGCCCCTGTTTGCT
RIGHT PRIMER  198 21  58.84  42.86  4.00 3.00 TGATCTTCACCCATGTTGTGT
SEQUENCE SIZE: 239
INCLUDED REGION SIZE: 239
PRODUCT SIZE: 148, PAIR ANY COMPL: 2.00, PAIR 3' COMPL: 0.00

```
  1 GAACTGCAGGAGATCCCTGCTGCCTTCCAGTTCATGGGATGATGGCCTCCACTTCTGCCC
                                                       >>>>>>>>>

61 CTGTTTGCTTCTCCTTTTCAaATCTTACATGAAGGTATACAGTTTGAAGAAGCCAGTTTGA
       >>>>>>>>>

121 CTCCAATATCTGTGCAATGGAATACTGCTCATTAAAAAGgAATTAAACTATTGATACACA
                                         <<<

181 CAACATGGGTGAAGATCAAACTGTCTCCTTCCCTTTGATTCAAGGGAATCTGAGAAATG
       <<<<<<<<<<<<<<<<<<<<
```

TABLE 2-continued

57) Whole sequence ::: rs7281674-rs2835316
AAACAGGCAAAATAAGCGTAGGGCTGTGTGTGCAACAGTTaATCATAAAGCCATCACCAG GAGACgTCACTGGGCGCCTTCTGGAGTCTATCCGTCCTAACTTTGC (SEQ ID NO: 164)

OLIGO start len tm gc % any
http://frodo.wi.mit.edu/cgi-bin/primer3/primer3_www_results_help.cgi - PRIMER_THREE 3' seq
(SEQ ID NOs: 165, 166)

LEFT PRIMER    13 20  59.93  55.00  4.00  0.00 TAAGCGTAGGGCTGTGTGTG
RIGHT PRIMER   97 21  60.08  57.14  3.00  1.00 GGACGGATAGACTCCAGAAGG
SEQUENCE SIZE: 106
INCLUDED REGION SIZE: 106
PRODUCT SIZE: 85, PAIR ANY COMPL: 3.00, PAIR 3' COMPL: 0.00

1 AAACAGGCAAAATAAGCGTAGGGCTGTGTGTGCAACAGTTaATCATAAAGCCATCACCAG
                 >>>>>>>>>>>>>>>>>>>>

61 GAGACgTCACTGGGCGCCTTCTGGAGTCTATCCGTCCTAACTTTGC
                         <<<<<<<<<<<<<<<<<<<<<

58) Whole sequence ::: rs13047304-rs13047322
gaatgaccttggcactttttatcaaacatcaactggccacaCacaggtgagtctacttctg gacacttaTcctgttccattcatctgtatatctctatccttacac (SEQ ID NO: 167)

OLIGO start len tm gc % any
http://frodo.wi.mit.edu/cgi-bin/primer3/primer3_www_results_help.cgi - PRIMER_THREE 3' seq
(SEQ ID NOs: 168, 169)

LEFT PRIMER     1 23  60.36  39.13  3.00  2.00 gaatgaccttggcactttttatca
RIGHT PRIMER  101 27  57.86  33.33  4.00  0.00 aaggatagagatatacagatgaatgga
SEQUENCE SIZE: 105
INCLUDED REGION SIZE: 105
PRODUCT SIZE: 101, PAIR ANY COMPL: 4.00, PAIR 3' COMPL: 1.00

1 gaatgaccttggcactttttatcaaacatcaactggccacaCacaggtgagtctacttctg
     >>>>>>>>>>>>>>>>>>>>>>>

61 gacacttaTcctgttccattcatctgtatatctctatccttacac
                     <<<<<<<<<<<<<<<<<<<<<<<<<<<

59) Whole sequence ::: rs2835545-rs4816551
CTGCTGGAATAGGCTGCTTGGCCATGTTCTTGGAAGCTACCACCATATCAaGGTAATTTC CCACACAACATTCCAGCCCCTGCTTTCCtCTCTGGCCTTATCTAGGGCCATTCCCCAACT

CAGGTGAAT (SEQ ID NO: 170)

OLIGO start len tm gc % any
http://frodo.wi.mit.edu/cgi-bin/primer3/primer3_www_results_help.cgi - PRIMER_THREE 3' seq
(SEQ ID NOs: 171, 172)

LEFT PRIMER    20 20  60.21  50.00  4.00  2.00 GGCCATGTTCTTGGAAGCTA
RIGHT PRIMER  128 20  60.89  50.00  5.00  0.00 TTCACCTGAGTTGGGGAATG
SEQUENCE SIZE: 129
INCLUDED REGION SIZE: 129
PRODUCT SIZE: 109, PAIR ANY COMPL: 3.00, PAIR 3' COMPL: 0.00

1 CTGCTGGAATAGGCTGCTTGGCCATGTTCTTGGAAGCTACCACCATATCAaGGTAATTTC
                        >>>>>>>>>>>>>>>>>>>>

61 CCACACAACATTCCAGCCCCTGCTTTCCtCTCTGGCCTTATCTAGGGCCATTCCCCAACT
                                   <<<<<<<<<<<

121 CAGGTGAAT
     <<<<<<<<<

60) Whole sequence ::: rs2835735-rs2835736
ACCTTTGTTCCATGCACCGCGCAAATACCTGGGAACCCTTaTTGCCCAACTCAAGAGCCA GAGTCCTCTGTCATCATTTTGCCTCTCTCCTAAGTGAgAGGACTGAGTGCAGACTTGGTG

TTTGTGGGTGAGGCATGT (SEQ ID NO: 173)

TABLE 2-continued

```
OLIGO            start len    tm   gc %  any
http://frodo.wi.mit.edu/cgi-bin/primer3/primer3_www_results_help.cgi - PRIMER_THREE 3' seq
(SEQ ID NOs: 174, 175)

LEFT PRIMER     11 18  62.22  55.56  5.00 0.00 CATGCACCGCGCAAATAC
RIGHT PRIMER   136 19  59.38  52.63  2.00 0.00 ATGCCTCACCCACAAACAC
SEQUENCE SIZE: 138
INCLUDED REGION SIZE: 138
PRODUCT SIZE: 126, PAIR ANY COMPL: 3.00, PAIR 3' COMPL: 0.00

1 ACCTTTGTTCCATGCACCGCGCAAATACCTGGGAACCCTTaTTGCCCAACTCAAGAGCCA
                >>>>>>>>>>>>>>>>>>

61 GAGTCCTCTGTCATCATTTTGCCTCTCTCCTAAGTGAgAGGACTGAGTGCAGACTTGGTG
                                                      <<<

121 TTTGTGGGTGAGGCATGT
     <<<<<<<<<<<<<<<<<<

61) Whole sequence ::: rs13047608-rs2835826
CTCCTGAGTCCAAGCCCTTCTCACTCACCTCTTTCTTGAACTAATTTCTTcCTGTTTTTT TCCAGTCCTCCCTTCTGTTCATGTCTCTCCTCTGCACACTTCCATTTTgTGGTTCAGAAA

ATGTCACCGTCCCAG TCACACTTGCCTTATGGCTGTTGT (SEQ ID NO: 176)

OLIGO            start len    tm   gc %  any
http://frodo.wi.mit.edu/cgi-bin/primer3/primer3_www_results_help.cgi - PRIMER_THREE 3' seq
(SEQ ID NOs: 177, 178)

LEFT PRIMER     9 20  60.39  55.00  4.00 0.00 TCCAAGCCCTTCTCACTCAC
RIGHT PRIMER  135 20  59.97  50.00  3.00 1.00 CTGGGACGGTGACATTTTCT
SEQUENCE SIZE: 159
INCLUDED REGION SIZE: 159
PRODUCT SIZE: 127, PAIR ANY COMPL: 4.00, PAIR 3' COMPL: 0.00

1 CTCCTGAGTCCAAGCCCTTCTCACTCACCTCTTTCTTGAACTAATTTCTTcCTGTTTTTT
              >>>>>>>>>>>>>>>>>>>>

61 TCCAGTCCTCCCTTCTGTTCATGTCTCTCCTCTGCACACTTCCATTTTgTGGTTCAGAAA
                                                     <<<<<

121 ATGTCACCGTCCCAGTCACACTTGCCTTATGGCTGTTGT
        <<<<<<<<<<<<<<<

62) Whole sequence ::: rs857998-rs17284497
TGGAGAAAGTTGTTGCAAACTGCCCAGAGACCCTGGGAGTCACTCCAGTTTTCTGAAACCCAGATAT TTCAGtGCCTCAGGAGAGACAAGTCCTGACCTTCTCTCCTCCAGCTCTCCCAGgAGATAGGCAAGCC

CCTAACTCCCTAACTAAGCCCTTCAGACCTGAAATCCATTGAGTGGCTTCTTT (SEQ ID NO: 352)

OLIGO            start len    tm   gc %  any
http://frodo.wi.mit.edu/cgi-bin/primer3/primer3_www_results_help.cgi - PRIMER_THREE 3' seq
(SEQ ID NOs: 353, 354)

LEFT PRIMER     15 18  59.35  61.11  4.00 0.00 GCAAACTGCCCAGAGACC
RIGHT PRIMER   147 20  60.57  55.00  2.00 2.00 TTAGGGAGTTAGGGGCTTGC
SEQUENCE SIZE: 189
INCLUDED REGION SIZE: 189
PRODUCT SIZE: 133, PAIR ANY COMPL: 5.00, PAIR 3' COMPL: 2.00

1 TGGAGAAAGTTGTTGCAAACTGCCCAGAGACCCTGGGAGTCACTCCAGTTTTCTGAAACC
                    >>>>>>>>>>>>>>>>>>

61 CAGATATTTCAGtGCCTCAGGAGAGACAAGTCCTGACCTTCTCTCCTCCAGCTCTCCCAG 121 gAGATAGGCAAGCCCCTAACTCCCTAACTAAGCCCTTCAGACCTGAAATCCATTGAGTGG
              <<<<<<<<<<<<<<<<<<<<

181 CTTCTTTAC

9th group
63) Whole sequence ::: rs2836550-rs2212596
CCCAGGAAGAGTGGAAAGATTAACCTTTGTGAGCCAAACCaGTGACACTTGATTACTTGA CAGAACTAATCCTTCTGTCCTGATGACAGAAcTTCAACTACACAGGTACATGCAAGCTAA

TATCTGTTGTAA (SEQ ID NO: 179)
```

TABLE 2-continued

```
OLIGO            start len    tm   gc %  any
http://frodo.wi.mit.edu/cgi-bin/primer3/primer3_www_results_help.cgi - PRIMER_THREE 3' seq
(SEQ ID NOs: 180, 181)

LEFT PRIMER       1  21  59.56  47.62  3.00  2.00 CCCAGGAAGAGTGGAAAGATT
RIGHT PRIMER    120  21  56.03  42.86  6.00  1.00 TTAGCTTGCATGTACCTGTGT
SEQUENCE SIZE: 132
INCLUDED REGION SIZE: 132
PRODUCT SIZE: 120, PAIR ANY COMPL: 5.00, PAIR 3' COMPL: 3.00

1 CCCAGGAAGAGTGGAAAGATTAACCTTTGTGAGCCAAACCaGTGACACTTGATTACTTGA
      >>>>>>>>>>>>>>>>>>>>>

61 CAGAACTAATCCTTCTGTCCTGATGACAGAAcTTCAACTACACAGGTACATGCAAGCTAA
                         <<<<<<<<<<<<<<<<<<<<<

121 TATCTGTTGTAA

64) Whole sequence ::: rs2836660-rs2836661
GCCTGGCAAGCTAGATGGGGTGAATTTTCACCTGCCACAGcCGCAAGTCAAAGCCACCGG

CTTCTCTCTTCTCCCTCCCATTGCTCCTGACAGCCAGGGTTAATATTTTGCCTCATGTAA

ACAGGGAGGCAtCCACCCGAGAATCTCCCCTCAGCCCACATAAGC (SEQ ID NO: 182)

OLIGO            start len    tm   gc %  any
http://frodo.wi.mit.edu/cgi-bin/primer3/primer3_www_results_help.cgi - PRIMER_THREE 3' seq
(SEQ ID NOs: 183, 184)

LEFT PRIMER       9  20  55.41  40.00  4.00  2.00 AGCTAGATGGGGTGAATTTT
RIGHT PRIMER    158  18  61.14  61.11  3.00  3.00 TGGGCTGAGGGGAGATTC
SEQUENCE SIZE: 165
INCLUDED REGION SIZE: 165
PRODUCT SIZE: 150, PAIR ANY COMPL: 4.00, PAIR 3' COMPL: 3.00

1 GCCTGGCAAGCTAGATGGGGTGAATTTTCACCTGCCACAGcCGCAAGTCAAAGCCACCGG
              >>>>>>>>>>>>>>>>>>>>

61 CTTCTCTCTTCTCCCTCCCATTGCTCCTGACAGCCAGGGTTAATATTTTGCCTCATGTAA

121 ACAGGGAGGCAtCCACCCGAGAATCTCCCCTCAGCCCACATAAGC
                  <<<<<<<<<<<<<<<<<<

65) Whole sequence ::: rs465612-rs8131220
atcaagctaattaatgttatctatcacttcAcatagttcaaccttttttgtggtgagag tactgaagatctactctcttagcaattttcaaatctaaaatacattattattaacacagt cactgtgccGtacgttagctctgaggaccttattcatttt (SEQ ID NO: 185)

OLIGO            start len    tm   gc %  any
http://frodo.wi.mit.edu/cgi-bin/primer3/primer3_www_results_help.cgi - PRIMER_THREE 3' seq
(SEQ ID NOs: 186, 187)

LEFT PRIMER       1  22  47.51  22.73  6.00  4.00 atcaagctaattaatgttatct
RIGHT PRIMER    158  20  50.92  40.00  5.00  5.00 aatgaataaggtcctcagag
SEQUENCE SIZE: 160
INCLUDED REGION SIZE: 160
PRODUCT SIZE: 158, PAIR ANY COMPL: 5.00, PAIR 3' COMPL: 2.00

1 atcaagctaattaatgttatctatcacttcAcatagttcaaccttttttgtggtgagag
      >>>>>>>>>>>>>>>>>>>>>>

61 tactgaagatctactctcttagcaattttcaaatctaaaatacattattattaacacagt 121 cactgtgccGtacgttagctctgaggaccttattcatttt
                       <<<<<<<<<<<<<<<<<<<<

66) Whole sequence ::: rs9980072-rs8130031
TTTAATCTGATCATTGCCCTATGAGGTAGGgAGTATTCTGATTCCCATTTTATAAATAAG GAACCCGAGGCTTAGAGAGCATCaGTGACTTGTTCAAGGTCACCCACAGCTGTCAAGTGA

CAGA (SEQ ID NO: 188)
```

TABLE 2-continued

```
OLIGO            start len   tm    gc %  any
http://frodo.wi.mit.edu/cgi-bin/primer3/primer3_www_results_help.cgi - PRIMER_THREE 3' seq
(SEQ ID NOs: 189, 190)

LEFT PRIMER       1  21  55.02  33.33  6.00  2.00 TTTAATCTGATCATTGCCCTA
RIGHT PRIMER    111  18  57.61  55.56  5.00  1.00 AGCTGTGGGTGACCTTGA
SEQUENCE SIZE: 124
INCLUDED REGION SIZE: 124
PRODUCT SIZE: 111, PAIR ANY COMPL: 3.00, PAIR 3' COMPL: 1.00

1TTTAATCTGATCATTGCCCTATGAGGTAGGgAGTATTCTGATTCCCATTTTATAAATAAG
    >>>>>>>>>>>>>>>>>>>>>

61GAACCCGAGGCTTAGAGAGCATCaGTGACTTGTTCAAGGTCACCCACAGCTGTCAAGTGA
                   <<<<<<<<<<<<<<<<<<

121CAGA
```

10<sup>th</sup> group
67) Whole sequence ::: rs418359-rs2836926
tgtcccaccattgtgtattaggtttgtagagCgtagacaacttgccttttttagtttgtag gtttctgtatcaagagaagatgtgtgtGggcctaacctagattacaggatcctggacttc aagtctga (SEQ ID NO: 191)

```
OLIGO            start len   tm    gc %  any
http://frodo.wi.mit.edu/cgi-bin/primer3/primer3_www_results_help.cgi - PRIMER_THREE 3' seq
(SEQ ID NOs: 192, 193)

LEFT PRIMER       1  20  54.64  40.00  6.00  3.00 tgtcccaccattgtgtatta
RIGHT PRIMER    128  20  54.70  45.00  9.00  3.00 tcagacttgaagtccaggat
SEQUENCE SIZE: 128
INCLUDED REGION SIZE: 128
PRODUCT SIZE: 128, PAIR ANY COMPL: 3.00, PAIR 3' COMPL: 1.00

1tgtcccaccattgtgtattaggtttgtagagCgtagacaacttgccttttttagtttgtag
    >>>>>>>>>>>>>>>>>>>>

61gtttctgtatcaagagaagatgtgtgtGggcctaacctagattacaggatcctggacttc
                        <<<<<<<<<<

121aagtctga
    <<<<<<<
```

68) Whole sequence ::: rs11701943-rs4816634
tcatttgctaaggtcggatagctcctaattggcaaagtcaCgatgggatcccagggattc tgaggatgaagcctgtgtttaataactAttatgccaAGTGAGCATTTTCAAATATATGAG

AGAAATTA (SEQ ID NO: 194)

```
OLIGO            start len   tm    gc %  any
http://frodo.wi.mit.edu/cgi-bin/primer3/primer3_www_results_help.cgi - PRIMER_THREE 3' seq
(SEQ ID NOs: 195, 196)

LEFT PRIMER       2  19  53.86  42.11  4.00  2.00 catttgctaaggtcggata
RIGHT PRIMER    114  20  51.56  30.00  6.00  2.00 TATTTGAAAATGCTCACTtg
SEQUENCE SIZE: 128
INCLUDED REGION SIZE: 128
PRODUCT SIZE: 113, PAIR ANY COMPL: 6.00, PAIR 3' COMPL: 0.00

1tcatttgctaaggtcggatagctcctaattggcaaagtcaCgatgggatcccagggattc
    >>>>>>>>>>>>>>>>>>>

61tgaggatgaagcctgtgtttaataactAttatgccaAGTGAGCATTTTCAAATATATGAG
                      <<<<<<<<<<<<<<<<<<<<

121AGAAATTA
```

69) Whole sequence ::: rs7278447-rs7278858
CATTGCTTCAGGGGTGTTAGTTTTGTGTTCaCAACTAGATTATAAACTCCTCTTGCATTC CTGATGGCAGTGACTTGAAGGCAtttatttgaagaataatagacatacagaaaggggcac atgtcataaaggtacagctggacgacttttcacaaagtg (SEQ ID NO: 197)

TABLE 2-continued

```
OLIGO start len tm gc % any
http://frodo.wi.mit.edu/cgi-bin/primer3/primer3_www_results_help.cgi - PRIMER_THREE 3' seq
(SEQ ID NOs: 198, 199)

LEFT PRIMER      5 20  55.96  45.00  2.00  0.00 GCTTCAGGGGTGTTAGTTTT
RIGHT PRIMER   157 20  55.97  45.00  5.00  1.00 ctttgtgaaaagtcgtccag
SEQUENCE SIZE: 159
INCLUDED REGION SIZE: 159
PRODUCT SIZE: 153, PAIR ANY COMPL: 4.00, PAIR 3' COMPL: 0.00

1 CATTGCTTCAGGGGTGTTAGTTTTGTGTTCaCAACTAGATTATAAACTCCTCTTGCATTC
      >>>>>>>>>>>>>>>>>>>>

61 CTGATGGCAGTGACTTGAAGGCAttttatttgaagaataatagacatacagaaaggggcac 121 atgtcataaaggtacagctggacgacttttcacaaagtg
               <<<<<<<<<<<<<<<<<<<<

70) Whole sequence :::  rs385787-rs367001
GAGAGGATGGTGCCATCATGGAAAGCATGGGGCAGTCATGGAGATGACGGaGTAGCTCAT GGAGAAgATAATGCCATCATGGAAGGCATAGTGCAGTCATGGAGATGATGGTGCAGC (SEQ ID NO: 200)

OLIGO start len tm gc % any
http://frodo.wi.mit.edu/cgi-bin/primer3/primer3_www_results_help.cgi - PRIMER_THREE 3' seq
(SEQ ID NOs: 201, 202)

LEFT PRIMER    13 18  58.34  50.00  7.00  3.00 CCATCATGGAAAGCATGG
RIGHT PRIMER  108 20  55.09  45.00  4.00  2.00 TCATCTCCATGACTGCACTA
SEQUENCE SIZE: 117
INCLUDED REGION SIZE: 117
PRODUCT SIZE: 96, PAIR ANY COMPL: 7.00, PAIR 3' COMPL: 3.00

1 GAGAGGATGGTGCCATCATGGAAAGCATGGGGCAGTCATGGAGATGACGGaGTAGCTCAT
            >>>>>>>>>>>>>>>>>>

61 GGAGAAgATAATGCCATCATGGAAGGCATAGTGCAGTCATGGAGATGATGGTGCAGC
                 <<<<<<<<<<<<<<<<<<<<

71) Whole sequence :::  rs367001-rs386095
ATGGGGCAGTCATGGAGATGACGGAGTAGCTCATGGAGAAaATAATGCCATCATGGAAGG CATAGTGCAGTCATGGAGATGATGGTGCAGCTCATGGAGAAGATGGTGCCATCATGgAAG GCATGGTGCAATCATGGAGTAGACAGTGCAGCTGGGCCaagattctc (SEQ ID NO: 203)

OLIGO start len tm gc % any
http://frodo.wi.mit.edu/cgi-bin/primer3/primer3_www_results_help.cgi - PRIMER_THREE 3' seq
(SEQ ID NOs: 204, 205)

LEFT PRIMER    15 20  54.39  50.00  4.00  3.00 GAGATGACGGAGTAGCTCAT
RIGHT PRIMER  156 18  55.17  61.11  6.00  2.00 CCCAGCTGCACTGTCTAC
SEQUENCE SIZE: 167
INCLUDED REGION SIZE: 167
PRODUCT SIZE: 142, PAIR ANY COMPL: 6.00, PAIR 3' COMPL: 2.00

1 ATGGGGCAGTCATGGAGATGACGGAGTAGCTCATGGAGAAaATAATGCCATCATGGAAGG
              >>>>>>>>>>>>>>>>>>>>

61 CATAGTGCAGTCATGGAGATGATGGTGCAGCTCATGGAGAAGATGGTGCCATCATGgAAG

121 GCATGGTGCAATCATGGAGTAGACAGTGCAGCTGGGCCaagattctc
               <<<<<<<<<<<<<<<<<<

72) Whole sequence :::  rs2837296-rs2837297
GATGTGCCTCTCTTGTTCCAATCACAGGACAGGGGTATAAcTAGGGGCACTGTCTATACT GGCTGCACTCTGGCCAGTGCTGTCCCAgGTAGATTCATCAGGGTCTAGAGCTTCAGCTAA

CAGCATGA (SEQ ID NO: 206)

OLIGO start len tm gc % any
http://frodo.wi.mit.edu/cgi-bin/primer3/primer3_www_results_help.cgi - PRIMER_THREE 3' seq
(SEQ ID NOs: 207, 208)

LEFT PRIMER    11 20  56.00  45.00  4.00  1.00 TCTTGTTCCAATCACAGGAC
RIGHT PRIMER  126 20  54.59  45.00  6.00  3.00 ATGCTGTTAGCTGAAGCTCT
SEQUENCE SIZE: 128
INCLUDED REGION SIZE: 128
PRODUCT SIZE: 116, PAIR ANY COMPL: 4.00, PAIR 3' COMPL: 1.00
```

TABLE 2-continued

```
  1 GATGTGCCTCTCTTGTTCCAATCACAGGACAGGGGTATAAcTAGGGGCACTGTCTATACT
       >>>>>>>>>>>>>>>>>>>>

61 GGCTGCACTCTGGCCAGTGCTGTCCCAgTAGATTCATCAGGGTCTAGAGCTTCAGCTAA
               <<<<<<<<<<<<<

121 CAGCATGA
    <<<<<
```

73) Whole sequence ::: rs4239808-rs2410205
AGGGCCATGGGATGATGCAGGTGGAGACTGGAGTGCTACAGCTGCAAGCAAATACATTTCTGTGCT GTGAAGCCAcCCATTTGGTGGTACTACGTTAAAACAGCTCTAGGAAATTAAtACAGATGTTGCCTGTAT

TTTTGTTTCTCATATTACTACTCATTGTTTTAATGATGACTGTTTTATT (SEQ ID NO: 355)

OLIGO            start  len  tm    gc %   any
http://frodo.wi.mit.edu/cgi-bin/primer3/primer3_www_results_help.cgi - PRIMER_THREE 3' seq
(SEQ ID NOs: 356, 357)

LEFT PRIMER      19  20  57.45  55.00  4.00  2.00 AGGTGGAGACTGGAGTGCTA
RIGHT PRIMER    145  22  56.58  31.82  2.00  0.00 AGAAACAAAAATACAGGCAACA
SEQUENCE SIZE: 184
INCLUDED REGION SIZE: 184
PRODUCT SIZE: 127, PAIR ANY COMPL: 3.00, PAIR 3' COMPL: 1.00

```
  1 AGGGCCATGGGATGATGCAGGTGGAGACTGGAGTGCTACAGCTGCAAGCAAATACATTTC
          >>>>>>>>>>>>>>>>>>>>

61 TGTGCTGTGAAGCCAcCCATTTGGTGGTACTACGTTAAAACAGCTCTAGGAAATTAAtAC

121 AGATGTTGCCTGTATTTTTGTTTCTCATATTACTACTCATTGTTTTAATGATGACTGTTT
        <<<<<<<<<<<<<<<<<<<<<<

181 TATT
```

74) Whole sequence ::: rs2837381-rs4816672
TTTTATTCATTAAGTTGAAAGCTCCTAAAGCAGAGGGACCaTATTTTTATGTCCCAACTC TCCTTAAGgCCTTGCCTATGATAGCACATCTCTTCAATAGAATTGTCCT (SEQ ID NO: 209)

OLIGO            start  len  tm    gc %   any
http://frodo.wi.mit.edu/cgi-bin/primer3/primer3_www_results_help.cgi - PRIMER_THREE 3' seq
(SEQ ID NOs: 210, 211)

LEFT PRIMER      16  20  55.17  45.00  4.00  0.00 TGAAAGCTCCTAAAGCAGAG
RIGHT PRIMER     97  20  50.59  35.00  4.00  3.00 TTGAAGAGATGTGCTATCAT
SEQUENCE SIZE: 109
INCLUDED REGION SIZE: 109
PRODUCT SIZE: 82, PAIR ANY COMPL: 5.00, PAIR 3' COMPL: 1.00

```
  1 TTTTATTCATTAAGTTGAAAGCTCCTAAAGCAGAGGGACCaTATTTTTATGTCCCAACTC
            >>>>>>>>>>>>>>>>>>>>

61 TCCTTAAGgCCTTGCCTATGATAGCACATCTCTTCAATAGAATTGTCCT
              <<<<<<<<<<<<<<<<<<<<
```

11 th group
75) Whole sequence ::: rs13047873-rs2837697
AAAGACCAGCTTTTAGCTGAACATCAGGGCTGCCTTCAGAGTTTAATTACCGCCCTCCCC ATGGGGCCAAATGAGCCATCGACTCCTCCCAAGGGGGTTCgGCTTGGTACTGATCTTTAA GTAAGTaAACGCTAAACCAGCTCATCTTAAAGCGCCCACATCTGATTTCCTGCTCTGCTG

CAAGACAGTAGGTGACTGGTAATGACC (SEQ ID NO: 214)

OLIGO            start  len  tm    gc %   any
http://frodo.wi.mit.edu/cgi-bin/primer3/primer3_www_results_help.cgi - PRIMER_THREE 3' seq
(SEQ ID NOs: 215, 216)

LEFT PRIMER      26  20  59.08  50.00  5.00  2.00 AGGGCTGCCTTCAGAGTTTA
RIGHT PRIMER    155  20  59.62  50.00  5.00  2.00 GCGCTTTAAGATGAGCTGGT
SEQUENCE SIZE: 207
INCLUDED REGION SIZE: 207
PRODUCT SIZE: 130, PAIR ANY COMPL: 3.00, PAIR 3' COMPL: 1.00

TABLE 2-continued

```
  1 AAAGACCAGCTTTTAGCTGAACATCAGGGCTGCCTTCAGAGTTTAATTACCGCCCTCCCC
             >>>>>>>>>>>>>>>>>>>>

61 ATGGGGCCAAATGAGCCATCGACTCCTCCCAAGGGGTTCgGCTTGGTACTGATCTTTAA

121 GTAAGTaAACGCTAAACCAGCTCATCTTAAAGCGCCCACATCTGATTTCCTGCTCTGCTG
             <<<<<<<<<<<<<<<<<<

181 CAAGACAGTAGGTGACTGGTAATGACC
```

76) Whole sequence ::: rs455999-rs9305700
ACTCTGCTCCCAGTGTGAACATGGGGAAAGTTGATTAAACTCTCTGACTTCAGATTCCTC aTGTAAAATGTGGGGAAACAGCTCTGACTTAATGGTGTCACTGTGAGGAGTAAATGAGGT AgCATATTTAAAGGATTTTGTATAGTGCTGGTGACAGTAACCAGCCAATAGATGATATAG

CTAGTAATAGCA (SEQ ID NO: 217)

OLIGO  start len tm gc % any
http://frodo.wi.mit.edu/cgi-bin/primer3/primer3_www_results_help.cgi - PRIMER_THREE 3' seq
(SEQ ID NOs: 218, 219)

LEFT PRIMER    16  20  57.84  40.00  4.00  2.00 TGAACATGGGGAAAGTTGAT
RIGHT PRIMER  154  22  56.81  40.91  4.00  0.00 TCACCAGCACTATACAAAATCC
SEQUENCE SIZE: 192
INCLUDED REGION SIZE: 192
PRODUCT SIZE: 139, PAIR ANY COMPL: 4.00, PAIR 3' COMPL: 2.00

```
  1 ACTCTGCTCCCAGTGTGAACATGGGGAAAGTTGATTAAACTCTCTGACTTCAGATTCCTC
             >>>>>>>>>>>>>>>>>>>>

61 aTGTAAAATGTGGGGAAACAGCTCTGACTTAATGGTGTCACTGTGAGGAGTAAATGAGGT

121 AgCATATTTAAAGGATTTTGTATAGTGCTGGTGACAGTAACCAGCCAATAGATGATATAG
             <<<<<<<<<<<<<<<<<<<<<<

181 CTAGTAATAGCA
```

77) Whole sequence ::: rs9976207-rs455473
cttcactgaccacttccttaactgtccactccgaaacaccCcttcttcctgttcttccaa tacaccaaactcttcttgcctctgtgtgcttgcccatgctgttccttctggcttcttcc ttcACATTCAAGTCTTGACTTAGATGTCACTTGCCAAGGGAGACCTTGGA (SEQ ID NO: 220)

OLIGO  start len tm gc % any
http://frodo.wi.mit.edu/cgi-bin/primer3/primer3_www_results_help.cgi - PRIMER_THREE 3' seq
(SEQ ID NOs: 221, 222)

LEFT PRIMER    12  21  54.96  47.62  4.00  0.00 acttccttaactgtccactcc
RIGHT PRIMER  159  19  54.64  47.37  7.00  2.00 CCTTGGCAAGTGACATCTA
SEQUENCE SIZE: 170
INCLUDED REGION SIZE: 170
PRODUCT SIZE: 148, PAIR ANY COMPL: 5.00, PAIR 3' COMPL: 3.00

```
  1 cttcactgaccacttccttaactgtccactccgaaacaccCcttcttcctgttcttccaa
             >>>>>>>>>>>>>>>>>>>>>

61 tacaccaaactcttcttgcctctgtgtgcttgcccatgctgttccttctggcttcttcc 121 ttcACATTCAAGTCTTGACTTAGATGTCACTTGCCAAGGGAGACCTTGGA
                      <<<<<<<<<<<<<<<<<<<
```

78) Whole sequence ::: rs2837807-rs2837808
AAACATCCCAATAGACAAAACTCCAAGAAGAGTCAAAACAAGAATAAAGTaCAGGTCATC

TTTTCTTTTGCACTCCTGACAGCACTTTGTACATGGTAATAATAATCTACCAATTAACTA

CATAAGCCACATGGTTTTATcATAGTGTGAAGCTTTGTATCCAGAAAGGAGAGAAGGCTCC (SEQ ID NO: 223)

OLIGO  start len tm gc % any
http://frodo.wi.mit.edu/cgi-bin/primer3/primer3_www_results_help.cgi - PRIMER_THREE 3' seq
(SEQ ID NOs: 224, 225)

LEFT PRIMER    23  22  56.31  36.36  3.00  0.00 CCAAGAAGAGTCAAAACAAGAA
RIGHT PRIMER  172  21  56.19  42.86  4.00  2.00 TCTCCTTTCTGGATACAAAGC
SEQUENCE SIZE: 181
INCLUDED REGION SIZE: 181
PRODUCT SIZE: 150, PAIR ANY COMPL: 5.00, PAIR 3' COMPL: 1.00

TABLE 2-continued

```
  1 AAACATCCCAATAGACAAAACTCCAAGAAGAGTCAAAACAAGAATAAAGTaCAGGTCATC
                          >>>>>>>>>>>>>>>>>>>>

61 TTTTCTTTTGCACTCCTGACAGCACTTTGTACATGGTAATAATAATCTACCAATTAACTA

121 CATAAGCCACATGGTTTTATcATAGTGTGAAGCTTTGTATCCAGAAAGGAGAGAAGGCTC
                    <<<<<<<<<<<<<<<<<<<<

181 C
```

79) Whole sequence ::: rs9974587-rs2776356
GGCAGAGGCATGGGGTGCATAGGGATATGGGGTGGGCCAGTTTGCTCCTCAGACCAGAAG GGGTGCAGGAcTCCCCCCGATCAGGATCaTGGAGAAAGGTGTGGACAGAGGAAGGGAGGG

AGGGAGAAATGGCAGCTGCCCTGCAGTGG (SEQ ID NO: 226)

OLIGO start len tm gc % any
http://frodo.wi.mit.edu/cgi-bin/primer3/primer3_www_results_help.cgi - PRIMER_THREE 3' seq
(SEQ ID NOs: 227, 228)

LEFT PRIMER    42 20 60.52 55.00 3.00 2.00 TTGCTCCTCAGACCAGAAGG
RIGHT PRIMER  118 20 59.68 60.00 4.00 2.00 CTCCCTTCCTCTGTCCACAC
SEQUENCE SIZE: 149
INCLUDED REGION SIZE: 149
PRODUCT SIZE: 77, PAIR ANY COMPL: 5.00, PAIR 3' COMPL: 1.00

```
  1 GGCAGAGGCATGGGGTGCATAGGGATATGGGGTGGGCCAGTTTGCTCCTCAGACCAGAAG
                                            >>>>>>>>>>>>>>>>>>>>

61 GGGTGCAGGAcTCCCCCCGATCAGGATCaTGGAGAAAGGTGTGGACAGAGGAAGGGAGGG
       >                    <<<<<<<<<<<<<<<<<<<<

121 AGGGAGAAATGGCAGCTGCCCTGCAGTGG
```

80) Whole sequence ::: rs2838089-rs2838090
cagggactaagtgtctctgacaatacattcagccactactAcagtatgaagccagcccct catccccaccttcagagacccctggtgcctcagattcctcggccattctggagctgctgt gCCCGAGGCTTGTGTAGTTGGAGATCATTTTGGCAGTCAGTGCTG (SEQ ID NO: 229)

OLIGO start len tm gc % any http://frodo.wi.mit.edu/cgi-bin/primer3/
primer3_www_results_help.cgi - PRIMER_THREE 3' seq (SEQ ID NOs: 230, 231)
LEFT PRIMER    12 22 55.48 40.91 5.00 2.00 tgtctctgacaatacattcagc
RIGHT PRIMER  160 20 55.81 45.00 4.00 2.00 CTGACTGCCAAAATGATCTC
SEQUENCE SIZE: 165
INCLUDED REGION SIZE: 165
PRODUCT SIZE: 149, PAIR ANY COMPL: 5.00, PAIR 3' COMPL: 1.00

```
  1 cagggactaagtgtctctgacaatacattcagccactactAcagtatgaagccagcccct
                  >>>>>>>>>>>>>>>>>>>>>>

61 catccccaccttcagagacccctggtgcctcagattcctcggccattctggagctgctgt 121 gCCCGAGGCTTGTGTAGTTGGAGATCATTTTGGCAGTCAGTGCTG
              <<<<<<<<<<<<<<<<<<<<
```

12th group
81) Whole sequence ::: rs453592-rs380152
CCTGTCTCCGTGCGTGAAAGCCGGCTCCAAAGTGCCTTCTGTCCTATCTGCCTTCcGCAC

CTGGCTTTCCTGAAAGAAAGAAAACGCGTGGCTTATCTTTTCACGGCACGCCACCTTCAC

TCTCaCTTTTTCTTTTCTAATAAATACCTCTGGATGGGTTAGTGGTAATCTCTCCTCAAAC (SEQ ID NO: 232)

OLIGO start len tm gc % any http://frodo.wi.mit.edu/cgi-bin/primer3/
primer3_www_results_help.cgi - PRIMER_THREE 3' seq (SEQ ID NOs: 233, 234)
LEFT PRIMER    24 20 60.00 55.00 4.00 1.00 GCTCCAAAGTGCCTTCTGTC
RIGHT PRIMER  165 20 58.87 55.00 3.00 2.00 CCACTAACCCATCCAGAGGT
SEQUENCE SIZE: 181
INCLUDED REGION SIZE: 181
PRODUCT SIZE: 142, PAIR ANY COMPL: 4.00, PAIR 3' COMPL: 1.00

TABLE 2-continued

```
  1 CCTGTCTCCGTGCGTGAAAGCCGGCTCCAAAGTGCCTTCTGTCCTATCTGCCTTCcGCAC
            >>>>>>>>>>>>>>>>>>>>

61 CTGGCTTTCCTGAAAGAAAGAAAACGCGTGGCTTATCTTTTCACGGCACGCCACCTTCAC

121 TCTCaCTTTTTCTTTTCTAATAAATACCTCTGGATGGGTTAGTGGTAATCTCTCCTCAAA
            <<<<<<<<<<<<<<<<<<<<

181 C
```

82) Whole sequence ::: rs442723-rs449888
GGGAGCACAACCTAGGCCCCTCCTGGGGAGGTGGTGGAGTCAGAATCACGTAAGAGaCAA

AGTTCCAGTCCCTCAGTGCCGGCTCCATTGTCCCCTGGACTTCCCTTACAAACCACAGAT

GCAAAGAGAGCACTTCTCgGAATCTCCACACAGCCACGGTGGAGCACTCAACCCACGCGA

CCCTCGGGCGCAGGTGCT (SEQ ID NO: 235)

OLIGO start len tm gc % any http://frodo.wi.mit.edu/cgi-bin/primer3/
primer3_www_results_help.cgi - PRIMER_THREE 3' seq (SEQ ID NOs: 236, 237)
LEFT PRIMER    23 20 65.82 65.00 3.00 1.00 CTGGGGAGGTGGTGGAGTCA
RIGHT PRIMER  169 20 66.12 65.00 7.00 1.00 GAGTGCTCCACCGTGGCTGT
SEQUENCE SIZE: 198
INCLUDED REGION SIZE: 198
PRODUCT SIZE: 147, PAIR ANY COMPL: 7.00, PAIR 3' COMPL: 1.00

```
  1 GGGAGCACAACCTAGGCCCCTCCTGGGGAGGTGGTGGAGTCAGAATCACGTAAGAGaCAA
            >>>>>>>>>>>>>>>>>>>>

61 AGTTCCAGTCCCTCAGTGCCGGCTCCATTGTCCCCTGGACTTCCCTTACAAACCACAGAT

121 GCAAAGAGAGCACTTCTCgGAATCTCCACACAGCCACGGTGGAGCACTCAACCCACGCGA
            <<<<<<<<<<<<<<<<<<<<

181 CCCTCGGGCGCAGGTGCT
```

83) Whole sequence ::: rs375886-rs9976560
CCTGAGAAGCTTCCAGCAAAGCACCAGCACGAACCGCCCCACCTCCCCACCTCCCCGCAA GCGTTGcCGGGACTGACAGATTACAGAGCTCTGgTCCCTCTGCACTCCTGCTCTGCCACC

CCCAGGGTGTCAGAATGTGCCCCCCACACAGTTTCCAAAAG (SEQ ID NO: 238)

OLIGO start len tm gc % any http://frodo.wi.mit.edu/cgi-bin/primer3/
primer3_www_results_help.cgi - PRIMER_THREE 3' seq (SEQ ID NOs: 239, 240)
LEFT PRIMER    18 18 59.84 55.56 2.00 0.00 AAAGCACCAGCACGAACC
RIGHT PRIMER  143 18 59.89 61.11 3.00 3.00 GGGGCACATTCTGACACC
SEQUENCE SIZE: 161
INCLUDED REGION SIZE: 161
PRODUCT SIZE: 126, PAIR ANY COMPL: 3.00, PAIR 3' COMPL: 0.00

```
  1 CCTGAGAAGCTTCCAGCAAAGCACCAGCACGAACCGCCCCACCTCCCCACCTCCCCGCAA
            >>>>>>>>>>>>>>>>>>

61 GCGTTGcCGGGACTGACAGATTACAGAGCTCTGgTCCCTCTGCACTCCTGCTCTGCCACC

121 CCCAGGGTGTCAGAATGTGCCCCCCACACAGTTTCCAAAAG
            <<<<<<<<<<<<<<<<<<
```

84) Whole sequence ::: rs3819900-rs3819901
ATGGAGCTGCTGCGCCGGCCTGAGCTCTGATCCCTCCTCCGACCCAGCCTCACCCTGCaA GCAGCACCATGTGGGGCTCAGAATGGGGATCTTAAGGGACCCTcCCCACAACCTCCCGAT

AAGCCTTTCCACGGAGGGCCCAAGCGGAGACAGGAGAACACT (SEQ ID NO: 241)

OLIGO start len tm gc % any http://frodo.wi.mit.edu/cgi-bin/primer3/
primer3_www_results_help.cgi - PRIMER_THREE 3' seq (SEQ ID NOs: 242, 243)
LEFT PRIMER    20 19 57.00 57.89 6.00 0.00 CTGAGCTCTGATCCCTCCT
RIGHT PRIMER  158 18 57.51 55.56 2.00 0.00 TTCTCCTGTCTCCGCTTG
SEQUENCE SIZE: 162
INCLUDED REGION SIZE: 162
PRODUCT SIZE: 139, PAIR ANY COMPL: 3.00, PAIR 3' COMPL: 0.00

TABLE 2-continued

```
  1 ATGGAGCTGCTGCGCCGGCCTGAGCTCTGATCCCTCCTCCGACCCAGCCTCACCCTGCaA
       >>>>>>>>>>>>>>>>>>>>

61 GCAGCACCATGTGGGGCTCAGAATGGGGATCTTAAGGGACCCTcCCCACAACCTCCCGAT

121 AAGCCTTTCCACGGAGGGCCCAAGCGGAGACAGGAGAACACT
         <<<<<<<<<<<<<<<<<

85) Whole sequence ::: rs10451852-rs10451853
ACTTTCAGAATGTGCTGCCTTCCACGTGTGAACCAGACTGAGCTCCTTTCTGCCACTGAT GTTGAATTGTCCATTTGCTCACaTCAGTGTCCACGTGGCAAATCCACAGGGCgTGGGTGG

GATCCTGCAGTCTAGACAAAGCCAAGGAGCACCGCTGGAGGCCACGTTGGGCTTCCCAAT

CCACATGCAAACCC (SEQ ID NO: 244)

OLIGO start len tm gc % any http://frodo.wi.mit.edu/cgi-bin/primer3/
primer3_www_results_help.cgi - PRIMER_THREE 3' seq (SEQ ID NOs: 245, 246)
LEFT PRIMER    45 20 59.29 50.00 3.00 1.00 CCTTTCTGCCACTGATGTTG
RIGHT PRIMER  190 19 60.46 47.37 4.00 0.00 TTGCATGTGGATTGGGAAG
SEQUENCE SIZE: 194
INCLUDED REGION SIZE: 194
PRODUCT SIZE: 146, PAIR ANY COMPL: 4.00, PAIR 3' COMPL: 0.00

1 ACTTTCAGAATGTGCTGCCTTCCACGTGTGAACCAGACTGAGCTCCTTTCTGCCACTGAT
                   >>>>>>>>>>>>>>>>

61 GTTGAATTGTCCATTTGCTCACaTCAGTGTCCACGTGGCAAATCCACAGGGCgTGGGTGG
       >>>>

121 GATCCTGCAGTCTAGACAAAGCCAAGGAGCACCGCTGGAGGCCACGTTGGGCTTCCCAAT
                  >>>>>>>>>

181 CCACATGCAAACCC
       >>>>>>>>>>

86) Whole sequence ::: rs7278528-rs11701158
TCTCCAGCCAGCGTGTCACAAAGCCGCTCACCTGCTCGTGTGAGTGTCTGAATGCACGTG TTTGAGTGTCAGaGGCGTGTGAACCACAGCAACTCAATCTTGAATAGGGGCTGGGTAAAG TGAGGCTgAGACCTCCCGGGGCTGCATTCCCAGATGGTTAAGGCATTCTAAGTCACAAGA

TGAGATAGGAAGTTCGCACAAGACACTGGTCAT (SEQ ID NO: 247)

OLIGO start len tm gc % any http://frodo.wi.mit.edu/cgi-bin/primer3/
primer3_www_results_help.cgi - PRIMER_THREE 3' seq (SEQ ID NOs: 248, 249)
LEFT PRIMER    28 20 60.53 55.00 4.00 0.00 TCACCTGCTCGTGTGAGTGT
RIGHT PRIMER  163 20 59.39 50.00 4.00 2.00 CCTTAACCATCTGGGAATGC
SEQUENCE SIZE: 213
INCLUDED REGION SIZE: 213
PRODUCT SIZE: 136, PAIR ANY COMPL: 3.00, PAIR 3' COMPL: 0.00

1 TCTCCAGCCAGCGTGTCACAAAGCCGCTCACCTGCTCGTGTGAGTGTCTGAATGCACGTG
                   >>>>>>>>>>>>>>>>>>>>

61 TTTGAGTGTCAGaGGCGTGTGAACCACAGCAACTCAATCTTGAATAGGGGCTGGGTAAAG

121 TGAGGCTgAGACCTCCCGGGGCTGCATTCCCAGATGGTTAAGGCATTCTAAGTCACAAGA
            <<<<<<<<<<<<<<<<<<<<

181 TGAGATAGGAAGTTCGCACAAGACACTGGTCAT

87) Whole sequence ::: rs2839627-rs170916
TTGAGTCCTCTTAAGTAGTTACTATAGTGGAGAACTTGAGTCATTCTTTGTAGCGTGCTT cGTAGAGCAGCGTGTTTGTTAGAAGGATTTGTTAATCCTGTATAGgGTCTTTACGAAGGC

TGTTTTCATGGAAGCTTCTCTTTGTTGACTCC (SEQ ID NO: 250)

OLIGO start len tm gc % any http://frodo.wi.mit.edu/cgi-bin/primer3/
primer3_www_results_help.cgi - PRIMER_THREE 3' seq (SEQ ID NOs: 251, 252)
LEFT PRIMER    28 22 55.68 36.36 5.00 1.00 TGGAGAACTTGAGTCATTCTTT
RIGHT PRIMER  152 19 52.33 47.37 3.00 2.00 GGAGTCAACAAAGAGAAGC
SEQUENCE SIZE: 152
INCLUDED REGION SIZE: 152
PRODUCT SIZE: 125, PAIR ANY COMPL: 5.00, PAIR 3' COMPL: 3.00
```

TABLE 2-continued

```
  1 TTGAGTCCTCTTAAGTAGTTACTATAGTGGAGAACTTGAGTCATTCTTTGTAGCGTGCTT
              >>>>>>>>>>>>>>>>>>>>>

61 cGTAGAGCAGCGTGTTTGTTAGAAGGATTTGTTAATCCTGTATAGgGTCTTTACGAAGGC

121 TGTTTTCATGGAAGCTTCTCTTTGTTGACTCC
              <<<<<<<<<<<<<<<<<<<
```

88) Whole sequence ::: rs2839628-rs234740
CATTCTCTCCAGCTGCAAACTTTCTTCAACTTTCCTAAATTCTTAcTAAATTCAGAGGAA

TAGGATAAAGATCACTTAGAGAAAGGGTGCTTATGGACATAGCCTGAGTTTCCTTTAACC

TCTCTgCAATGGGTGCTTTTAACTAGCTTCTACATGGCAAGCTGTTTCAGTTTG (SEQ ID NO: 253)

OLIGO start len tm gc % any http://frodo.wi.mit.edu/cgi-bin/primer3/
primer3_www_results_help.cgi - PRIMER_THREE 3' seq (SEQ ID NOs: 254, 255)
LEFT PRIMER    20 21  50.06  28.57  3.00  2.00 CTTTCTTCAACTTTCCTAAAT
RIGHT PRIMER  160 19  50.96  42.11  4.00  2.00 TTGCCATGTAGAAGCTAGT
SEQUENCE SIZE: 174
INCLUDED REGION SIZE: 174
PRODUCT SIZE: 141, PAIR ANY COMPL: 5.00, PAIR 3' COMPL: 2.00

```
  1 CATTCTCTCCAGCTGCAAACTTTCTTCAACTTTCCTAAATTCTTAcTAAATTCAGAGGAA
              >>>>>>>>>>>>>>>>>>>>>

61 TAGGATAAAGATCACTTAGAGAAAGGGTGCTTATGGACATAGCCTGAGTTTCCTTTAACC

121 TCTCTgCAATGGGTGCTTTTAACTAGCTTCTACATGGCAAGCTGTTTCAGTTTG
              <<<<<<<<<<<<<<<<<<<
```

89) Whole sequence ::: rs2838239-rs2838240
GGACATCTGGAACTGCACCAGCACAGAACCGACACGTTGTTAcTCATCGTCACTCGGCAG

GGCTGAAGACCACCAGAACTCATGACAGGCAGACGTGCCTGGCCCAGTTGAGGATGTAGC tTCAGAGCCAAGCGCCAGTCCTGTTGGCCACGTGGGCTGGGGGCAGGATAGACCA (SEQ ID NO: 256)

OLIGO start len tm gc % any http://frodo.wi.mit.edu/cgi-bin/primer3/
primer3_www_results_help.cgi - PRIMER_THREE 3' seq (SEQ ID NOs: 257, 258)
LEFT PRIMER    17 19  59.73  57.89  2.00  0.00 ACCAGCACAGAACCGACAC
RIGHT PRIMER  145 18  62.40  61.11  4.00  0.00 AACAGGACTGGCGCTTGG
SEQUENCE SIZE: 175
INCLUDED REGION SIZE: 175
PRODUCT SIZE: 129, PAIR ANY COMPL: 4.00, PAIR 3' COMPL: 1.00

```
  1 GGACATCTGGAACTGCACCAGCACAGAACCGACACGTTGTTAcTCATCGTCACTCGGCAG
              >>>>>>>>>>>>>>>>>>>

61 GGCTGAAGACCACCAGAACTCATGACAGGCAGACGTGCCTGGCCCAGTTGAGGATGTAGC 121 tTCAGAGCCAAGCGCCAGTCCTGTTGGCCACGTGGGCTGGGGGCAGGATAGACCA
              <<<<<<<<<<<<<<<<<<
```

90) Whole sequence ::: rs630397-rs11089106
GGCTGGTTCTGCCCTTGGGAGGTGGTTCCTTTGGCTGGACCAGAATGTCTGaAGATGATC

AGGAGAGGGCCAAGGGTTGGGGGGTGCCCCATGTGCACCCTGAGAATTGCACCAGGCACA

GtGAGCAACTTCAGCCCTCCTTGTGCAGAGCTGCAGCGTACAGTGCCAGCCCTCGCTGGC

CC (SEQ ID NO: 259)

OLIGO start len tm gc % any http://frodo.wi.mit.edu/cgi-bin/primer3/
primer3_www_results_help.cgi - PRIMER_THREE 3' seq (SEQ ID NOs: 260, 261)
LEFT PRIMER    14 20  61.79  55.00  3.00  0.00 CTTGGGAGGTGGTTCCTTTG
RIGHT PRIMER  148 18  61.15  61.11  4.00  1.00 CTGCACAAGGAGGGCTGA
SEQUENCE SIZE: 182
INCLUDED REGION SIZE: 182
PRODUCT SIZE: 135, PAIR ANY COMPL: 5.00, PAIR 3' COMPL: 0.00

```
  1 GGCTGGTTCTGCCCTTGGGAGGTGGTTCCTTTGGCTGGACCAGAATGTCTGaAGATGATC
              >>>>>>>>>>>>>>>>>>>>

61 AGGAGAGGGCCAAGGGTTGGGGGGTGCCCCATGTGCACCCTGAGAATTGCACCAGGCACA

121 GtGAGCAACTTCAGCCCTCCTTGTGCAGAGCTGCAGCGTACAGTGCCAGCCCTCGCTGGC
              <<<<<<<<<<<<<<<<<<

181 CC
```

TABLE 2-continued

91) Whole sequence ::: rs9637180-rs481767
GTTCTCACTTTACTGAGAAACCTGGCAGCTTCTCAGGCCACCGCCCAGGTCACCTGCTCA CCAGCAAcGTGAACCACAGGAACtGAGGCTGTGCGGGAGGCGGCTCTGCTCTGTGCTGGG

CCCCCCTCCTCCTCACTCACCCTCTTCAGTCAAAG (SEQ ID NO: 262)

OLIGO start len tm gc % any http://frodo.wi.mit.edu/cgi-bin/primer3/
primer3_www_results_help.cgi - PRIMER_THREE 3' seq (SEQ ID NOs: 263, 264)
LEFT PRIMER    11 20  57.70  50.00  5.00  5.00 TACTGAGAAACCTGGCAGCT
RIGHT PRIMER  155 20  54.98  50.00  3.00  0.00 CTTTGACTGAAGAGGGTGAG
SEQUENCE SIZE: 155
INCLUDED REGION SIZE: 155
PRODUCT SIZE: 145, PAIR ANY COMPL: 3.00, PAIR 3' COMPL: 2.00

1 GTTCTCACTTTACTGAGAAACCTGGCAGCTTCTCAGGCCACCGCCCAGGTCACCTGCTCA
              >>>>>>>>>>>>>>>>>>>>

61 CCAGCAAcGTGAACCACAGGAACtGAGGCTGTGCGGGAGGCGGCTCTGCTCTGTGCTGGG

121 CCCCCCTCCTCCTCACTCACCCTCTTCAGTCAAAG
              <<<<<<<<<<<<<<<<<<<<

92) Whole sequence ::: rs162360-rs162359
TTAGTATTATTATTTTCATATATATTTTTTATAATAATCATATATTCAATTTTATCATCA AGAAAAAAGTTTTAAAATTCaAAATCCTTTCATGTGCACTGTTTTAAACTtAGGTAGAAG

AAAAAAAGTCACTGAAAATCCAAGATGTAATAAACAGGCCCAACAAAGGCCAACAAACTT (SEQ ID NO: 265)

OLIGO start len tm gc % any http://frodo.wi.mit.edu/cgi-bin/primer3/
primer3_www_results_help.cgi - PRIMER_THREE 3' seq (SEQ ID NOs: 266, 267)
LEFT PRIMER    45 20  48.37  20.00  5.00  3.00 TTCAATTTTATCATCAAGAA
RIGHT PRIMER  163 20  55.18  40.00  4.00  1.00 TTGGGCCTGTTTATTACATC
SEQUENCE SIZE: 180
INCLUDED REGION SIZE: 180
PRODUCT SIZE: 119, PAIR ANY COMPL: 4.00, PAIR 3' COMPL: 1.00

1 TTAGTATTATTATTTTCATATATATTTTTTATAATAATCATATATTCAATTTTATCATCA
                         >>>>>>>>>>>>>>>>

61 AGAAAAAAGTTTTAAAATTCaAAATCCTTTCATGTGCACTGTTTTAAACTtAGGTAGAAG
      >>>>

121 AAAAAAAGTCACTGAAAATCCAAGATGTAATAAACAGGCCCAACAAAGGCCAACAAACTT
                <<<<<<<<<<<<<<<<<<<<

93) Whole sequence ::: rs162356-rs162355
AGGGAACATGGCCTTGCCCACACAGATTTCAGACATCTGGCTCCAGAACTGTGGGAGGAC ACATTTCTGTTGTTTAGAACTGCaTGTTTTTTATACTTTGTTATGGCTGCCCTAGGcAAC

TAATACAGATATTATTTTCCACTTCTGAACTTAGCAAAATATTTTTAAAATGAAAATTCT

TAAATGTTGGCACAGT (SEQ ID NO: 268)

OLIGO start len tm gc % any http://frodo.wi.mit.edu/cgi-bin/primer3/
primer3_www_results_help.cgi - PRIMER_THREE 3' seq (SEQ ID NOs: 269, 270)
LEFT PRIMER    14 20  60.24  45.00  3.00  3.00 TTGCCCACACAGATTTCAGA
RIGHT PRIMER  156 22  56.88  36.36  5.00  0.00 TGCTAAGTTCAGAAGTGGAAAA
SEQUENCE SIZE: 196
INCLUDED REGION SIZE: 196
PRODUCT SIZE: 143, PAIR ANY COMPL: 4.00, PAIR 3' COMPL: 2.00

1 AGGGAACATGGCCTTGCCCACACAGATTTCAGACATCTGGCTCCAGAACTGTGGGAGGAC
                 >>>>>>>>>>>>>>>>>>>>

61 ACATTTCTGTTGTTTAGAACTGCaTGTTTTTTATACTTTGTTATGGCTGCCCTAGGcAAC

121 TAATACAGATATTATTTTCCACTTCTGAACTTAGCAAAATATTTTTAAAATGAAAATTCT
               <<<<<<<<<<<<<<<<<<<<<<

181 TAAATGTTGGCACAGT

94) Whole sequence ::: rs91424-rs463738
CTGGATAAAGGATGCTACACGTCCCTGGTGGGACAGAGCAGGACGGCAGGGGATTTCATT AcGCCAcTCAGAATGGCAGGCAATTGAAAAAACTTATAAATTGTTTATTTCCAGAATTTT (SEQ ID NO: 271)

TABLE 2-continued

```
OLIGO    start  len   tm    gc %  any   http://frodo.wi.mit.edu/cgi-bin/primer3/
                                        primer3_www_results_help.cgi - PRIMER_THREE 3' seq (SEQ ID NOs: 272, 273)
LEFT PRIMER   3   20   54.33 45.00 4.00 4.00 GGATAAAGGATGCTACACGT
RIGHT PRIMER 120  20   49.40 20.00 4.00 0.00 AAAATTCTGGAAATAAACAA
SEQUENCE SIZE: 120
INCLUDED REGION SIZE: 120
PRODUCT SIZE: 118, PAIR ANY COMPL: 3.00, PAIR 3' COMPL: 1.00

1 CTGGATAAAGGATGCTACACGTCCCTGGTGGGACAGAGCAGGACGGCAGGGGATTTCATT
     >>>>>>>>>>>>>>>>>>>>

61 AcGCCAcTCAGAATGGCAGGCAATTGAAAAAACTTATAAATTGTTTATTTCCAGAATTTT
                       <<<<<<<<<<<<<<<<<<<<

95) Whole sequence ::: rs2838318-rs2838319
TGTCAGTGGTGTAATCCGACTGTGAAAGATCAGTCTAACAAAACAGCGGGGAGAGAGAGG GCTGAATCAGAGCaACTAGGTCCAAAGCCGAGGGAACCACCAACAGATCCCCTGGTGACC CAACAAGAAATGCTCACAGTCTGGACCCAgTCAGAGTCTGCAGGACACAGCAGACATTCT

GGAAGTTACAACAGCCAGGAGCAAGAGGACGCATGGCCTGACTG (SEQ ID NO: 274)

OLIGO    start  len   tm    gc %  any   http://frodo.wi.mit.edu/cgi-bin/primer3/
                                        primer3_www_results_help.cgi - PRIMER_THREE 3' seq (SEQ ID NOs: 275, 276)
LEFT PRIMER   49  20   60.30 60.00 3.00 3.00 GGGAGAGAGAGGGCTGAATC
RIGHT PRIMER 202  21   59.00 52.38 4.00 2.00 GCTCCTGGCTGTTGTAACTTC
SEQUENCE SIZE: 224
INCLUDED REGION SIZE: 224
PRODUCT SIZE: 154, PAIR ANY COMPL: 4.00, PAIR 3' COMPL: 1.00

1 TGTCAGTGGTGTAATCCGACTGTGAAAGATCAGTCTAACAAAACAGCGGGGAGAGAGAGG
                                                    >>>>>>>>>>>

61 GCTGAATCAGAGCaACTAGGTCCAAAGCCGAGGGAACCACCAACAGATCCCCTGGTGACC
     >>>>>>>>

121 CAACAAGAAATGCTCACAGTCTGGACCCAgTCAGAGTCTGCAGGACACAGCAGACATTCT

181 GGAAGTTACAACAGCCAGGAGCAAGAGGACGCATGGCCTGACTG
        <<<<<<<<<<<<<<<<<<<<<

96) Whole sequence ::: rs915770-rs731935
CGCCAGAGCACCCCTTCTCAGAACAGAAAGCGTCTCTACAaAGTGATCCGGAAGTGAGTG

TGTGAGGGCGCTGCGTCCTCCCTGCTCCCCTTGGAGTTGCCCTTTCTTGCTCAGATCTGG

GTGCCTTgGCCTTGTCCTGGGCCCTTCCGCAGCCCCCGGGGTGATCCCCGCTAG (SEQ ID NO: 277)

OLIGO    start  len   tm    gc %  any   http://frodo.wi.mit.edu/cgi-bin/primer3/
                                        primer3_www_results_help.cgi - PRIMER_THREE 3' seq (SEQ ID NOs: 278, 279)
LEFT PRIMER   3   19   60.95 63.16 3.00 3.00 CCAGAGCACCCCTTCTCAG
RIGHT PRIMER 148  18   62.95 66.67 6.00 0.00 GGAAGGGCCCAGGACAAG
SEQUENCE SIZE: 174
INCLUDED REGION SIZE: 174
PRODUCT SIZE: 146, PAIR ANY COMPL: 6.00, PAIR 3' COMPL: 2.00

1 CGCCAGAGCACCCCTTCTCAGAACAGAAAGCGTCTCTACAaAGTGATCCGGAAGTGAGTG
     >>>>>>>>>>>>>>>>>>>

61 TGTGAGGGCGCTGCGTCCTCCCTGCTCCCCTTGGAGTTGCCCTTTCTTGCTCAGATCTGG

121 GTGCCTTgGCCTTGTCCTGGGCCCTTCCGCAGCCCCCGGGGTGATCCCCGCTAG
           <<<<<<<<<<<<<<<<<<

Final Set
97) Whole sequence ::: rs1573338-rs1573339
TATCTTACGGATTTGTCAACATCATTTGAGAAGAAGTCCATAGGCTCAGCAGATTTTTAT GCCAGGTGGGCCATGGCATAAAAATGTGAAGAATGTGCTCaCTTAGACAATACcTGTGCT

AAAATTGGAACAATACAGAGAAGATTAGCAAATTAAAACAATGTTAGGAAGTCAGTGTGG

TGAGGTACGGTGCCTCATGCC (SEQ ID NO: 280)
```

TABLE 2-continued

```
OLIGO    start len tm    gc %  any http://frodo.wi.mit.edu/cgi-bin/primer3/
                              primer3_www_results_help.cgi - PRIMER_THREE 3' seq (SEQ ID NOs: 281, 282)
LEFT PRIMER    47 21 59.24 42.86 3.00 1.00 CAGCAGATTTTTATGCCAGGT
RIGHT PRIMER  192 20 60.06 60.00 4.00 3.00 CACCGTACCTCACCACACTG
SEQUENCE SIZE: 201
INCLUDED REGION SIZE: 201
PRODUCT SIZE: 146, PAIR ANY COMPL: 4.00, PAIR 3' COMPL: 3.00

1 TATCTTACGGATTTGTCAACATCATTTGAGAAGAAGTCCATAGGCTCAGCAGATTTTTAT
                                                 >>>>>>>>>>>>>

61 GCCAGGTGGGCCATGGCATAAAAATGTGAAGAATGTGCTCaCTTAGACAATACcTGTGCT
    >>>>>>>

121 AAAATTGGAACAATACAGAGAAGATTAGCAAATTAAAACAATGTTAGGAAGTCAGTGTGG
                    <<<<<<<<

181 TGAGGTACGGTGCCTCATGCC
    <<<<<<<<<<<

98) Whole sequence :::  rs3788094-rs3788095
AGGCAGGGCCCTCCTTGCCACATGTAAAGCTGCACAGAGCGGTCACTATATGTGTTTCCA TATTTGCAATCCAACCACCACCAACTGAGTGTGCGTCCTGaTCAGCCGAGCCTGCCCACG GTGGCCACAGGCCCTCTACATTCTAATCTCGAGAGCCTGAGCATGTACAAATTAAACgAA

GCAAAACGACACCACCCAGTTCTGGCCGTACTATAGGAGGTTTCCAGGAAGGGTTTGTGA

ACATAAACATAAGCTAGGTAACACTCCTTTCTGAA (SEQ ID NO: 283)

OLIGO    start len tm    gc %  any http://frodo.wi.mit.edu/cgi-bin/primer3/
                              primer3_www_results_help.cgi - PRIMER_THREE 3' seq (SEQ ID NOs: 284, 285)
LEFT PRIMER    73 20 57.88 50.00 5.00 3.00 AACCACCACCAACTGAGTGT
RIGHT PRIMER  220 20 56.94 55.00 6.00 2.00 CCTCCTATAGTACGGCCAGA
SEQUENCE SIZE: 275
INCLUDED REGION SIZE: 275
PRODUCT SIZE: 148, PAIR ANY COMPL: 3.00, PAIR 3' COMPL: 1.00

1 AGGCAGGGCCCTCCTTGCCACATGTAAAGCTGCACAGAGCGGTCACTATATGTGTTTCCA

61 TATTTGCAATCCAACCACCACCAACTGAGTGTGCGTCCTGaTCAGCCGAGCCTGCCCACG
            >>>>>>>>>>>>>>>>>>>>

121 GTGGCCACAGGCCCTCTACATTCTAATCTCGAGAGCCTGAGCATGTACAAATTAAACgAA

181 GCAAAACGACACCACCCAGTTCTGGCCGTACTATAGGAGGTTTCCAGGAAGGGTTTGTGA
            <<<<<<<<<<<<<<<<<<<<

241 ACATAAACATAAGCTAGGTAACACTCCTTTCTGAA

99) Whole sequence :::  rs756554-rs756555
TCAGAGCATCGCCTCAGTGGCCATCAATAGCTCGGGGGACTGGATTGCTTTTGGCTGTTC AGGTTTGTCCCCaGCCTGGGTGGTAGAGATGGACTCCCCATTAGGGACCAGTGCTGCCCG GCTACAGGCtTACTTGACAGCCACCCACTGGGGGTGCCCTCCCCTCCCCCAGTTGTCTTC

CATGGGGTGCCCTCTCCCCCAGCCGCCTTTCAGAAGGGGCCCTCCCCTCC (SEQ ID NO: 286)

OLIGO    start len tm    gc %  any http://frodo.wi.mit.edu/cgi-bin/primer3/
                              primer3_www_results_help.cgi - PRIMER_THREE 3' seq (SEQ ID NOs: 287, 288)
LEFT PRIMER    41 20 61.15 45.00 2.00 0.00 TGGATTGCTTTTGGCTGTTC
RIGHT PRIMER  189 20 61.37 55.00 6.00 2.00 CACCCCATGGAAGACAACTG
SEQUENCE SIZE: 230
INCLUDED REGION SIZE: 230
PRODUCT SIZE: 149, PAIR ANY COMPL: 4.00, PAIR 3' COMPL: 2.00

1 TCAGAGCATCGCCTCAGTGGCCATCAATAGCTCGGGGGACTGGATTGCTTTTGGCTGTTC
                                                 >>>>>>>>>>>>>>>>>>>>

61 AGGTTTGTCCCCaGCCTGGGTGGTAGAGATGGACTCCCCATTAGGGACCAGTGCTGCCCG

121 GCTACAGGCtTACTTGACAGCCACCCACTGGGGGTGCCCTCCCCTCCCCCAGTTGTCTTC
                                 <<<<<<<<<<

181 CATGGGGTGCCCTCTCCCCCAGCCGCCTTTCAGAAGGGGCCCTCCCCTCC
    <<<<<<<<<<
```

TABLE 2-continued

100) Whole sequence ::: rs4350841-rs2838545
CTCATGCTTACATCCTTAGCTGATCATTAAACTTTGTGACCATTTCATGCTCACTGCTTT CTTGCCcGGGAGCTAATGGTGAGGAAAGGTCACTGGGAACCAGCGCACCAACCTCAGACA TcGATTTTGTTCCAGCCTTTTTTCCTGGGCAGGGGTGGCTATCACCTGCTGGTAGGCAGC

GGCAGGCCCACTGTCCTGC (SEQ ID NO: 289)

OLIGO start len tm gc % any http://frodo.wi.mit.edu/cgi-bin/primer3/
primer3_www_results_help.cgi - PRIMER_THREE 3' seq (SEQ ID NOs: 290, 291)
LEFT PRIMER    27 21  53.45  28.57  5.00  2.00 TTAAACTTTGTGACCATTTCA
RIGHT PRIMER  174 18  54.55  55.56  6.00  2.00 TACCAGCAGGTGATAGCC
SEQUENCE SIZE: 199
INCLUDED REGION SIZE: 199
PRODUCT SIZE: 148, PAIR ANY COMPL: 3.00, PAIR 3' COMPL: 0.00

1 CTCATGCTTACATCCTTAGCTGATCATTAAACTTTGTGACCATTTCATGCTCACTGCTTT
                                >>>>>>>>>>>>>>>>>>>>>

61 CTTGCCcGGGAGCTAATGGTGAGGAAAGGTCACTGGGAACCAGCGCACCAACCTCAGACA

121 TcGATTTTGTTCCAGCCTTTTTTCCTGGGCAGGGGTGGCTATCACCTGCTGGTAGGCAGC
                                      <<<<<<<<<<<<<<<<<<

181 GGCAGGCCCACTGTCCTGC

101) Whole sequence ::: rs2838551-rs2838552
TGACAGAAAAGTCTCAGAGCAGTGCCTTCTGAGCTCTTCTACACCAAGCAGGCAGAATGT TCACTGCTAATGAGgCTGGAGCTGGTCCCCAGCAGTGGTAGGAAGCTTCCAaCAGGCTCA

GGCTGTGGGTGCTTGCAGGGGCACAGTGTGACGGCCACGGGCCTCAGAGCTCTGGTGGGC

T (SEQ ID NO: 292)

OLIGO start len tm gc % any http://frodo.wi.mit.edu/cgi-bin/primer3/
primer3_www_results_help.cgi - PRIMER_THREE 3' seq (SEQ ID NOs: 293, 294)
LEFT PRIMER     2 20  53.05  45.00  5.00  3.00 GACAGAAAAGTCTCAGAGCA
RIGHT PRIMER  135 18  62.10  61.11  5.00  3.00 CAAGCACCCACAGCCTGA
SEQUENCE SIZE: 181
INCLUDED REGION SIZE: 181
PRODUCT SIZE: 134, PAIR ANY COMPL: 4.00, PAIR 3' COMPL: 3.00

1 TGACAGAAAAGTCTCAGAGCAGTGCCTTCTGAGCTCTTCTACACCAAGCAGGCAGAATGT
     >>>>>>>>>>>>>>>>>>>>

61 TCACTGCTAATGAGgCTGGAGCTGGTCCCCAGCAGTGGTAGGAAGCTTCCAaCAGGCTCA
                                                        <<<

121 GGCTGTGGGTGCTTGCAGGGGCACAGTGTGACGGCCACGGGCCTCAGAGCTCTGGTGGGC
        <<<<<<<<<<<<<<<

181 T

102) Whole sequence ::: rs8134902-rs8133874
ACATCTTTCTCAAATAAAGATAACAGCGATGTATTTTCACAAAAGCAAGAGCTTAGAAAG TACTcCACCCAGGTATCCCTCTTGGAAAAAATaCTTAAGGAAATATGACAAATGGCAAAG

TGATTGTTATGGATGGAATGTTTGTATCCTCCCAAAATTCACATGTTGAGACCCTAATTC

CAATATG (SEQ ID NO: 295)

OLIGO start len tm gc % any http://frodo.wi.mit.edu/cgi-bin/primer3/
primer3_www_results_help.cgi - PRIMER_THREE 3' seq (SEQ ID NOs: 296, 297)
LEFT PRIMER    33 20  54.84  35.00  5.00  2.00 ATTTTCACAAAAGCAAGAGC
RIGHT PRIMER  155 20  54.97  40.00  3.00  0.00 TTGGGAGGATACAAACATTC
SEQUENCE SIZE: 187
INCLUDED REGION SIZE: 187
PRODUCT SIZE: 123, PAIR ANY COMPL: 4.00, PAIR 3' COMPL: 0.00

TABLE 2-continued

```
  1 ACATCTTTCTCAAATAAAGATAACAGCGATGTATTTTCACAAAAGCAAGAGCTTAGAAAG
               >>>>>>>>>>>>>>>>>>>>

61 TACTcCACCCAGGTATCCCTCTTGGAAAAAATaCTTAAGGAAATATGACAAATGGCAAAG

121 TGATTGTTATGGATGGAATGTTTGTATCCTCCCAAAATTCACATGTTGAGACCCTAATTC
            <<<<<<<<<<<<<<<<<<<

181 CAATATG

103) Whole sequence ::: rs425667-rs382478
AGGGGCATTCTACAAAACACCCAACCGGTCAAGGTCGCTGAGGCCAAGGAGAGATTGGGC AACCGTCACAAACCAGAGAAGcCGAGGAGAcCTTTCAGCCAACGCCATGTGGGGTCCTGA

GCAGGACCCACCGGAAGTTGGTGCAGCTGCCTAAAGACCGTCCTGGCTGAGAAGAAACAG (SEQ ID NO: 298)

OLIGO start len tm gc % any http://frodo.wi.mit.edu/cgi-bin/primer3/
primer3_www_results_help.cgi - PRIMER_THREE 3' seq (SEQ ID NOs: 299, 300)
LEFT PRIMER    46 18 55.06 50.00 4.00 2.00 AAGGAGAGATTGGGCAAC
RIGHT PRIMER  178 19 54.85 52.63 3.00 1.00 GTTTCTTCTCAGCCAGGAC
SEQUENCE SIZE: 180
INCLUDED REGION SIZE: 180
PRODUCT SIZE: 133, PAIR ANY COMPL: 4.00, PAIR 3' COMPL: 0.00

1 AGGGGCATTCTACAAAACACCCAACCGGTCAAGGTCGCTGAGGCCAAGGAGAGATTGGGC
                    >>>>>>>>>>>>>>

61 AACCGTCACAAACCAGAGAAGcCGAGGAGAcCTTTCAGCCAACGCCATGTGGGGTCCTGA
    >>>

121 GCAGGACCCACCGGAAGTTGGTGCAGCTGCCTAAAGACCGTCCTGGCTGAGAAGAAACAG
                  <<<<<<<<<<<<<<<<<<<

104) Whole sequence ::: rs2838650-rs2838651
TGGCCCTGACCTGCCAGAGCTGTTGGCCTCCAGCTGGCGGGTAAAACCCACGGCCTTCTC AGAACAGGTTTCTCAACACATGAGACAGAACACACCAGACTTCCaAGGGGAACACCTGGA TGGAGCTGGTTACCCAGATcGTTCAACACCGAGGGGCAGCGGCTTGAGGGTCTTTCCACG

AAGGCTTGGATTAACAAGAGGAGCASRGGTCTCTCCAGGATGGGCCCA (SEQ ID NO: 301)

OLIGO start len tm gc % any http://frodo.wi.mit.edu/cgi-bin/primer3/
primer3_www_results_help.cgi - PRIMER_THREE 3' seq (SEQ ID NOs: 302, 303)
LEFT PRIMER    79 20 54.89 50.00 4.00 1.00 CATGAGACAGAACACACCAG
RIGHT PRIMER  199 20 54.61 40.00 5.00 3.00 TCTTGTTAATCCAAGCCTTC
SEQUENCE SIZE: 228
INCLUDED REGION SIZE: 228
PRODUCT SIZE: 121, PAIR ANY COMPL: 4.00, PAIR 3' COMPL: 1.00

1 TGGCCCTGACCTGCCAGAGCTGTTGGCCTCCAGCTGGCGGGTAAAACCCACGGCCTTCTC

61 AGAACAGGTTTCTCAACACATGAGACAGAACACACCAGACTTCCaAGGGGAACACCTGGA
             >>>>>>>>>>>>>>>>>>>>

121 TGGAGCTGGTTACCCAGATcGTTCAACACCGAGGGGCAGCGGCTTGAGGGTCTTTCCACG
                     <

181 AAGGCTTGGATTAACAAGAGGAGCASRGGTCTCTCCAGGATGGGCCCA
           <<<<<<<<<<<<<<<<<<<<

105) Whole sequence ::: rs2838654-rs1296489
CCACCCAGTGTCACGTCACGGCCCCGGCACGCCATCCACGGACCCTGGATGGAGCCCAGC TGCCTCCaGGAGCGCAGTTTAACTACAAAGGAGCCCTGGCTGCCCGCCCCGCCCAGACGC ACTGACCTGTTGTTCTCTGTGGCTGCTGATGGCCCaTCCCCAACCACTGGTGACTCTTCC

CTGGGGCCCCAAGCTCAGCCCCTAACCCCCTGTTGCTGGAAGT (SEQ ID NO: 304)

OLIGO start len tm gc % any http://frodo.wi.mit.edu/cgi-bit/primer3/
primer3_www_results_help.cgi - PRIMER_THREE 3' seq (SEQ ID NOs: 305, 306)
LEFT PRIMER    37 18 62.56 66.67 5.00 2.00 CACGGACCCTGGATGGAG
RIGHT PRIMER  183 18 53.14 55.56 3.00 2.00 CAGGGAAGAGTCACCAGT
SEQUENCE SIZE: 223
INCLUDED REGION SIZE: 223
PRODUCT SIZE: 147, PAIR ANY COMPL: 5.00, PAIR 3' COMPL: 2.00
```

TABLE 2-continued

```
  1 CCACCCAGTGTCACGTCACGGCCCCGGCACGCCATCCACGGACCCTGGATGGAGCCCAGC
                    >>>>>>>>>>>>>>>>>>>

61 TGCCTCCaGGAGCGCAGTTTAACTACAAAGGAGCCCTGGCTGCCCGCCCCGCCCAGACGC

121 ACTGACCTGTTGTTCTCTGTGGCTGCTGATGGCCCaTCCCCAACCACTGGTGACTCTTCC
                                <<<<<<<<<<<<<<

181 CTGGGGCCCCAAGCTCAGCCCCTAACCCCCTGTTGCTGGAAGT
       <<<

106) Whole sequence ::: rs2838659-rs1108261
CAGAGGACTGGGCTGCGGGGTCAGGAATGGGCACACTTCCTAACTGCAGGACACTCTAAG GGCTTTGGTCATGCACACgCAGCCAAGAGAAGGTGTCGCTGaCACACAGCCTTCCAGGAG

CGGACTTGGAGACCTCGCCAAGGACCAGGACTCCCCAGCACTCACACTCCCTTAGGCGCT

GAAGTC (SEQ ID NO: 307)

OLIGO  start  len  tm    gc %  any  http://frodo.wi.mit.edu/cgi-bin/primer3/
primer3_www_results_help.cgi - PRIMER_THREE 3' seq (SEQ ID NOs: 308, 309)
LEFT PRIMER    53  20  55.48  45.00  4.00  2.00 ACTCTAAGGGCTTTGGTCAT
RIGHT PRIMER  175  20  56.02  55.00  3.00  1.00 CTAAGGGAGTGTGAGTGCTG
SEQUENCE SIZE: 186
INCLUDED REGION SIZE: 186
PRODUCT SIZE: 123, PAIR ANY COMPL: 4.00, PAIR 3' COMPL: 1.00

1 CAGAGGACTGGGCTGCGGGGTCAGGAATGGGCACACTTCCTAACTGCAGGACACTCTAAG
                                                    >>>>>>>>

61 GGCTTTGGTCATGCACACgCAGCCAAGAGAAGGTGTCGCTGaCACACAGCCTTCCAGGAG
    >>>>>>>>>>>>

121 CGGACTTGGAGACCTCGCCAAGGACCAGGACTCCCCAGCACTCACACTCCCTTAGGCGCT
                   <<<<<<<<<<<<<<<<<<<<

181 GAAGTC

107) Whole sequence ::: rs585587-rs585601
GAAGAGGACAACACGGGGCTGTCTGCAGAGCACCTGCCACGCGCCAGGCTCTGTGTCCAC AAGCACGGCGGCTGCTCCCACATGACaGAGCTCGTGcGGCAGCTCCAGGACTGTCTGGTG

CCAGAGCCCCAGCTCTCCGCCAGCCCCAGGCCACTGTGCGAGGCCCTCAGTGAAGAGGGG

GCCGT (SEQ ID NO: 310)

OLIGO  start  len  tm    gc %  any  http://frodo.wi.mit.edu/cgi-bin/primer3/
primer3_www_results_help.cgi - PRIMER_THREE 3' seq (SEQ ID NOs: 311, 312)
LEFT PRIMER    42  18  64.78  66.67  5.00  2.00 CGCCAGGCTCTGTGTCCA
RIGHT PRIMER  183  18  60.76  66.67  5.00  3.00 GGCCCCTCTTCACTGAG
SEQUENCE SIZE: 185
INCLUDED REGION SIZE: 185
PRODUCT SIZE: 142, PAIR ANY COMPL: 5.00, PAIR 3' COMPL: 3.00

1 GAAGAGGACAACACGGGGCTGTCTGCAGAGCACCTGCCACGCGCCAGGCTCTGTGTCCAC
                                             >>>>>>>>>>>>>>>>>>

61 AAGCACGGCGGCTGCTCCCACATGACaGAGCTCGTGcGGCAGCTCCAGGACTGTCTGGTG

121 CCAGAGCCCCAGCTCTCCGCCAGCCCCAGGCCACTGTGCGAGGCCCTCAGTGAAGAGGGG
                    <<<<<<<<<<<<<<<

181 GCCGT
       <<<

108) Whole sequence ::: rs9981033-rs4818998
TCTAAATAATGTTAATGATCAAATTTAGTCAGATCTCAATCTTCATATGTTAGTTGCCTT CTTAaTAAATATTCTGTTTTCTTTATCGTTCTTTATTTGTATCTCcACCTTCATTTCTGA

TTAAATTAAGAAGTTTTGTCTCTTCCATTTAATAATTAATGTATTTAATAACC (SEQ ID NO: 313)
```

TABLE 2-continued

```
OLIGO start len tm gc % any http://frodo.wi.mit.edu/cgi-bin/primer3/
primer3_www_results_help.cgi - PRIMER_THREE 3' seq (SEQ ID NOs: 314, 315)
LEFT PRIMER    24 22 51.86 31.82 6.00 2.00 TTTAGTCAGATCTCAATCTTCA
RIGHT PRIMER  149 22 54.02 31.82 4.00 3.00 AATGGAAGAGACAAAACTTCTT
SEQUENCE SIZE: 173
INCLUDED REGION SIZE: 173
PRODUCT SIZE: 126, PAIR ANY COMPL: 5.00, PAIR 3' COMPL: 1.00

1 TCTAAATAATGTTAATGATCAAATTTAGTCAGATCTCAATCTTCATATGTTAGTTGCCTT
              >>>>>>>>>>>>>>>>>>>>>>

61 CTTAaTAAATATTCTGTTTTCTTTATCGTTCTTTATTTGTATCTCcACCTTCATTTCTGA

121 TTAAATTAAGAAGTTTTGTCTCTTCCATTTAATAATTAATGTATTTAATAACC
              <<<<<<<<<<<<<<<<<<<<<<

109) Whole sequence ::: rs2838802-rs2838803
CACACTCCACACTGGCCCCACGCGGGTGGCGAAGGACTCAGCCAGAGCCTGGCAGGATCC TGGGGTGTCTaTTTCCAAGGAATGTTCTGGAAGAAACATACACACATACTTGTTTGCCAG ATTTACCTGTGTGGTcTTCCAGATGAGAAGCAGCCTGTGTCACTCCATAAGGGAGAGTGC

GTGCAGCATTGAGA (SEQ ID NO: 316)

OLIGO start len tm gc % any http://frodo.wi.mit.edu/cgi-bin/primer3/
primer3_www_results_help.cgi - PRIMER_THREE 3' seq (SEQ ID NOs: 317, 318)
LEFT PRIMER    31 18 55.96 61.11 5.00 3.00 GAAGGACTCAGCCAGAGC
RIGHT PRIMER  177 20 55.20 50.00 7.00 3.00 CTCTCCCTTATGGAGTGACA
SEQUENCE SIZE: 194
INCLUDED REGION SIZE: 194
PRODUCT SIZE: 147, PAIR ANY COMPL: 4.00, PAIR 3' COMPL: 0.00

1 CACACTCCACACTGGCCCCACGCGGGTGGCGAAGGACTCAGCCAGAGCCTGGCAGGATCC
                            >>>>>>>>>>>>>>>>>>

61 TGGGGTGTCTaTTTCCAAGGAATGTTCTGGAAGAAACATACACACATACTTGTTTGCCAG

121 ATTTACCTGTGTGGTcTTCCAGATGAGAAGCAGCCTGTGTCACTCCATAAGGGAGAGTGC
                         <<<<<<<<<<<<<<<<<<<<

181 GTGCAGCATTGAGA

110) Whole sequence ::: rs2183596-rs2150452
AAGAAACTCCCAAGGAACGCATTGTCCCAAGTTGCTGCACCAGTCAGTGTACATTCCCAC AAaCAGTGCATGAGAGTTCCTGTTGCTTGTGAAATAAATGGTCAGCATTCAGTGTTGTCA GCTTTTAAAATTTTCTCCTTTCTAGTGGGCATGTAATGGTcTCACATTATAGTTTTAATT

TGCATTTTCCTGGTGACATGTGATACGGAACCTTCCTCCCATGCT (SEQ ID NO: 319)

OLIGO start len tm gc % any http://frodo.wi.mit.edu/cgi-bin/primer3/
primer3_www_results_help.cgi - PRIMER_THREE 3' seq (SEQ ID NOs: 320, 321)
LEFT PRIMER    39 19 50.19 47.37 6.00 2.00 ACCAGTCAGTGTACATTCC
RIGHT PRIMER  190 19 50.12 26.32 4.00 0.00 GGAAAATGCAAATTAAAAC
SEQUENCE SIZE: 225
INCLUDED REGION SIZE: 225
PRODUCT SIZE: 152, PAIR ANY COMPL: 4.00, PAIR 3' COMPL: 1.00

1 AAGAAACTCCCAAGGAACGCATTGTCCCAAGTTGCTGCACCAGTCAGTGTACATTCCCAC
                                 >>>>>>>>>>>>>>>>>>>

61 AAaCAGTGCATGAGAGTTCCTGTTGCTTGTGAAATAAATGGTCAGCATTCAGTGTTGTCA

121 GCTTTTAAAATTTTCTCCTTTCTAGTGGGCATGTAATGGTcTCACATTATAGTTTTAATT
                                 <<<<<<<<

181 TGCATTTTCCTGGTGACATGTGATACGGAACCTTCCTCCCATGCT
           <<<<<<<<

111) Whole sequence ::: rs4599218-rs9978646
GTGCAATTTAATTACAAACGCTTAAATGGGGAGGTCAGGGGCAGAGGGATGATGTCACAA ACACACCCAcGTGTGCTTGGTGCAAAACAGTAAAACAAACAGCAAGAAGgTCCATGAAGG

AAAGATCGCCTCTGTCAGTGGGAGTAATGAGAGTGGCTGATGGACAGGTG (SEQ ID NO: 322)
```

TABLE 2-continued

```
OLIGO        start  len   tm    gc %   any   http://frodo.wi.mit.edu/cgi-bin/primer3/
primer3_www_results_help.cgi - PRIMER_THREE 3' seq (SEQ ID NOs: 323, 324)
LEFT PRIMER     19  20  61.86  55.00  4.00  1.00 CGCTTAAATGGGGAGGTCAG
RIGHT PRIMER   168  20  60.83  60.00  3.00  0.00 CCTGTCCATCAGCCACTCTC
SEQUENCE SIZE: 170
INCLUDED REGION SIZE: 170
PRODUCT SIZE: 150, PAIR ANY COMPL: 5.00, PAIR 3' COMPL: 2.00

1 GTGCAATTTAATTACAAACGCTTAAATGGGGAGGTCAGGGGCAGAGGGATGATGTCACAA
                    >>>>>>>>>>>>>>>>>>>>

61 ACACACCCAcGTGTGCTTGGTGCAAAACAGTAAAACAAACAGCAAGAAGgTCCATGAAGG

121 AAAGATCGCCTCTGTCAGTGGGAGTAATGAGAGTGGCTGATGGACAGGTG
                   <<<<<<<<<<<<<<<<<<<<
```

112) Whole sequence ::: rs11702503-rs3827270
ACGCCAAGCAGGAGATGCCAGACACAGAGTCCATCCTGAGAGAGTCTGTTCCTGTCCAAG CTCAGAAACACAGGAAGCcACCTGTGCTGTAGCAGCACaCGGAGATGCATCCTTTCTGGT

CCACCCCACGGCCCTCATTGCAGTCAGGGATCCTCTCCCAGAAAGTCCCTGCTGCCAGCC

CCTGCCCTT (SEQ ID NO: 325)

```
OLIGO        start  len   tm    gc %   any   http://frodo.wi.mit.edu/cgi-bin/primer3/
primer3_www_results_help.cgi - PRIMER_THREE 3' seq (SEQ ID NOs: 326, 327)
LEFT PRIMER      7  20  62.02  55.00  3.00  0.00 AGCAGGAGATGCCAGACACA
RIGHT PRIMER   125  20  63.37  55.00  5.00  4.00 GGTGGACCAGAAAGGATGCA
SEQUENCE SIZE: 189
INCLUDED REGION SIZE: 189
PRODUCT SIZE: 119, PAIR ANY COMPL: 3.00, PAIR 3' COMPL: 0.00

1 ACGCCAAGCAGGAGATGCCAGACACAGAGTCCATCCTGAGAGAGTCTGTTCCTGTCCAAG
          >>>>>>>>>>>>>>>>>>>>

61 CTCAGAAACACAGGAAGCcACCTGTGCTGTAGCAGCACaCGGAGATGCATCCTTTCTGGT
                               <<<<<<<<<<<<<<<<<<<<

121 CCACCCCACGGCCCTCATTGCAGTCAGGGATCCTCTCCCAGAAAGTCCCTGCTGCCAGCC
         <<<<<

181 CCTGCCCTT
```

113) Whole sequence ::: rs2839084-rs9984302
CATGAGAAAGACTTTGTTCCCATGAGAACAACAAGAGAAACTCAAACAAAATTAAAATTG TACTTTTCTAAAAGACcGGGGTGGGGGTCGTGGTCAGGCAGCaGCATGAAGAAAGCCTTG

AGAACTGAATTCCAGAAAGAAACAAGCATAGGCAAGAAAGAGAGATGACA (SEQ ID NO: 328)

```
OLIGO        start  len   tm    gc %   any   http://frodo.wi.mit.edu/cgi-bin/primer3/
primer3_www_results_help.cgi - PRIMER_THREE 3' seq (SEQ ID NOs: 329, 330)
LEFT PRIMER     19  22  59.21  40.91  4.00  0.00 CCCATGAGAACAACAAGAGAAA
RIGHT PRIMER   162  20  55.46  45.00  4.00  2.00 CTCTTTCTTGCCTATGCTTG
SEQUENCE SIZE: 170
INCLUDED REGION SIZE: 170
PRODUCT SIZE: 144, PAIR ANY COMPL: 5.00, PAIR 3' COMPL: 3.00

1 CATGAGAAAGACTTTGTTCCCATGAGAACAACAAGAGAAACTCAAACAAAATTAAAATTG
                       >>>>>>>>>>>>>>>>>>>>>>

61 TACTTTTCTAAAAGACCGGGGTGGGGGTCGTGGTCAGGCAGCaGCATGAAGAAAGCCTTG

121 AGAACTGAATTCCAGAAAGAAACAAGCATAGGCAAGAAAGAGAGATGACA
                    <<<<<<<<<<<<<<<<<<<<
```

114) Whole sequence ::: rs2249057-rs2249060
AAGATTTAGAACAGCTGAAGCAGCGAGAAAAAACCCAGCATGAGTCaGAACTGGAGCAAC

TGAGGATTTATTTTGAAAAGAAGTTAAGGGATGCTGAGAAAACTTACCAAGAAGACCTAA cCCTGTTACAGCAGAGGCTGCAGGGGGCGAGGGAAGATGCTCTTCTG (SEQ ID NO: 331)

TABLE 2-continued

```
OLIGO      start len  tm    gc %  any  http://frodo.wi.mit.edu/cgi-bin/primer3/
primer3_www_results_help.cgi - PRIMER_THREE 3' seq (SEQ ID NOs: 332, 333)
LEFT PRIMER   12 21 63.07 47.62 6.00 0.00 CAGCTGAAGCAGCGAGAAAAA
RIGHT PRIMER 146 19 66.33 68.42 6.00 3.00 CCCCTGCAGCCTCTGCTGT
SEQUENCE SIZE: 167
INCLUDED REGION SIZE: 167
PRODUCT SIZE: 135, PAIR ANY COMPL: 7.00, PAIR 3' COMPL: 1.00

1 AAGATTTAGAACAGCTGAAGCAGCGAGAAAAAACCCAGCATGAGTCaGAACTGGAGCAAC
                >>>>>>>>>>>>>>>>>>>>>

61 TGAGGATTTATTTTGAAAAGAAGTTAAGGGATGCTGAGAAAACTTACCAAGAAGACCTAA 121 cCCTGTTACAGCAGAGGCTGCAGGGGGCGAGGGAAGATGCTCTTCTG
            <<<<<<<<<<<<<<<<<<<

115) Whole sequence ::: rs2839226-rs2839227
GGGAAACTGACTTGGCTTTTGCAAGGGTCATTGCTTCCTGATGCATGTTTAACTGTCCTG TGTTCACTTTGTTGCcGCAGGTTTTTAGAGGAACGTAAAGAGATCaCCGAGAAATTCAGT

GCGGAACAAGATGCCTTCCTGCAGGAGGCCCAGGAGCAGCATGCCCGTGAGCTG (SEQ ID NO: 334)

OLIGO      start len  tm    gc %  any  http://frodo.wi.mit.edu/cgi-bin/primer3/
primer3_www_results_help.cgi - PRIMER_THREE 3' seq (SEQ ID NOs: 335, 336)
LEFT PRIMER    1 22 64.29 50.00 3.00 2.00 GGGAAACTGACTTGGCTTTTGC
RIGHT PRIMER 135 20 64.63 55.00 3.00 2.00 GGCATCTTGTTCCGCACTGA
SEQUENCE SIZE: 174
INCLUDED REGION SIZE: 174
PRODUCT SIZE: 135, PAIR ANY COMPL: 4.00, PAIR 3' COMPL: 0.00

1 GGGAAACTGACTTGGCTTTTGCAAGGGTCATTGCTTCCTGATGCATGTTTAACTGTCCTG
     >>>>>>>>>>>>>>>>>>>>>>

61 TGTTCACTTTGTTGCcGCAGGTTTTTAGAGGAACGTAAAGAGATCaCCGAGAAATTCAGT
                       <<<<<

121 GCGGAACAAGATGCCTTCCTGCAGGAGGCCCAGGAGCAGCATGCCCGTGAGCTG
           <<<<<<<<<<<<<<<

116) Whole sequence ::: rs10854482-rs2839261
CCCTGCACACTGACCTGCATGCCCTCGTCACCTGCACTCTGCATGCTCACCATCTGACGG ACTCCTGCGAcGGGCATGGGAAGGTCGCCGCCGCCGGCAGCCtTGCGAGCACTTTGGATG

TGTGCACCCGGCATGCCAGGCCCGAGTCAACAGACTGGCCGACCTTGGCGTCCTG (SEQ ID NO: 337)

OLIGO      start len  tm    gc %  any  http://frodo.wi.mit.edu/cgi-bin/primer3/
primer3_www_results_help.cgi - PRIMER_THREE 3' seq (SEQ ID NOs: 338, 339)
LEFT PRIMER   21 20 65.22 65.00 4.00 0.00 GCCCTCGTCACCTGCACTCT
RIGHT PRIMER 168 20 64.77 60.00 5.00 1.00 CCAAGGTCGGCCAGTCTGTT
SEQUENCE SIZE: 175
INCLUDED REGION SIZE: 175
PRODUCT SIZE: 148, PAIR ANY COMPL: 4.00, PAIR 3' COMPL: 0.00

1 CCCTGCACACTGACCTGCATGCCCTCGTCACCTGCACTCTGCATGCTCACCATCTGACGG
                         >>>>>>>>>>>>>>>>>>>>

61 ACTCCTGCGAcGGGCATGGGAAGGTCGCCGCCGCCGGCAGCCtTGCGAGCACTTTGGATG

121 TGTGCACCCGGCATGCCAGGCCCGAGTCAACAGACTGGCCGACCTTGGCGTCCTG
                       <<<<<<<<<<<<<<<<<<<<

117) Whole sequence ::: rs2032111-rs718496
TTTATTGCTGAGTGGTATTCCATTTTATGGGTCCATTATAGTTTATTTGTCCAGACACTT CATGGAAaGACATCAGTGTTTCCtGTTTTTCAATCATAAATTGATGTTTAATTTTAAAAT

TTTGGAATTGTAGAAGAAATGCAATTCTTTTTTCC (SEQ ID NO: 340)

OLIGO      start len  tm    gc %  any  http://frodo.wi.mit.edu/cgi-bin/primer3/
primer3_www_results_help.cgi - PRIMER_THREE 3' seq (SEQ ID NOs: 341, 342)
LEFT PRIMER   28 22 53.65 31.82 4.00 3.00 TGGGTCCATTATAGTTTATTTG
RIGHT PRIMER 143 22 57.46 31.82 4.00 2.00 TGCATTTCTTCTACAATTCCAA
SEQUENCE SIZE: 155
INCLUDED REGION SIZE: 155
PRODUCT SIZE: 116, PAIR ANY COMPL: 5.00, PAIR 3' COMPL: 3.00
```

TABLE 2-continued

```
  1 TTTTATTGCTGAGTGGTATTCCATTTTATGGGTCCATTATAGTTTATTTGTCCAGACACTT
            >>>>>>>>>>>>>>>>>>>>>>

61 CATGGAAaGACATCAGTGTTTCCtGTTTTTCAATCATAAATTGATGTTTAATTTTAAAAT

121 TTTGGAATTGTAGAAGAAATGCAATTCTTTTTTCC
     <<<<<<<<<<<<<<<<<<<<

118) Whole sequence ::: rs2070434-rs2070435
CTTTGGTGCAGAATCATGCTGCAGGCAAGGTGGGCCCACCTCCCTGGAATTTCATCCCCC cCGTCAGTTAAACCCATGGTGGTTTTATTTTCTAGGCCACCTGATCTGGGAGGACCACCT CCAAGAAAAGCAGTCCTaTCGATGAACGGTCTAAGTTATGGTGTTATCAGAGTGGATACT

GAAGAAAAGTTGTCAGTCCTTACTGTTC (SEQ ID NO: 343)

OLIGO start len tm gc % any http://frodo.wi.mit.edu/cgi-bin/primer3/
primer3_www_results_help.cgi - PRIMER_THREE 3' seq (SEQ ID NOs: 344, 345)
LEFT PRIMER    33 20  66.57  60.00  4.00  3.00 GGCCCACCTCCCTGGAATTT
RIGHT PRIMER  176 22  54.26  40.91  4.00  0.00 TCCACTCTGATAACACCATAAC
SEQUENCE SIZE: 208
INCLUDED REGION SIZE: 208
PRODUCT SIZE: 144, PAIR ANY COMPL: 4.00, PAIR 3' COMPL: 1.00

1 CTTTGGTGCAGAATCATGCTGCAGGCAAGGTGGGCCCACCTCCCTGGAATTTCATCCCCC
            >>>>>>>>>>>>>>>>>>>>

61 cCGTCAGTTAAACCCATGGTGGTTTTATTTTCTAGGCCACCTGATCTGGGAGGACCACCT

121 CCAAGAAAAGCAGTCCTaTCGATGAACGGTCTAAGTTATGGTGTTATCAGAGTGGATACT
            <<<<<<<<<<<<<<<<<<<<<

181 GAAGAAAAGTTGTCAGTCCTTACTGTTC
```

Example 6

Determining Whether a Fetus has Trisomy

The number of alleles and the relationship between the number of molecules for the alleles detected for a particular marker are used to determine whether a fetus has trisomy. The results of such an exemplary experiment are depicted in FIG. 3, which is an example of a constant denaturant capillary electrophoresis electropherogram output, where each peak represents the number of molecules of alleles for a marker detected in a sample. As will be appreciated, the marker can be any marker of interest where the maternal genome is heterozygous for that marker and the fetus inherits an allele from the father that is not present in the maternal genome. Although the following description is provided in terms of a single marker, it will be appreciated that in any of the methods described herein, multiple markers may be analyzed, and in some embodiments, multiple markers are analyzed simultaneously in a multiplexed reaction. In specific embodiments, the marker is a tandem SNP, and different alleles detected for this marker represent different haplotypes. In still further embodiments, the tandem SNP represents a short haplotype.

The upper panel of FIG. 3A illustrates the output that would result from a maternal buccal swab, which will comprise maternal nucleic acids but no fetal nucleic acids, In some embodiments, the maternal genome is heterozygous for a particular marker, and in such embodiments, two alleles will be detected in the maternal sample, and these alleles will be present in a 1:1 ratio, which is represented in the electropherogram output as two peaks of equal area.

The lower panel of FIG. 3A illustrates the output that would result from a sample from a baby with trisomy, where the sample comprises fetal nucleic acids but no maternal nucleic acids. The electropherogram output expected from such a sample would show three peaks with areas in a ratio of 1:1:1 or two peaks with areas in a ratio of 2:1. These ratios in the fetal sample result from the fact that a fetus with trisomy would have inherited a total of three alleles for a particular marker: two alleles from the mother and one from the father. If the maternal genome is heterozygous for the marker, three alleles would be detectable in the sample, and all three alleles would be present in the same numbers, resulting in a ratio of 1:1:1, as depicted in the first trace of the lower panel in FIG. 3A (labeled "Baby with trisomy"). If the maternal genome is homozygous for the marker, the fetus with trisomy would still have inherited two alleles from the mother and one from the father, but only two different alleles would be detected in the fetal sample, so only two peaks would be in the output. However, the number of molecules for each allele (represented by the area of the peak) would be different and the peaks would be in a 2:1 ratio, as shown in the last two traces of the lower panel in FIG. 3A. Although the term "peak" is discussed herein in terms of electropherogram output, it will be appreciated that the ratios and relationships described herein apply to the output of any modality that provides information on the number of molecular of an allele present in a sample.

Similar experiments can be conducted on a sample containing both maternal and fetal nucleic acids, and the ratio of the peaks (i.e., the number of molecules for the different alleles of a marker) can be used to determine whether a fetus has trisomy. FIG. 3B shows the electropherogram outputs expected from a sample containing both maternal and fetal nucleic acids, where the fetus has trisomy. In this illustrated example, the maternal genome is heterozygous for the marker, and the paternal genome has an allele that is not present in the maternal genome. The third peak (also referred to herein as the "paternal peak") in the fetal sample output represents the allele inherited from the father (also referred to herein as the "paternal allele"). In the example illustrated in this figure, the paternal allele is not present in the maternal genome. Thus, at informative markers, a sample containing both maternal and fetal nucleic acids will contain three alleles: the two from the maternal genome and the one inherited by the fetus from the paternal genome. The electropherogram output will show larger peaks for the two alleles in the maternal genome than for the allele from the paternal genome, because the sample contains molecules of the two alleles from the maternal genome and from the fetal genome (because the fetus inherited both alleles from the mother). The third peak for the paternal allele will be smaller, because the number of molecules for that allele are only contributed by the fetal nucleic acids in the sample—that allele is not present in the maternal genome, so the overall number of molecules for the paternal allele will be less than the number of molecules for the maternal alleles. The present inventors have found that in such a sample, the number of molecules for the different alleles of the marker will be in a specific ratio if a baby has trisomy. In one embodiment, the ratios will be evident as two equal peaks (the maternal peaks) and a third smaller (paternal) peak, that is, the ratio will be x:peak+x:peak+x (first trace of FIG. 3B), or the ratio will be x:peak:peak+2x, where x is the area of the smallest peak, which represents the number of molecules of the paternal allele, and peak, peak+x, and peak+2x represent the number of molecules of the maternal alleles (which will be the number of molecules of the alleles from the maternal nucleic acids and the number of molecules of the alleles from the fetal nucleic acids inherited from the mother). In a further embodiment, the ratio is about x:peak+x:peak+x or about x:peak:peak+2x if the baby has trisomy. In a still further embodiment, the ratio is approximately x:peak+x: peak+x or about x:peak:peak+2x if the baby has trisomy. As used herein, the term "approximately" encompasses any variation that can still be tolerated by statistical tests to separate the different ratios. Common tests for statistical significance include, among others, t-test, ANOVA, Kruskal-Wallis, Wilcoxon, Mann-Whitney and odds ratio. In some embodiments, approximate ratios mean that there is a variation in a range of ±10% to ±50%. As will be appreciated, such range in variation may include ranges including without limitation ±10% to ±45%, ±15% to ±40%, ±20% to ±35%, and ±25% to ±30%.

FIG. 3C shows the results expected if the fetus is normal (i.e., does not have trisomy). In the situation illustrated in FIG. 3C, the maternal genome is heterozygous for the marker and the fetal allele inherited from the father is not present in the maternal genome. Since the normal fetus will only have inherited one allele from the father and one allele from the mother, the three peaks would have different areas, but these areas would be in a different ratio to each other than would be seen for a fetus with trisomy. For a normal fetus, the areas will in one embodiment be in a ratio of peak:x:peak+x. As in FIG. 3B, "x" is the paternal peak and represents the number of molecules of the allele inherited by the fetus from the father, and "peak" and "peak+x" are the maternal peaks and represent the number of molecules of the alleles in the maternal genome and the number of molecules of the alleles in the fetal genome inherited from the mother. In a further embodiment, the areas will be in a ratio of about peak:x:peak+x. In a still further embodiment, the areas will be in ratio of approximately peak:x:peak+x. Since the fetus only inherited one allele from the mother, one of the maternal peaks would be larger than the other, and the larger peak would be larger by the number "x", because for the fetal nucleic acids in the sample, the number of molecules for the allele inherited from the father will be the same as the number of molecules for the allele inherited from the mother. The third paternal peak thus serves as an internal standard of the number of molecules for alleles present in the fetal genome, and the methods of the present invention do not require a comparison of measurements across different chromosomes. Detection of alleles for a marker on a single chromosome can be used to detect whether the fetus has a chromosomal abnormality. The third (paternal) peak serves as this internal sample whether the fetus has trisomy or not, because this third peak represents only the molecules of the allele the fetus inherited from the father. Since the paternal allele is not present in the maternal genome, the third peak is an internal standard that is independent of the overall concentration of fetal nucleic acids versus maternal nucleic acids in a particular sample.

All publications, patents and patent applications cited herein are incorporated herein by reference. While in the foregoing specification this invention has been described in relation to certain embodiments thereof, and many details have been set forth for purposes of illustration, it will be apparent to those skilled in the art that the invention is susceptible to additional embodiments and that certain of the details described herein may be varied considerably without departing from the basic principles of the invention.

The use of the terms "a" and "an" and "the" and similar referents in the context of describing the invention are to be construed to cover both the singular and the plural, unless otherwise indicated herein or clearly contradicted by context. The terms "comprising," "having," "including," and "containing" are to be construed as open-ended terms (i.e., meaning "including, but not limited to") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for determining whether a fetus has an aneuploidy, said method comprising:
   (a) providing a sample comprising maternal and fetal cell free DNA;
   (b) designing primers directed to alleles of interest comprising tandem single nucleotide polymorphisms for specific chromosomal regions using computer software, wherein the alleles comprise tandem single nucleotide polymorphisms with single nucleotide polymorphisms that are at most 250 basepairs apart;
   (c) enriching the sample for the alleles of interest using the designed primers to create isolated products;
   (d) sequencing the isolated products;
   (e) detecting isolated products from the chromosomal region of interests that comprise at least three different alleles, wherein each of the three different alleles of the chromosomal regions comprise different haplotypes of the tandem SNP;
   (f) quantifying the detected isolated products to calculate a haplotype ratio for the alleles of interest at the chromosomal regions of interest;
   (g) determining whether the fetus has an aneuploidy based on the calculated haplotype ratios.

2. The method of claim 1, wherein the single nucleotide polymorphisms in the tandem single nucleotide polymorphism are at most 100 nucleotides apart.

3. The method of claim 2, wherein the single nucleotide polymorphisms in the tandem single nucleotide polymorphism are at most 75 nucleotides apart.

4. The method of claim 3, wherein the single nucleotide polymorphisms in the tandem single nucleotide polymorphism are at most 50 nucleotides apart.

5. The method of claim 1, wherein the alleles of interest are enriched through amplification.

6. The method of claim 5, wherein the primers are amplification primers used to enrich the alleles of interest.

7. The method of claim 1, wherein the aneuploidy is a trisomy.

8. The method of claim 1, wherein the aneuploidy is a monosomy.

* * * * *

SEQUENCE LISTING

<160> NUMBER OF SEQ ID NOS: 357

<210> SEQ ID NO 1
<211> LENGTH: 127
<212> TYPE: DNA
<213> ORGANISM: Homo sapiens

<400> SEQUENCE: 1
aacaaatctt catcttggaa tagcctgtga gaatgcctaa tcatctacga atgttacttt    60
ggcaccatct actggacaga ttaaataaca accaactcac tgtggattag acctacttct   120
atttcag                                                             127

<210> SEQ ID NO 2
<211> LENGTH: 20
<212> TYPE: DNA
<213> ORGANISM: Homo sapiens

<400> SEQUENCE: 2
atagcctgtg agaatgccta                                                20

<210> SEQ ID NO 3
<211> LENGTH: 20
<212> TYPE: DNA
<213> ORGANISM: Homo sapiens

<400> SEQUENCE: 3
atccacagtg agttggttgt                                                20

<210> SEQ ID NO 4
<211> LENGTH: 84
<212> TYPE: DNA
<213> ORGANISM: Homo sapiens

<400> SEQUENCE: 4
ttcctggaaa acaaaagtat ttctttcata gcccagctag catgataaat cagcgagtca    60
gaattctagc tttgttgtaa ggtt                                           84

<210> SEQ ID NO 5
<211> LENGTH: 20
<212> TYPE: DNA
<213> ORGANISM: Homo sapiens

<400> SEQUENCE: 5
tcctggaaaa caaaagtatt                                                20

<210> SEQ ID NO 6
<211> LENGTH: 21
<212> TYPE: DNA
<213> ORGANISM: Homo sapiens

<400> SEQUENCE: 6
aaccttacaa caaagctaga a                                              21

<210> SEQ ID NO 7
<211> LENGTH: 71
<212> TYPE: DNA
<213> ORGANISM: Homo sapiens

-continued

<400> SEQUENCE: 7
cactaagcct tggggatcca gctgcttaag gactaagacc gtatctagct ccttttagta    60
tttccacagc a                                                        71

<210> SEQ ID NO 8
<211> LENGTH: 20
<212> TYPE: DNA
<213> ORGANISM: Homo sapiens

<400> SEQUENCE: 8
actaagcctt ggggatccag                                               20

<210> SEQ ID NO 9
<211> LENGTH: 21
<212> TYPE: DNA
<213> ORGANISM: Homo sapiens

<400> SEQUENCE: 9
tgctgtggaa atactaaaag g                                             21

<210> SEQ ID NO 10
<211> LENGTH: 155
<212> TYPE: DNA
<213> ORGANISM: Homo sapiens

<400> SEQUENCE: 10
tcctccagag gtaatcctgt gatcagcact aacaccacat accagccctt tcatcagctt    60
gttggagaag catctttact tcccgccaag cagtgaccta gataccatct cacaccagtt   120
agaatcagga tcattaaaaa gtcaagaaaa aacag                             155

<210> SEQ ID NO 11
<211> LENGTH: 20
<212> TYPE: DNA
<213> ORGANISM: Homo sapiens

<400> SEQUENCE: 11
ctccagaggt aatcctgtga                                               20

<210> SEQ ID NO 12
<211> LENGTH: 21
<212> TYPE: DNA
<213> ORGANISM: Homo sapiens

<400> SEQUENCE: 12
tggtgtgaga tggtatctag g                                             21

<210> SEQ ID NO 13
<211> LENGTH: 146
<212> TYPE: DNA
<213> ORGANISM: Homo sapiens

<400> SEQUENCE: 13
tccaagtata atccatgaat cttgtttaaa tatagatcaa ataaccact ataccaaaaa    60 catcaaaaga caactgggta aattttttaa atgactagct atttgatgtt aaggaagtaa   120
tgttactctc ttatatacaa tttgaa                                       146

<210> SEQ ID NO 14
<211> LENGTH: 22
<212> TYPE: DNA
<213> ORGANISM: Homo sapiens

```
<400> SEQUENCE: 14
gtataatcca tgaatcttgt tt                                              22

<210> SEQ ID NO 15
<211> LENGTH: 22
<212> TYPE: DNA
<213> ORGANISM: Homo sapiens

<400> SEQUENCE: 15
ttcaaattgt atataagaga gt                                              22

<210> SEQ ID NO 16
<211> LENGTH: 132
<212> TYPE: DNA
<213> ORGANISM: Homo sapiens

<400> SEQUENCE: 16
atggaaccga aacttcaagt agtttcatac gtatcacatt gacagttttc tctaagtttt     60
ctggtcttat gactcgttgt ttcattatta aaactgtgcc agtgtatgca tagggcttag    120 aaattttta at                                                        132

<210> SEQ ID NO 17
<211> LENGTH: 18
<212> TYPE: DNA
<213> ORGANISM: Homo sapiens

<400> SEQUENCE: 17
atggaaccga aacttcaa                                                   18

<210> SEQ ID NO 18
<211> LENGTH: 22
<212> TYPE: DNA
<213> ORGANISM: Homo sapiens

<400> SEQUENCE: 18
ttaataatga acaacgagt ca                                               22

<210> SEQ ID NO 19
<211> LENGTH: 157
<212> TYPE: DNA
<213> ORGANISM: Homo sapiens

<400> SEQUENCE: 19
acaggatcct tcctgaagac accaccttgg ggagggtgaa ggataaagaa tttgatcaga     60
aatcaagggt ggtgagatac atgttaagga tgaataaact ggcctttag gattcttgct    120 aaaattagac aatgcagagg caaccacaga gtccaag                            157

<210> SEQ ID NO 20
<211> LENGTH: 19
<212> TYPE: DNA
<213> ORGANISM: Homo sapiens

<400> SEQUENCE: 20
ttcctgaaga caccacctt                                                  19

<210> SEQ ID NO 21
<211> LENGTH: 18
<212> TYPE: DNA
<213> ORGANISM: Homo sapiens

<400> SEQUENCE: 21
```

```
cttggactct gtggttgc                                                     18
```

<210> SEQ ID NO 22
<211> LENGTH: 173
<212> TYPE: DNA
<213> ORGANISM: Homo sapiens

<400> SEQUENCE: 22

```
aatttccatt aaatcttgtt cgttgcttta ctgaggcact gaagttacca atgttccact       60
ggttgacctg cggggctatc tctaggttat gttactccag aaaatgaatt gtgtataaaa      120
gaggccttgg aggaaggcgt tttattcaca tcagttgttt tgcacattgc tta             173
```

<210> SEQ ID NO 23
<211> LENGTH: 20
<212> TYPE: DNA
<213> ORGANISM: Homo sapiens

<400> SEQUENCE: 23

```
actgaggcac tgaagttacc                                                   20
```

<210> SEQ ID NO 24
<211> LENGTH: 20
<212> TYPE: DNA
<213> ORGANISM: Homo sapiens

<400> SEQUENCE: 24

```
taagcaatgt gcaaaacaac                                                   20
```

<210> SEQ ID NO 25
<211> LENGTH: 191
<212> TYPE: DNA
<213> ORGANISM: Homo sapiens

<400> SEQUENCE: 25

```
tcggtttcag caggaaagtt atttttaata acttccctgt atttcttggt ttcagttatt       60
aattaactca ttaatgctaa actttgtgat cctaggttaa aaaacatatt caagatagct      120
tcagaatgtt tggtatacaa gtaggtctgg ctaaatataa gtgttagctt tctcaagcat      180
ctaaatgctg g                                                           191
```

<210> SEQ ID NO 26
<211> LENGTH: 20
<212> TYPE: DNA
<213> ORGANISM: Homo sapiens

<400> SEQUENCE: 26

```
gcaggaaagt tattttttaat                                                  20
```

<210> SEQ ID NO 27
<211> LENGTH: 21
<212> TYPE: DNA
<213> ORGANISM: Homo sapiens

<400> SEQUENCE: 27

```
tgcttgagaa agctaacact t                                                 21
```

<210> SEQ ID NO 28
<211> LENGTH: 166
<212> TYPE: DNA
<213> ORGANISM: Homo sapiens

<400> SEQUENCE: 28

```
aagttatttt taataacttc cctgtatttc ttggtttcag ttattaatta actcattaat    60
gctaaacttt gtgatcctag gttaaaaaac atattcaaga tagcttcaga atgtttggta   120
tacaagtagg tctggctaaa tataagtgtt agctttctca agcatc                  166
```

<210> SEQ ID NO 29
<211> LENGTH: 20
<212> TYPE: DNA
<213> ORGANISM: Homo sapiens

<400> SEQUENCE: 29

```
atttttaata acttccctgt                                                20
```

<210> SEQ ID NO 30
<211> LENGTH: 20
<212> TYPE: DNA
<213> ORGANISM: Homo sapiens

<400> SEQUENCE: 30

```
cacttatatt tagccagacc                                                20
```

<210> SEQ ID NO 31
<211> LENGTH: 152
<212> TYPE: DNA
<213> ORGANISM: Homo sapiens

<400> SEQUENCE: 31

```
attcattgtg tagaaagtgc ctgactcagt gtttggaaat tgtctgactt ttcctcatat    60
atagtgtggt ttcatgttat tgtatataag aactgacatg aactctgttt acaataatct  120
cccagtgcca taaagaccat aataaataat at                                 152
```

<210> SEQ ID NO 32
<211> LENGTH: 20
<212> TYPE: DNA
<213> ORGANISM: Homo sapiens

<400> SEQUENCE: 32

```
cagtgtttgg aaattgtctg                                                20
```

<210> SEQ ID NO 33
<211> LENGTH: 20
<212> TYPE: DNA
<213> ORGANISM: Homo sapiens

<400> SEQUENCE: 33

```
ggcactggga gattattgta                                                20
```

<210> SEQ ID NO 34
<211> LENGTH: 163
<212> TYPE: DNA
<213> ORGANISM: Homo sapiens

<400> SEQUENCE: 34

```
cactgggtcc tgttgttaag tacacataat accacacagg agaaaatcag gctaattgta    60
aatgggcaac ctacttaatt gtttcattaa aaagcataca gattacattt acactatagc  120
tagtcttgtt tgttttttta ttttgcaaaa gtaattacgg ccc                     163
```

<210> SEQ ID NO 35
<211> LENGTH: 20
<212> TYPE: DNA
<213> ORGANISM: Homo sapiens

```
<400> SEQUENCE: 35
tcctgttgtt aagtacacat                                              20

<210> SEQ ID NO 36
<211> LENGTH: 18
<212> TYPE: DNA
<213> ORGANISM: Homo sapiens

<400> SEQUENCE: 36
gggccgtaat tacttttg                                                18

<210> SEQ ID NO 37
<211> LENGTH: 108
<212> TYPE: DNA
<213> ORGANISM: Homo sapiens

<400> SEQUENCE: 37
ctactcagta ggcactttgt gtctagaaac ttctgtgtca acggttttcc ctctctctgg   60
aattcatcag gacagaagtg attggtgtgg tggaagaggg ttgtgsta              108

<210> SEQ ID NO 38
<211> LENGTH: 21
<212> TYPE: DNA
<213> ORGANISM: Homo sapiens

<400> SEQUENCE: 38
actcagtagg cactttgtgt c                                            21

<210> SEQ ID NO 39
<211> LENGTH: 18
<212> TYPE: DNA
<213> ORGANISM: Homo sapiens

<400> SEQUENCE: 39
tcttccacca caccaatc                                                18

<210> SEQ ID NO 40
<211> LENGTH: 144
<212> TYPE: DNA
<213> ORGANISM: Homo sapiens

<400> SEQUENCE: 40
tggcttttca aaggtaaaat ttactaagtg tattaatatt ttaccaattt ccagccagga   60
gagtatgaat gttgcattat tacattgctt tgaaacaaag cattagtctt aattcagaag  120
tttaaattca gatgttaacg ttgc                                        144

<210> SEQ ID NO 41
<211> LENGTH: 19
<212> TYPE: DNA
<213> ORGANISM: Homo sapiens

<400> SEQUENCE: 41
tggcttttca aaggtaaaa                                               19

<210> SEQ ID NO 42
<211> LENGTH: 21
<212> TYPE: DNA
<213> ORGANISM: Homo sapiens

<400> SEQUENCE: 42
gcaacgttaa catctgaatt t                                            21
```

```
<210> SEQ ID NO 43
<211> LENGTH: 110
<212> TYPE: DNA
<213> ORGANISM: Homo sapiens

<400> SEQUENCE: 43
taagtattga agaaaggaga atttaaatta cttcatatac ctgataaagg aaaacatata      60
caaggcaaat aaacatctta gatcatgaca tataaaataa tagattatta                110

<210> SEQ ID NO 44
<211> LENGTH: 20
<212> TYPE: DNA
<213> ORGANISM: Homo sapiens

<400> SEQUENCE: 44
ttgaagaaag gagaatttaa                                                  20

<210> SEQ ID NO 45
<211> LENGTH: 22
<212> TYPE: DNA
<213> ORGANISM: Homo sapiens

<400> SEQUENCE: 45
attttatatg tcatgatcta ag                                               22

<210> SEQ ID NO 46
<211> LENGTH: 165
<212> TYPE: DNA
<213> ORGANISM: Homo sapiens

<400> SEQUENCE: 46
tgcagagatt acaggtgtga gccaccgtgc ccagcctcat aaccgtttca actactttt       60 cacttgacaa gcagatgtga agttaacaaa gtcacccata tttgaaataa agatagtata    120
ttcctggggt aggcagaggc agttgaggat catgaaataa ctatg                    165

<210> SEQ ID NO 47
<211> LENGTH: 19
<212> TYPE: DNA
<213> ORGANISM: Homo sapiens

<400> SEQUENCE: 47
agagattaca ggtgtgagc                                                   19

<210> SEQ ID NO 48
<211> LENGTH: 19
<212> TYPE: DNA
<213> ORGANISM: Homo sapiens

<400> SEQUENCE: 48
atgatcctca actgcctct                                                   19

<210> SEQ ID NO 49
<211> LENGTH: 178
<212> TYPE: DNA
<213> ORGANISM: Homo sapiens

<400> SEQUENCE: 49
tgcaatgaaa ctcaaaagag aaaagttaac aggtgcaaaa ggtagtttta ttataaaagg      60
agggtaggca acaagaatat gtttaatttt tcttcctttt catgagtaag gacaagagtg    120
tcatatatgt gaatattttt atttaatttt aagtagaaat ctgttttaa aatatggg       178
```

```
<210> SEQ ID NO 50
<211> LENGTH: 20
<212> TYPE: DNA
<213> ORGANISM: Homo sapiens

<400> SEQUENCE: 50
tgaaactcaa aagagaaaag                                                     20

<210> SEQ ID NO 51
<211> LENGTH: 20
<212> TYPE: DNA
<213> ORGANISM: Homo sapiens

<400> SEQUENCE: 51
acagatttct acttaaaatt                                                     20

<210> SEQ ID NO 52
<211> LENGTH: 102
<212> TYPE: DNA
<213> ORGANISM: Homo sapiens

<400> SEQUENCE: 52
ccaccattca tcaaaacttt gatactggac tcaattgtga atttgacttg aaatttgata         60
atgcttttgt tttactgttc tgctcagcaa aatagtacat gt                           102

<210> SEQ ID NO 53
<211> LENGTH: 20
<212> TYPE: DNA
<213> ORGANISM: Homo sapiens

<400> SEQUENCE: 53
caaaactttg atactggact                                                     20

<210> SEQ ID NO 54
<211> LENGTH: 19
<212> TYPE: DNA
<213> ORGANISM: Homo sapiens

<400> SEQUENCE: 54
acatgtacta ttttgctga                                                      19

<210> SEQ ID NO 55
<211> LENGTH: 166
<212> TYPE: DNA
<213> ORGANISM: Homo sapiens

<400> SEQUENCE: 55
gcctgcataa agtgaggatg gtgtagtaat tgggtatctc cagttataaa cacaaaaagc         60
atgatagagc tgggactgtg attgcaggaa agcaatagtc actccaaaag gagatcctca        120
tgatatgaat acggaagaaa caatatttcc tgctaatgta gtagcc                       166

<210> SEQ ID NO 56
<211> LENGTH: 20
<212> TYPE: DNA
<213> ORGANISM: Homo sapiens

<400> SEQUENCE: 56
cctgcataaa gtgaggatgg                                                     20

<210> SEQ ID NO 57
<211> LENGTH: 21
<212> TYPE: DNA
```

```
<213> ORGANISM: Homo sapiens

<400> SEQUENCE: 57
tgaggatctc cttttggagt g                                              21

<210> SEQ ID NO 58
<211> LENGTH: 154
<212> TYPE: DNA
<213> ORGANISM: Homo sapiens

<400> SEQUENCE: 58
gcaaaggggt actctatgta atgaacatga cctggcagta ctgacatctc ctgagggact    60
gttagaagtg cagactcttg tatcttttct caagtctatg aaatctagac ttcattttaa   120
caagatgacc cgatatttac atacacatta aagt                               154

<210> SEQ ID NO 59
<211> LENGTH: 20
<212> TYPE: DNA
<213> ORGANISM: Homo sapiens

<400> SEQUENCE: 59
gcaaaggggt actctatgta                                                20

<210> SEQ ID NO 60
<211> LENGTH: 20
<212> TYPE: DNA
<213> ORGANISM: Homo sapiens

<400> SEQUENCE: 60
tatcgggtca tcttgttaaa                                                20

<210> SEQ ID NO 61
<211> LENGTH: 174
<212> TYPE: DNA
<213> ORGANISM: Homo sapiens

<400> SEQUENCE: 61
gtatctaaca aagctctgtc caaaattttg aatttctcgt taaaagcatc atgattatag    60
aacagaggtt acaatcaatt attcagtcac acaatcactc tcatcagtca ttaaggtgcg   120
tacctggtgt tccagttatt cagtgtggta taacaaacta cctggaactt aatg         174

<210> SEQ ID NO 62
<211> LENGTH: 22
<212> TYPE: DNA
<213> ORGANISM: Homo sapiens

<400> SEQUENCE: 62
tctaacaaag ctctgtccaa aa                                             22

<210> SEQ ID NO 63
<211> LENGTH: 21
<212> TYPE: DNA
<213> ORGANISM: Homo sapiens

<400> SEQUENCE: 63
ccacactgaa taactggaac a                                              21

<210> SEQ ID NO 64
<211> LENGTH: 202
<212> TYPE: DNA
<213> ORGANISM: Homo sapiens
```

-continued

```
<400> SEQUENCE: 64
agagtggtta agtgacttga tcaattcctc aggtggggat tcaagctctt aaagctgtag    60
actatgtcgt ccaaacaaac actgacatga atatgacttc caataggcaa gaaaagaggc   120
ctaggtcgag atactgcaag acatgcaagc aatctagtaa tggcataaaa cctgctatcc   180
gaattggcta aaattatgta tt                                            202

<210> SEQ ID NO 65
<211> LENGTH: 20
<212> TYPE: DNA
<213> ORGANISM: Homo sapiens

<400> SEQUENCE: 65
ggtggggatt caagctctta                                                20

<210> SEQ ID NO 66
<211> LENGTH: 22
<212> TYPE: DNA
<213> ORGANISM: Homo sapiens

<400> SEQUENCE: 66
ggatagcagg ttttatgcca tt                                             22

<210> SEQ ID NO 67
<211> LENGTH: 156
<212> TYPE: DNA
<213> ORGANISM: Homo sapiens

<400> SEQUENCE: 67
ttctttctca cacaatgggt tccattccca ctactactcc attcaaattg aagtgccttc    60
aatgattatt aaaaaactct ctttaaaata gctcacgtaa ccttacatcc tttgactgag   120
gctcaactca tgtcaatgct tcagtatcaa cttttc                             156

<210> SEQ ID NO 68
<211> LENGTH: 21
<212> TYPE: DNA
<213> ORGANISM: Homo sapiens

<400> SEQUENCE: 68
aatgggttcc attcccacta c                                              21

<210> SEQ ID NO 69
<211> LENGTH: 20
<212> TYPE: DNA
<213> ORGANISM: Homo sapiens

<400> SEQUENCE: 69
tgagcctcag tcaaaggatg                                                20

<210> SEQ ID NO 70
<211> LENGTH: 202
<212> TYPE: DNA
<213> ORGANISM: Homo sapiens

<400> SEQUENCE: 70
atttgtaata acatttagta agtatttatt tgaggagttt gaattttgtt cttgtttatc    60
ttgttctctt tcttcgtaga ttagttggtg ttaacatcaa taggataacc ctttctttca   120
gcatatgtga atgaaataaa ccaattattg ccactttcca ggttaaccag aatatacata   180
gatacgagga cagtggactg tt                                            202
```

```
<210> SEQ ID NO 71
<211> LENGTH: 22
<212> TYPE: DNA
<213> ORGANISM: Homo sapiens

<400> SEQUENCE: 71
ttgaggagtt tgaattttgt tc                                              22

<210> SEQ ID NO 72
<211> LENGTH: 20
<212> TYPE: DNA
<213> ORGANISM: Homo sapiens

<400> SEQUENCE: 72
aacctggaaa gtggcaataa                                                 20

<210> SEQ ID NO 73
<211> LENGTH: 171
<212> TYPE: DNA
<213> ORGANISM: Homo sapiens

<400> SEQUENCE: 73
tagggcagag agagcaagca agctctctac cttctcatat aagggcacta atcccaccat     60
gaaggcgcca ctgtcatgac ctgattatgt cacaaagacc ccggggcaaa tattaccact    120
gtgaggagta cagttttagc atgtgaattt tggaagaaca caaacattta g             171

<210> SEQ ID NO 74
<211> LENGTH: 21
<212> TYPE: DNA
<213> ORGANISM: Homo sapiens

<400> SEQUENCE: 74
gcaagcaagc tctctacctt c                                               21

<210> SEQ ID NO 75
<211> LENGTH: 22
<212> TYPE: DNA
<213> ORGANISM: Homo sapiens

<400> SEQUENCE: 75
tgttcttcca aaattcacat gc                                              22

<210> SEQ ID NO 76
<211> LENGTH: 195
<212> TYPE: DNA
<213> ORGANISM: Homo sapiens

<400> SEQUENCE: 76
attctaattt taaatatcat tgatgtagaa cattctattt cactattcct tcattttatt     60
attatgggaa attatataca gttctccaga tttttaaagc cttgctaaca tgttttaagt    120
cacacaaata ttctcctgtg ggaaaatgac agtaatttag tgtgcaacaa ttatatagaa    180
ctatttttca aactt                                                     195

<210> SEQ ID NO 77
<211> LENGTH: 21
<212> TYPE: DNA
<213> ORGANISM: Homo sapiens

<400> SEQUENCE: 77
atttcactat tccttcattt t                                               21
```

<210> SEQ ID NO 78
<211> LENGTH: 22
<212> TYPE: DNA
<213> ORGANISM: Homo sapiens

<400> SEQUENCE: 78
taattgttgc acactaaatt ac                                             22

<210> SEQ ID NO 79
<211> LENGTH: 138
<212> TYPE: DNA
<213> ORGANISM: Homo sapiens

<400> SEQUENCE: 79
actgtcatgg acttaaacaa ttgtctttga attgtctttt ttcatacttt tatttgcatc    60
tttccactaa aaagatggca caaagtaatc ctagtttaca ttttttacca tgtaattcca   120
tattactttt tcctgaaa                                                 138

<210> SEQ ID NO 80
<211> LENGTH: 20
<212> TYPE: DNA
<213> ORGANISM: Homo sapiens

<400> SEQUENCE: 80
actgtcatgg acttaaacaa                                                20

<210> SEQ ID NO 81
<211> LENGTH: 22
<212> TYPE: DNA
<213> ORGANISM: Homo sapiens

<400> SEQUENCE: 81
ttcaggaaaa agtaatatgg aa                                             22

<210> SEQ ID NO 82
<211> LENGTH: 119
<212> TYPE: DNA
<213> ORGANISM: Homo sapiens

<400> SEQUENCE: 82
aaagaaaaaa aagccacaga aatcagtcct agagaaaacc gatctatgag ctgcctgaaa    60
ataattataa aataactatc ataaaaatgc ccagtgagat ataagaaaac acagacaac    119

<210> SEQ ID NO 83
<211> LENGTH: 21
<212> TYPE: DNA
<213> ORGANISM: Homo sapiens

<400> SEQUENCE: 83
aaaaagccac agaaatcagt c                                              21

<210> SEQ ID NO 84
<211> LENGTH: 22
<212> TYPE: DNA
<213> ORGANISM: Homo sapiens

<400> SEQUENCE: 84
ttcttatatc tcactgggca tt                                             22

<210> SEQ ID NO 85
<211> LENGTH: 143
<212> TYPE: DNA

-continued

<213> ORGANISM: Homo sapiens

<400> SEQUENCE: 85
caaggtcaga gaagttatct tggatggtag aagagaagaa aggagaagaa aggataagca    60
gaaaatcaaa aagggcataa aaaaattact ggggaaaata attcttagtc actcaccatt   120
tcttatgttt gtgaaaacag aaa                                            143

<210> SEQ ID NO 86
<211> LENGTH: 22
<212> TYPE: DNA
<213> ORGANISM: Homo sapiens

<400> SEQUENCE: 86
ggatggtaga agagaagaaa gg                                              22

<210> SEQ ID NO 87
<211> LENGTH: 22
<212> TYPE: DNA
<213> ORGANISM: Homo sapiens

<400> SEQUENCE: 87
tcacaaacat aagaaatggt ga                                              22

<210> SEQ ID NO 88
<211> LENGTH: 136
<212> TYPE: DNA
<213> ORGANISM: Homo sapiens

<400> SEQUENCE: 88
gaccacaatt cacaaatgca aagatgcaga accaacctaa gtggccactg actaatgaga    60
ggataaagaa gatgtggcat atatatatca gggactacta ctcagccatt acaaggaaca   120
aaataatgtc ttttgc                                                    136

<210> SEQ ID NO 89
<211> LENGTH: 20
<212> TYPE: DNA
<213> ORGANISM: Homo sapiens

<400> SEQUENCE: 89
tgcaaagatg cagaaccaac                                                 20

<210> SEQ ID NO 90
<211> LENGTH: 22
<212> TYPE: DNA
<213> ORGANISM: Homo sapiens

<400> SEQUENCE: 90
ttttgttcct tgtaatggct ga                                              22

<210> SEQ ID NO 91
<211> LENGTH: 160
<212> TYPE: DNA
<213> ORGANISM: Homo sapiens

<400> SEQUENCE: 91
gaccacaatt cacaaatgca aagatgcaga accaacctaa gtggccactg actaatgaga    60
ggataaagaa gatgtggcat atatacatca gggactactt ctcagccatt acaaggaaca   120
aaataatgtc ttttgcaaca acttggatag agctggaggc                          160

<210> SEQ ID NO 92

-continued

```
<211> LENGTH: 20
<212> TYPE: DNA
<213> ORGANISM: Homo sapiens

<400> SEQUENCE: 92
tgcaaagatg cagaaccaac                                              20

<210> SEQ ID NO 93
<211> LENGTH: 21
<212> TYPE: DNA
<213> ORGANISM: Homo sapiens

<400> SEQUENCE: 93
gcctccagct ctatccaagt t                                            21

<210> SEQ ID NO 94
<211> LENGTH: 160
<212> TYPE: DNA
<213> ORGANISM: Homo sapiens

<400> SEQUENCE: 94
aatcctagac cttggattgc aagagactcc ttaatatctt cccatgtcca catttccttc   60
acatagtttg aatgtggctt ctattatata cagatacaag attcaaatcc aacctctatg  120
atgactggtc ttgtgaataa gcagaagagg cactaacaat                        160

<210> SEQ ID NO 95
<211> LENGTH: 22
<212> TYPE: DNA
<213> ORGANISM: Homo sapiens

<400> SEQUENCE: 95
ccttaatatc ttcccatgtc ca                                           22

<210> SEQ ID NO 96
<211> LENGTH: 22
<212> TYPE: DNA
<213> ORGANISM: Homo sapiens

<400> SEQUENCE: 96
attgttagtg cctcttctgc tt                                           22

<210> SEQ ID NO 97
<211> LENGTH: 162
<212> TYPE: DNA
<213> ORGANISM: Homo sapiens

<400> SEQUENCE: 97
aagagaagtg aggtcagcag ctgcaagcca cctccgtcat ttagaaaagc ttcatgatgt   60
agtgtgtcgt ttcgatgtga cactgtctca cagagttaaa atgatgttaa ggaactgttc  120
aatggaaatt tagaaatttc tcttttctc aattttagtg ta                      162

<210> SEQ ID NO 98
<211> LENGTH: 20
<212> TYPE: DNA
<213> ORGANISM: Homo sapiens

<400> SEQUENCE: 98
gagaagtgag gtcagcagct                                              20

<210> SEQ ID NO 99
<211> LENGTH: 22
<212> TYPE: DNA
```

<213> ORGANISM: Homo sapiens

<400> SEQUENCE: 99
tttctaaatt tccattgaac ag                                              22

<210> SEQ ID NO 100
<211> LENGTH: 160
<212> TYPE: DNA
<213> ORGANISM: Homo sapiens

<400> SEQUENCE: 100
atggctgaat agtattccct tgtgtatata tctatttatc cttttattca ttgatggaca     60
cttaggctga ttttctctct tctcatggct ggcttctcat cacccttttgg tcctcctgta   120 tcctcgtgta ataaagctct tccccaatat ctcgatagat                          160

<210> SEQ ID NO 101
<211> LENGTH: 22
<212> TYPE: DNA
<213> ORGANISM: Homo sapiens

<400> SEQUENCE: 101
ggctgaatag tattcccttg tg                                              22

<210> SEQ ID NO 102
<211> LENGTH: 20
<212> TYPE: DNA
<213> ORGANISM: Homo sapiens

<400> SEQUENCE: 102
tcgagatatt ggggaagagc                                                 20

<210> SEQ ID NO 103
<211> LENGTH: 199
<212> TYPE: DNA
<213> ORGANISM: Homo sapiens

<400> SEQUENCE: 103
cattttaact tgattacctc cacaaagact attccagaat aaggttatgt tctgaggtat     60
taggggttac aacttcaaca tatgaatttt gagtggacac aattcaaccc atagcacctc   120
cgtgtaagag ctgggaaggg aaagtggcta agttgtgcaa atgtgcacat tggttggaga   180
tgattaactt ctggcatgt                                                 199

<210> SEQ ID NO 104
<211> LENGTH: 22
<212> TYPE: DNA
<213> ORGANISM: Homo sapiens

<400> SEQUENCE: 104
cctccacaaa gactattcca ga                                              22

<210> SEQ ID NO 105
<211> LENGTH: 20
<212> TYPE: DNA
<213> ORGANISM: Homo sapiens

<400> SEQUENCE: 105
cactttccct tcccagctct                                                 20

<210> SEQ ID NO 106
<211> LENGTH: 157
<212> TYPE: DNA

```
<213> ORGANISM: Homo sapiens

<400> SEQUENCE: 106 aggggaaat tggcaatctg attctaaaat tcatacggaa aaaacaatg gagttagaat    60 aactaaaaca agtccgaaaa agaaaaagaa atggaggact aatgctacct gatttcaagt  120
cttatcttat aaatctacat caataaagga caagttg                          157

<210> SEQ ID NO 107
<211> LENGTH: 20
<212> TYPE: DNA
<213> ORGANISM: Homo sapiens

<400> SEQUENCE: 107
gaaattggca atctgattct                                              20

<210> SEQ ID NO 108
<211> LENGTH: 21
<212> TYPE: DNA
<213> ORGANISM: Homo sapiens

<400> SEQUENCE: 108
caacttgtcc tttattgatg t                                            21

<210> SEQ ID NO 109
<211> LENGTH: 173
<212> TYPE: DNA
<213> ORGANISM: Homo sapiens

<400> SEQUENCE: 109
tctgtgtttg tctatgttga taaaacattg aaatgccaaa tagctcaaag gtcattcact   60
taagaaatct aagtactgat aacatcttag ccccgattct tcataggcat tgttaagcct  120
attataattt tggttcagag agaaggtaaa ctatattcca gacaggcata taa          173

<210> SEQ ID NO 110
<211> LENGTH: 22
<212> TYPE: DNA
<213> ORGANISM: Homo sapiens

<400> SEQUENCE: 110
ctatgttgat aaaacattga aa                                            22

<210> SEQ ID NO 111
<211> LENGTH: 20
<212> TYPE: DNA
<213> ORGANISM: Homo sapiens

<400> SEQUENCE: 111
gcctgtctgg aatatagttt                                              20

<210> SEQ ID NO 112
<211> LENGTH: 126
<212> TYPE: DNA
<213> ORGANISM: Homo sapiens

<400> SEQUENCE: 112
tgcagggcat ataatctaag ctgtaaacgt cctgtcagaa gacaacatat tcatcttgct   60
aaggtttaag ctatatgact ggcactgtgc tcaactcaga gtcattgaat gaacagtatt  120
tattta                                                             126

<210> SEQ ID NO 113
```

```
<211> LENGTH: 22
<212> TYPE: DNA
<213> ORGANISM: Homo sapiens

<400> SEQUENCE: 113
cagggcatat aatctaagct gt                                              22

<210> SEQ ID NO 114
<211> LENGTH: 21
<212> TYPE: DNA
<213> ORGANISM: Homo sapiens

<400> SEQUENCE: 114
caatgactct gagttgagca c                                               21

<210> SEQ ID NO 115
<211> LENGTH: 132
<212> TYPE: DNA
<213> ORGANISM: Homo sapiens

<400> SEQUENCE: 115
ttcacattat tcccttaaaa taaactctct ccctcccctc tcccgtctca accttgtccc     60
tttctttata taatgggtaa ttcgttaatg tcagcagaat agttttgggg ccataatggc    120
aagtatcacg tg                                                        132

<210> SEQ ID NO 116
<211> LENGTH: 19
<212> TYPE: DNA
<213> ORGANISM: Homo sapiens

<400> SEQUENCE: 116
aactctctcc ctcccctct                                                  19

<210> SEQ ID NO 117
<211> LENGTH: 20
<212> TYPE: DNA
<213> ORGANISM: Homo sapiens

<400> SEQUENCE: 117
tatggcccca aaactattct                                                 20

<210> SEQ ID NO 118
<211> LENGTH: 110
<212> TYPE: DNA
<213> ORGANISM: Homo sapiens

<400> SEQUENCE: 118
tcaggaagca acaagtactg ggcagattga tactgtagct aggctctagc tctatacctc     60
tagaataaat gttacaaact agcaacttga aagctaaacc tggcccacag                110

<210> SEQ ID NO 119
<211> LENGTH: 20
<212> TYPE: DNA
<213> ORGANISM: Homo sapiens

<400> SEQUENCE: 119
acaagtactg ggcagattga                                                 20

<210> SEQ ID NO 120
<211> LENGTH: 20
<212> TYPE: DNA
<213> ORGANISM: Homo sapiens
```

```
<400> SEQUENCE: 120
gccaggttta gctttcaagt                                                      20

<210> SEQ ID NO 121
<211> LENGTH: 106
<212> TYPE: DNA
<213> ORGANISM: Homo sapiens

<400> SEQUENCE: 121
tggttcttga gaattttata tcaggagaaa cactgtcagt ctgtattgaa aggaacagag         60
aaaattcgaa attaaagaag actattaaac ctccaaaatt ctggca                       106

<210> SEQ ID NO 122
<211> LENGTH: 22
<212> TYPE: DNA
<213> ORGANISM: Homo sapiens

<400> SEQUENCE: 122
ttttatatca ggagaaacac tg                                                   22

<210> SEQ ID NO 123
<211> LENGTH: 21
<212> TYPE: DNA
<213> ORGANISM: Homo sapiens

<400> SEQUENCE: 123
ccagaatttt ggaggtttaa t                                                    21

<210> SEQ ID NO 124
<211> LENGTH: 171
<212> TYPE: DNA
<213> ORGANISM: Homo sapiens

<400> SEQUENCE: 124
gcatcaaact acacactgtc attcctcctt tatctccaaa agcttgaaaa ttcctcactt         60
gtatctcatt ctttctctct tagaaaactg atcacctctg atgaattaga acggaatgac        120
caagctttgg gagaggcaaa agaatctcgg tgttaaagac tcagagttta a                 171

<210> SEQ ID NO 125
<211> LENGTH: 22
<212> TYPE: DNA
<213> ORGANISM: Homo sapiens

<400> SEQUENCE: 125
tgtcattcct cctttatctc ca                                                   22

<210> SEQ ID NO 126
<211> LENGTH: 20
<212> TYPE: DNA
<213> ORGANISM: Homo sapiens

<400> SEQUENCE: 126
ttcttttgcc tctcccaaag                                                      20

<210> SEQ ID NO 127
<211> LENGTH: 163
<212> TYPE: DNA
<213> ORGANISM: Homo sapiens

<400> SEQUENCE: 127
ttgaaaatta agaaaccctg gcacagtgtt gactggagcc acttacctta atagaaaata        60
```

```
aagctcacat atatccataa tgaaaagcag agaccagcac aaccatagtc acctgacagt    120
tttaaaatcc aaggccagga tcttctcaac tcaggcccac tca                     163

<210> SEQ ID NO 128
<211> LENGTH: 20
<212> TYPE: DNA
<213> ORGANISM: Homo sapiens

<400> SEQUENCE: 128
accctggcac agtgttgact                                                20

<210> SEQ ID NO 129
<211> LENGTH: 20
<212> TYPE: DNA
<213> ORGANISM: Homo sapiens

<400> SEQUENCE: 129
tgggcctgag ttgagaagat                                                20

<210> SEQ ID NO 130
<211> LENGTH: 20
<212> TYPE: DNA
<213> ORGANISM: Homo sapiens

<400> SEQUENCE: 130
tttttcccat ttccaactct                                                20

<210> SEQ ID NO 131
<211> LENGTH: 122
<212> TYPE: DNA
<213> ORGANISM: Homo sapiens

<400> SEQUENCE: 131
aaaaaaaaag atgagacagg caggtgcgaa agaaataaaa gtcaaaactg atccagttgg    60
gaaactcaga attgacagtt acgtgtccctt tcatttattg atattttgag attcacaggg  120
gt                                                                  122

<210> SEQ ID NO 132
<211> LENGTH: 20
<212> TYPE: DNA
<213> ORGANISM: Homo sapiens

<400> SEQUENCE: 132
aaaagatgag acaggcaggt                                                20

<210> SEQ ID NO 133
<211> LENGTH: 20
<212> TYPE: DNA
<213> ORGANISM: Homo sapiens

<400> SEQUENCE: 133
acccctgtga atctcaaaat                                                20

<210> SEQ ID NO 134
<211> LENGTH: 150
<212> TYPE: DNA
<213> ORGANISM: Homo sapiens

<400> SEQUENCE: 134
gagttaaata aagcacttgc ttctattgtt tgtacctaaa cttaacagaa cacagtaagt    60
aacaagtcat tgggatgcag aaaagaaaaa agagagtgaa ggaaggagaa aaggtgaagg   120
```

```
gagaatggaa gagaggaagg gagggaggaa                                    150

<210> SEQ ID NO 135
<211> LENGTH: 21
<212> TYPE: DNA
<213> ORGANISM: Homo sapiens

<400> SEQUENCE: 135
gcacttgctt ctattgtttg t                                              21

<210> SEQ ID NO 136
<211> LENGTH: 20
<212> TYPE: DNA
<213> ORGANISM: Homo sapiens

<400> SEQUENCE: 136
cccttcctct cttccattct                                                20

<210> SEQ ID NO 137
<211> LENGTH: 129
<212> TYPE: DNA
<213> ORGANISM: Homo sapiens

<400> SEQUENCE: 137
aaacgagcca ccagtgggag cactgcaggt atctgtgtga gacccgtact tcacaactcc    60
tgctttccct ccataaagta gcttgcattt tccacattga ctttgcagtt ctttggtatc   120
tgtattggt                                                           129

<210> SEQ ID NO 138
<211> LENGTH: 18
<212> TYPE: DNA
<213> ORGANISM: Homo sapiens

<400> SEQUENCE: 138
gtgggagcac tgcaggta                                                  18

<210> SEQ ID NO 139
<211> LENGTH: 21
<212> TYPE: DNA
<213> ORGANISM: Homo sapiens

<400> SEQUENCE: 139
acagatacca aagaactgca a                                              21

<210> SEQ ID NO 140
<211> LENGTH: 145
<212> TYPE: DNA
<213> ORGANISM: Homo sapiens

<400> SEQUENCE: 140
tggacacctt tcaacttaga aatcataaac agattcattt ccttaaagtt aatgaaaaga    60
attaacagac cctcctcaaa aaagacatat atgcagccta caatcatatg aaaaaaagtt   120
caacattact gttcagcaaa tcaaa                                         145

<210> SEQ ID NO 141
<211> LENGTH: 20
<212> TYPE: DNA
<213> ORGANISM: Homo sapiens

<400> SEQUENCE: 141
tggacacctt tcaacttaga                                                20
```

```
<210> SEQ ID NO 142
<211> LENGTH: 22
<212> TYPE: DNA
<213> ORGANISM: Homo sapiens

<400> SEQUENCE: 142
gaacagtaat gttgaactttt tt                                             22

<210> SEQ ID NO 143
<211> LENGTH: 155
<212> TYPE: DNA
<213> ORGANISM: Homo sapiens

<400> SEQUENCE: 143
tggatacatt cctagaaata gatggaaact gctcttgcaa aaagcttagc acatgttaaa     60
aattttagaa acaatttgcc aaagtttatt tagtctagtg attttgacag gttaaatgga   120
ccctttgaga tcttttttcc tcaagtacaa aggct                              155

<210> SEQ ID NO 144
<211> LENGTH: 21
<212> TYPE: DNA
<213> ORGANISM: Homo sapiens

<400> SEQUENCE: 144
tcttgcaaaa agcttagcac a                                               21

<210> SEQ ID NO 145
<211> LENGTH: 21
<212> TYPE: DNA
<213> ORGANISM: Homo sapiens

<400> SEQUENCE: 145
aaaaagatct caaagggtcc a                                               21

<210> SEQ ID NO 146
<211> LENGTH: 119
<212> TYPE: DNA
<213> ORGANISM: Homo sapiens

<400> SEQUENCE: 146
gcttttgctg aacatcaagt ggtgagccag gactcaaagc cagatcttct tgtttccctg     60
ttaggtgttt gtagcacaac tggtatctgc agactatgct gctggaaggg ctagccgtc    119

<210> SEQ ID NO 147
<211> LENGTH: 20
<212> TYPE: DNA
<213> ORGANISM: Homo sapiens

<400> SEQUENCE: 147
gcttttgctg aacatcaagt                                                 20

<210> SEQ ID NO 148
<211> LENGTH: 19
<212> TYPE: DNA
<213> ORGANISM: Homo sapiens

<400> SEQUENCE: 148
ccttccagca gcatagtct                                                  19

<210> SEQ ID NO 149
<211> LENGTH: 161
<212> TYPE: DNA
```

<213> ORGANISM: Homo sapiens

<400> SEQUENCE: 149

| | | | | | |
|---|---|---|---|---|---|
| actgtcctag | aaaatccagg | atgtgcagtg | atcatgtatg | aatgcatgga | cctgcacaca | 60 |
| caggagtgaa | caaaagaccc | acccctgcca | ggtcaccact | catatctcac | cccagcccac | 120 |
| gctagctcac | actcctcccc | acacaccact | gacctcatca | t | | 161 |

<210> SEQ ID NO 150
<211> LENGTH: 18
<212> TYPE: DNA
<213> ORGANISM: Homo sapiens

<400> SEQUENCE: 150
aaatccagga tgtgcagt                                          18

<210> SEQ ID NO 151
<211> LENGTH: 19
<212> TYPE: DNA
<213> ORGANISM: Homo sapiens

<400> SEQUENCE: 151
atgatgaggt cagtggtgt                                         19

<210> SEQ ID NO 152
<211> LENGTH: 124
<212> TYPE: DNA
<213> ORGANISM: Homo sapiens

<400> SEQUENCE: 152

| | | | | | |
|---|---|---|---|---|---|
| cacatcacag | atcatagtaa | atggctttaa | ttttttaacg | aaatctcact | actgcaaatg | 60 |
| cattgttgtc | ctagctaatg | aatgcataga | gtattgcctg | caaataata | attgagattc | 120 |
| tatt | | | | | | 124 |

<210> SEQ ID NO 153
<211> LENGTH: 22
<212> TYPE: DNA
<213> ORGANISM: Homo sapiens

<400> SEQUENCE: 153
catcacagat catagtaaat gg                                     22

<210> SEQ ID NO 154
<211> LENGTH: 21
<212> TYPE: DNA
<213> ORGANISM: Homo sapiens

<400> SEQUENCE: 154
aattattatt ttgcaggcaa t                                      21

<210> SEQ ID NO 155
<211> LENGTH: 151
<212> TYPE: DNA
<213> ORGANISM: Homo sapiens

<400> SEQUENCE: 155

| | | | | | |
|---|---|---|---|---|---|
| ttatcctcca | catcctcatg | aggcaaacac | ctttcctacc | ttaccgctcc | ccagtggcct | 60 |
| ccctgttgcc | ttcttattca | agactaagac | tctctagaat | gttctttatc | ctgagtccag | 120 |
| ctgattgtct | atactaatat | cagtacgggg | t | | | 151 |

<210> SEQ ID NO 156

```
<211> LENGTH: 20
<212> TYPE: DNA
<213> ORGANISM: Homo sapiens

<400> SEQUENCE: 156
catgaggcaa acacctttcc                                                   20

<210> SEQ ID NO 157
<211> LENGTH: 22
<212> TYPE: DNA
<213> ORGANISM: Homo sapiens

<400> SEQUENCE: 157
gctggactca ggataaagaa ca                                                22

<210> SEQ ID NO 158
<211> LENGTH: 145
<212> TYPE: DNA
<213> ORGANISM: Homo sapiens

<400> SEQUENCE: 158
agggtgcagc actttattat ggaagcctga gctgactaat acaggtgtct ctatatctca       60
ctgagggaaa gtgacaggaa agtaagaacc atttatgtcc aagagtccag aggagtcaac      120
cagattctgg gggaaaagaa ggtac                                            145

<210> SEQ ID NO 159
<211> LENGTH: 20
<212> TYPE: DNA
<213> ORGANISM: Homo sapiens

<400> SEQUENCE: 159
tggaagcctg agctgactaa                                                   20

<210> SEQ ID NO 160
<211> LENGTH: 20
<212> TYPE: DNA
<213> ORGANISM: Homo sapiens

<400> SEQUENCE: 160
ccttcttttc ccccagaatc                                                   20

<210> SEQ ID NO 161
<211> LENGTH: 154
<212> TYPE: DNA
<213> ORGANISM: Homo sapiens

<400> SEQUENCE: 161
tgagaattta ggagaacaga agatcagagg gctgcacagg ctaaactaga caatgagccc       60
atgcaagtaa gttaagagga gaagcgggta agtatgcacc tgctttgtct aggtgaccag      120
caagcattta gcaatagtct tttcaaaaca acag                                  154

<210> SEQ ID NO 162
<211> LENGTH: 22
<212> TYPE: DNA
<213> ORGANISM: Homo sapiens

<400> SEQUENCE: 162
ttaggagaac agaagatcag ag                                                22

<210> SEQ ID NO 163
<211> LENGTH: 22
<212> TYPE: DNA
```

<213> ORGANISM: Homo sapiens

<400> SEQUENCE: 163
aaagactatt gctaaatgct tg                                          22

<210> SEQ ID NO 164
<211> LENGTH: 106
<212> TYPE: DNA
<213> ORGANISM: Homo sapiens

<400> SEQUENCE: 164
aaacaggcaa aataagcgta gggctgtgtg tgcaacagtt aatcataaag ccatcaccag   60
gagacgtcac tgggcgcctt ctggagtcta tccgtcctaa ctttgc                 106

<210> SEQ ID NO 165
<211> LENGTH: 20
<212> TYPE: DNA
<213> ORGANISM: Homo sapiens

<400> SEQUENCE: 165
taagcgtagg gctgtgtgtg                                             20

<210> SEQ ID NO 166
<211> LENGTH: 21
<212> TYPE: DNA
<213> ORGANISM: Homo sapiens

<400> SEQUENCE: 166
ggacggatag actccagaag g                                           21

<210> SEQ ID NO 167
<211> LENGTH: 105
<212> TYPE: DNA
<213> ORGANISM: Homo sapiens

<400> SEQUENCE: 167
gaatgacctt ggcactttta tcaaacatca actggccaca cacaggtgag tctacttctg   60
gacacttatc ctgttccatt catctgtata tctctatcct tacac                  105

<210> SEQ ID NO 168
<211> LENGTH: 23
<212> TYPE: DNA
<213> ORGANISM: Homo sapiens

<400> SEQUENCE: 168
gaatgacctt ggcactttta tca                                         23

<210> SEQ ID NO 169
<211> LENGTH: 27
<212> TYPE: DNA
<213> ORGANISM: Homo sapiens

<400> SEQUENCE: 169
aaggatagag atatacagat gaatgga                                     27

<210> SEQ ID NO 170
<211> LENGTH: 129
<212> TYPE: DNA
<213> ORGANISM: Homo sapiens

<400> SEQUENCE: 170
ctgctggaat aggctgcttg gccatgttct tggaagctac caccatatca aggtaatttc   60

```
ccacacaaca ttccagcccc tgctttcctc tctggcctta tctagggcca ttccccaact        120
caggtgaat                                                                129

<210> SEQ ID NO 171
<211> LENGTH: 20
<212> TYPE: DNA
<213> ORGANISM: Homo sapiens

<400> SEQUENCE: 171
ggccatgttc ttggaagcta                                                     20

<210> SEQ ID NO 172
<211> LENGTH: 20
<212> TYPE: DNA
<213> ORGANISM: Homo sapiens

<400> SEQUENCE: 172
ttcacctgag ttggggaatg                                                     20

<210> SEQ ID NO 173
<211> LENGTH: 138
<212> TYPE: DNA
<213> ORGANISM: Homo sapiens

<400> SEQUENCE: 173
acctttgttc catgcaccgc gcaaatacct gggaaccctt attgcccaac tcaagagcca         60
gagtcctctg tcatcatttt gcctctctcc taagtgagag gactgagtgc agacttggtg        120
tttgtgggtg aggcatgt                                                      138

<210> SEQ ID NO 174
<211> LENGTH: 18
<212> TYPE: DNA
<213> ORGANISM: Homo sapiens

<400> SEQUENCE: 174
catgcaccgc gcaaatac                                                       18

<210> SEQ ID NO 175
<211> LENGTH: 19
<212> TYPE: DNA
<213> ORGANISM: Homo sapiens

<400> SEQUENCE: 175
atgcctcacc cacaaacac                                                      19

<210> SEQ ID NO 176
<211> LENGTH: 159
<212> TYPE: DNA
<213> ORGANISM: Homo sapiens

<400> SEQUENCE: 176
ctcctgagtc caagcccttc tcactcacct ctttcttgaa ctaatttctt cctgtttttt         60
tccagtcctc ccttctgttc atgtctctcc tctgcacact tccattttgt ggttcagaaa        120
atgtcaccgt cccagtcaca cttgccttat ggctgttgt                               159

<210> SEQ ID NO 177
<211> LENGTH: 20
<212> TYPE: DNA
<213> ORGANISM: Homo sapiens

<400> SEQUENCE: 177
```

```
tccaagccct tctcactcac                                              20

<210> SEQ ID NO 178
<211> LENGTH: 20
<212> TYPE: DNA
<213> ORGANISM: Homo sapiens

<400> SEQUENCE: 178
ctgggacggt gacattttct                                              20

<210> SEQ ID NO 179
<211> LENGTH: 132
<212> TYPE: DNA
<213> ORGANISM: Homo sapiens

<400> SEQUENCE: 179
cccaggaaga gtggaaagat taacctttgt gagccaaacc agtgacactt gattacttga   60
cagaactaat ccttctgtcc tgatgacaga acttcaacta cacaggtaca tgcaagctaa  120
tatctgttgt aa                                                     132

<210> SEQ ID NO 180
<211> LENGTH: 21
<212> TYPE: DNA
<213> ORGANISM: Homo sapiens

<400> SEQUENCE: 180
cccaggaaga gtggaaagat t                                            21

<210> SEQ ID NO 181
<211> LENGTH: 21
<212> TYPE: DNA
<213> ORGANISM: Homo sapiens

<400> SEQUENCE: 181
ttagcttgca tgtacctgtg t                                            21

<210> SEQ ID NO 182
<211> LENGTH: 165
<212> TYPE: DNA
<213> ORGANISM: Homo sapiens

<400> SEQUENCE: 182
gcctggcaag ctagatgggg tgaattttca cctgccacag ccgcaagtca aagccaccgg   60
cttctctctt ctccctccca ttgctcctga cagccagggt taatattttg cctcatgtaa  120
acagggaggc atccacccga gaatctcccc tcagcccaca taagc                 165

<210> SEQ ID NO 183
<211> LENGTH: 20
<212> TYPE: DNA
<213> ORGANISM: Homo sapiens

<400> SEQUENCE: 183
agctagatgg ggtgaatttt                                              20

<210> SEQ ID NO 184
<211> LENGTH: 18
<212> TYPE: DNA
<213> ORGANISM: Homo sapiens

<400> SEQUENCE: 184
tgggctgagg ggagattc                                                18
```

```
<210> SEQ ID NO 185
<211> LENGTH: 160
<212> TYPE: DNA
<213> ORGANISM: Homo sapiens

<400> SEQUENCE: 185
atcaagctaa ttaatgttat ctatcacttc acatagttca accttttttt gtggtgagag    60
tactgaagat ctactctctt agcaattttc aaatctaaaa tacattatta ttaacacagt   120
cactgtgccg tacgttagct ctgaggacct tattcatttt                         160

<210> SEQ ID NO 186
<211> LENGTH: 22
<212> TYPE: DNA
<213> ORGANISM: Homo sapiens

<400> SEQUENCE: 186
atcaagctaa ttaatgttat ct                                             22

<210> SEQ ID NO 187
<211> LENGTH: 20
<212> TYPE: DNA
<213> ORGANISM: Homo sapiens

<400> SEQUENCE: 187
aatgaataag gtcctcagag                                                20

<210> SEQ ID NO 188
<211> LENGTH: 124
<212> TYPE: DNA
<213> ORGANISM: Homo sapiens

<400> SEQUENCE: 188
tttaatctga tcattgccct atgaggtagg gagtattctg attcccattt tataaataag    60
gaacccgagg cttagagagc atcagtgact tgttcaaggt cacccacagc tgtcaagtga   120
caga                                                                124

<210> SEQ ID NO 189
<211> LENGTH: 21
<212> TYPE: DNA
<213> ORGANISM: Homo sapiens

<400> SEQUENCE: 189
tttaatctga tcattgccct a                                              21

<210> SEQ ID NO 190
<211> LENGTH: 18
<212> TYPE: DNA
<213> ORGANISM: Homo sapiens

<400> SEQUENCE: 190
agctgtgggt gaccttga                                                  18

<210> SEQ ID NO 191
<211> LENGTH: 128
<212> TYPE: DNA
<213> ORGANISM: Homo sapiens

<400> SEQUENCE: 191
tgtcccacca ttgtgtatta ggtttgtaga gcgtagacaa cttgcctttt tagtttgtag    60
gtttctgtat caagagaaga tgtgtgtggg cctaacctag attacaggat cctggacttc   120
```

```
aagtctga                                                                    128

<210> SEQ ID NO 192
<211> LENGTH: 20
<212> TYPE: DNA
<213> ORGANISM: Homo sapiens

<400> SEQUENCE: 192
tgtcccacca ttgtgtatta                                                        20

<210> SEQ ID NO 193
<211> LENGTH: 20
<212> TYPE: DNA
<213> ORGANISM: Homo sapiens

<400> SEQUENCE: 193
tcagacttga agtccaggat                                                        20

<210> SEQ ID NO 194
<211> LENGTH: 128
<212> TYPE: DNA
<213> ORGANISM: Homo sapiens

<400> SEQUENCE: 194
tcatttgcta aggtcggata gctcctaatt ggcaaagtca cgatgggatc ccagggattc            60
tgaggatgaa gcctgtgttt aataactatt atgccaagtg agcattttca aatatatgag           120
agaaatta                                                                    128

<210> SEQ ID NO 195
<211> LENGTH: 19
<212> TYPE: DNA
<213> ORGANISM: Homo sapiens

<400> SEQUENCE: 195
catttgctaa ggtcggata                                                         19

<210> SEQ ID NO 196
<211> LENGTH: 20
<212> TYPE: DNA
<213> ORGANISM: Homo sapiens

<400> SEQUENCE: 196
tatttgaaaa tgctcacttg                                                        20

<210> SEQ ID NO 197
<211> LENGTH: 159
<212> TYPE: DNA
<213> ORGANISM: Homo sapiens

<400> SEQUENCE: 197
cattgcttca ggggtgttag ttttgtgttc acaactagat tataaactcc tcttgcattc            60
ctgatggcag tgacttgaag gcatttattt gaagaataat agacatacag aaagggcac           120 atgtcataaa ggtacagctg gacgactttt cacaaagtg                                  159

<210> SEQ ID NO 198
<211> LENGTH: 20
<212> TYPE: DNA
<213> ORGANISM: Homo sapiens

<400> SEQUENCE: 198
gcttcagggg tgttagtttt                                                        20
```

```
<210> SEQ ID NO 199
<211> LENGTH: 20
<212> TYPE: DNA
<213> ORGANISM: Homo sapiens

<400> SEQUENCE: 199
ctttgtgaaa agtcgtccag                                                    20

<210> SEQ ID NO 200
<211> LENGTH: 117
<212> TYPE: DNA
<213> ORGANISM: Homo sapiens

<400> SEQUENCE: 200
gagaggatgg tgccatcatg gaaagcatgg ggcagtcatg gagatgacgg agtagctcat        60
ggagaagata atgccatcat ggaaggcata gtgcagtcat ggagatgatg gtgcagc          117

<210> SEQ ID NO 201
<211> LENGTH: 18
<212> TYPE: DNA
<213> ORGANISM: Homo sapiens

<400> SEQUENCE: 201
ccatcatgga aagcatgg                                                      18

<210> SEQ ID NO 202
<211> LENGTH: 20
<212> TYPE: DNA
<213> ORGANISM: Homo sapiens

<400> SEQUENCE: 202
tcatctccat gactgcacta                                                    20

<210> SEQ ID NO 203
<211> LENGTH: 167
<212> TYPE: DNA
<213> ORGANISM: Homo sapiens

<400> SEQUENCE: 203
atggggcagt catggagatg acggagtagc tcatggagaa aataatgcca tcatggaagg        60
catagtgcag tcatggagat gatggtgcag ctcatggaga agatggtgcc atcatggaag       120
gcatggtgca atcatggagt agacagtgca gctgggccaa gattctc                    167

<210> SEQ ID NO 204
<211> LENGTH: 20
<212> TYPE: DNA
<213> ORGANISM: Homo sapiens

<400> SEQUENCE: 204
gagatgacgg agtagctcat                                                    20

<210> SEQ ID NO 205
<211> LENGTH: 18
<212> TYPE: DNA
<213> ORGANISM: Homo sapiens

<400> SEQUENCE: 205
cccagctgca ctgtctac                                                      18

<210> SEQ ID NO 206
<211> LENGTH: 128
<212> TYPE: DNA
```

<213> ORGANISM: Homo sapiens

<400> SEQUENCE: 206

```
gatgtgcctc tcttgttcca atcacaggac aggggtataa ctaggggcac tgtctatact        60
ggctgcactc tggccagtgc tgtcccaggt agattcatca gggtctagag cttcagctaa       120
cagcatga                                                                128
```

<210> SEQ ID NO 207
<211> LENGTH: 20
<212> TYPE: DNA
<213> ORGANISM: Homo sapiens

<400> SEQUENCE: 207

```
tcttgttcca atcacaggac                                                    20
```

<210> SEQ ID NO 208
<211> LENGTH: 20
<212> TYPE: DNA
<213> ORGANISM: Homo sapiens

<400> SEQUENCE: 208

```
atgctgttag ctgaagctct                                                    20
```

<210> SEQ ID NO 209
<211> LENGTH: 109
<212> TYPE: DNA
<213> ORGANISM: Homo sapiens

<400> SEQUENCE: 209

```
ttttattcat taagttgaaa gctcctaaag cagagggacc atatttttat gtcccaactc        60
tccttaaggc cttgcctatg atagcacatc tcttcaatag aattgtcct                   109
```

<210> SEQ ID NO 210
<211> LENGTH: 20
<212> TYPE: DNA
<213> ORGANISM: Homo sapiens

<400> SEQUENCE: 210

```
tgaaagctcc taaagcagag                                                    20
```

<210> SEQ ID NO 211
<211> LENGTH: 20
<212> TYPE: DNA
<213> ORGANISM: Homo sapiens

<400> SEQUENCE: 211

```
ttgaagagat gtgctatcat                                                    20
```

<210> SEQ ID NO 212
<211> LENGTH: 163
<212> TYPE: DNA
<213> ORGANISM: Homo sapiens

<400> SEQUENCE: 212

```
cacataacta ataaatttgt aagtatgtgc aacggctcac acttgcttcc agaatggcac        60
ctaaaaaaca gatttacctc tccccaaatt cagatatgga attaaatgta atgtcaggaa       120
aactgtctaa gagttggaaa tgggaaaaaa atgttctttt ggt                         163
```

<210> SEQ ID NO 213
<211> LENGTH: 21
<212> TYPE: DNA

```
<213> ORGANISM: Homo sapiens

<400> SEQUENCE: 213
aatttgtaag tatgtgcaac g                                              21

<210> SEQ ID NO 214
<211> LENGTH: 207
<212> TYPE: DNA
<213> ORGANISM: Homo sapiens

<400> SEQUENCE: 214
aaagaccagc ttttagctga acatcagggc tgccttcaga gtttaattac cgccctcccc    60
atggggccaa atgagccatc gactcctccc aagggggttc ggcttggtac tgatctttaa   120
gtaagtaaac gctaaaccag ctcatcttaa agcgcccaca tctgatttcc tgctctgctg   180
caagacagta ggtgactggt aatgacc                                       207

<210> SEQ ID NO 215
<211> LENGTH: 20
<212> TYPE: DNA
<213> ORGANISM: Homo sapiens

<400> SEQUENCE: 215
agggctgcct tcagagttta                                                20

<210> SEQ ID NO 216
<211> LENGTH: 20
<212> TYPE: DNA
<213> ORGANISM: Homo sapiens

<400> SEQUENCE: 216
gcgctttaag atgagctggt                                                20

<210> SEQ ID NO 217
<211> LENGTH: 192
<212> TYPE: DNA
<213> ORGANISM: Homo sapiens

<400> SEQUENCE: 217
actctgctcc cagtgtgaac atggggaaag ttgattaaac tctctgactt cagattcctc    60
atgtaaaatg tggggaaaca gctctgactt aatggtgtca ctgtgaggag taaatgaggt   120
agcatattta aaggattttg tatagtgctg gtgacagtaa ccagccaata gatgatatag   180
ctagtaatag ca                                                       192

<210> SEQ ID NO 218
<211> LENGTH: 20
<212> TYPE: DNA
<213> ORGANISM: Homo sapiens

<400> SEQUENCE: 218
tgaacatggg gaaagttgat                                                20

<210> SEQ ID NO 219
<211> LENGTH: 22
<212> TYPE: DNA
<213> ORGANISM: Homo sapiens

<400> SEQUENCE: 219
tcaccagcac tatacaaaat cc                                             22

<210> SEQ ID NO 220
```

```
<211> LENGTH: 170
<212> TYPE: DNA
<213> ORGANISM: Homo sapiens

<400> SEQUENCE: 220
cttcactgac cacttcctta actgtccact ccgaaacacc ccttcttcct gttcttccaa      60
tacaccaaac tctttcttgc ctctgtgtgc ttgcccatgc tgttccttct ggcttcttcc     120
ttcacattca agtcttgact tagatgtcac ttgccaaggg agaccttgga                170

<210> SEQ ID NO 221
<211> LENGTH: 21
<212> TYPE: DNA
<213> ORGANISM: Homo sapiens

<400> SEQUENCE: 221
acttccttaa ctgtccactc c                                                21

<210> SEQ ID NO 222
<211> LENGTH: 19
<212> TYPE: DNA
<213> ORGANISM: Homo sapiens

<400> SEQUENCE: 222
ccttggcaag tgacatcta                                                   19

<210> SEQ ID NO 223
<211> LENGTH: 181
<212> TYPE: DNA
<213> ORGANISM: Homo sapiens

<400> SEQUENCE: 223
aaacatccca atagacaaaa ctccaagaag agtcaaaaca agaataaagt acaggtcatc      60
ttttcttttg cactcctgac agcactttgt acatggtaat aataatctac caattaacta    120
cataagccac atggttttat catagtgtga agctttgtat ccagaaagga gagaaggctc    180
c                                                                    181

<210> SEQ ID NO 224
<211> LENGTH: 22
<212> TYPE: DNA
<213> ORGANISM: Homo sapiens

<400> SEQUENCE: 224
ccaagaagag tcaaaacaag aa                                              22

<210> SEQ ID NO 225
<211> LENGTH: 21
<212> TYPE: DNA
<213> ORGANISM: Homo sapiens

<400> SEQUENCE: 225
tctcctttct ggatacaaag c                                               21

<210> SEQ ID NO 226
<211> LENGTH: 149
<212> TYPE: DNA
<213> ORGANISM: Homo sapiens

<400> SEQUENCE: 226
ggcagaggca tggggtgcat agggatatgg ggtgggccag tttgctcctc agaccagaag      60
gggtgcagga ctcccccccga tcaggatcat ggagaaaggt gtggacagag gaagggaggg    120
```

```
agggagaaat ggcagctgcc ctgcagtgg                                      149

<210> SEQ ID NO 227
<211> LENGTH: 20
<212> TYPE: DNA
<213> ORGANISM: Homo sapiens

<400> SEQUENCE: 227
ttgctcctca gaccagaagg                                                 20

<210> SEQ ID NO 228
<211> LENGTH: 20
<212> TYPE: DNA
<213> ORGANISM: Homo sapiens

<400> SEQUENCE: 228
ctcccttcct ctgtccacac                                                 20

<210> SEQ ID NO 229
<211> LENGTH: 165
<212> TYPE: DNA
<213> ORGANISM: Homo sapiens

<400> SEQUENCE: 229
cagggactaa gtgtctctga caatacattc agccactact acagtatgaa gccagcccct     60
catccccacc ttcagagacc cctggtgcct cagattcctc ggccattctg gagctgctgt    120
gcccgaggct tgtgtagttg agatcatttt ggcagtcag tgctg                     165

<210> SEQ ID NO 230
<211> LENGTH: 22
<212> TYPE: DNA
<213> ORGANISM: Homo sapiens

<400> SEQUENCE: 230
tgtctctgac aatacattca gc                                              22

<210> SEQ ID NO 231
<211> LENGTH: 20
<212> TYPE: DNA
<213> ORGANISM: Homo sapiens

<400> SEQUENCE: 231
ctgactgcca aaatgatctc                                                 20

<210> SEQ ID NO 232
<211> LENGTH: 181
<212> TYPE: DNA
<213> ORGANISM: Homo sapiens

<400> SEQUENCE: 232
cctgtctccg tgcgtgaaag ccggctccaa agtgccttct gtcctatctg ccttccgcac     60
ctggctttcc tgaaagaaag aaaacgcgtg gcttatcttt tcacggcacg ccaccttcac    120
tctcactttt tcttttctaa taaatacctc tggatgggtt agtggtaatc tctcctcaaa    180
c                                                                    181

<210> SEQ ID NO 233
<211> LENGTH: 20
<212> TYPE: DNA
<213> ORGANISM: Homo sapiens

<400> SEQUENCE: 233
```

```
gctccaaagt gccttctgtc                                              20

<210> SEQ ID NO 234
<211> LENGTH: 20
<212> TYPE: DNA
<213> ORGANISM: Homo sapiens

<400> SEQUENCE: 234
ccactaaccc atccagaggt                                              20

<210> SEQ ID NO 235
<211> LENGTH: 198
<212> TYPE: DNA
<213> ORGANISM: Homo sapiens

<400> SEQUENCE: 235
gggagcacaa cctaggcccc tcctggggag gtggtggagt cagaatcacg taagagacaa  60
agttccagtc cctcagtgcc ggctccattg tccctggac ttcccttaca aaccacagat  120
gcaaagagag cacttctcgg aatctccaca cagccacggt ggagcactca acccacgcga 180
ccctcgggcg caggtgct                                                198

<210> SEQ ID NO 236
<211> LENGTH: 20
<212> TYPE: DNA
<213> ORGANISM: Homo sapiens

<400> SEQUENCE: 236
ctggggaggt ggtggagtca                                              20

<210> SEQ ID NO 237
<211> LENGTH: 20
<212> TYPE: DNA
<213> ORGANISM: Homo sapiens

<400> SEQUENCE: 237
gagtgctcca ccgtggctgt                                              20

<210> SEQ ID NO 238
<211> LENGTH: 161
<212> TYPE: DNA
<213> ORGANISM: Homo sapiens

<400> SEQUENCE: 238
cctgagaagc ttccagcaaa gcaccagcac gaaccgcccc acctccccac ctccccgcaa  60
gcgttgccgg gactgacaga ttacagagct ctggtccctc tgcactcctg ctctgccacc  120
cccagggtgt cagaatgtgc cccccacaca gtttccaaaa g                      161

<210> SEQ ID NO 239
<211> LENGTH: 18
<212> TYPE: DNA
<213> ORGANISM: Homo sapiens

<400> SEQUENCE: 239
aaagcaccag cacgaacc                                                18

<210> SEQ ID NO 240
<211> LENGTH: 18
<212> TYPE: DNA
<213> ORGANISM: Homo sapiens

<400> SEQUENCE: 240
```

```
ggggcacatt ctgacacc                                            18

<210> SEQ ID NO 241
<211> LENGTH: 162
<212> TYPE: DNA
<213> ORGANISM: Homo sapiens

<400> SEQUENCE: 241
atggagctgc tgcgccggcc tgagctctga tccctcctcc gacccagcct caccctgcaa   60
gcagcaccat gtggggctca gaatggggat cttaagggac cctccccaca acctcccgat  120 aagccttctcc acggagggcc caagcggaga caggagaaca ct                    162

<210> SEQ ID NO 242
<211> LENGTH: 19
<212> TYPE: DNA
<213> ORGANISM: Homo sapiens

<400> SEQUENCE: 242
ctgagctctg atccctcct                                            19

<210> SEQ ID NO 243
<211> LENGTH: 18
<212> TYPE: DNA
<213> ORGANISM: Homo sapiens

<400> SEQUENCE: 243
ttctcctgtc tccgcttg                                            18

<210> SEQ ID NO 244
<211> LENGTH: 194
<212> TYPE: DNA
<213> ORGANISM: Homo sapiens

<400> SEQUENCE: 244
actttcagaa tgtgctgcct tccacgtgtg aaccagactg agctcctttc tgccactgat   60
gttgaattgt ccatttgctc acatcagtgt ccacgtggca aatccacagg gcgtgggtgg  120
gatcctgcag tctagacaaa gccaaggagc accgctggag gccacgttgg gcttcccaat  180
ccacatgcaa accc                                                   194

<210> SEQ ID NO 245
<211> LENGTH: 20
<212> TYPE: DNA
<213> ORGANISM: Homo sapiens

<400> SEQUENCE: 245
cctttctgcc actgatgttg                                           20

<210> SEQ ID NO 246
<211> LENGTH: 19
<212> TYPE: DNA
<213> ORGANISM: Homo sapiens

<400> SEQUENCE: 246
ttgcatgtgg attgggaag                                            19

<210> SEQ ID NO 247
<211> LENGTH: 213
<212> TYPE: DNA
<213> ORGANISM: Homo sapiens

<400> SEQUENCE: 247
```

```
tctccagcca gcgtgtcaca aagccgctca cctgctcgtg tgagtgtctg aatgcacgtg      60
tttgagtgtc agaggcgtgt gaaccacagc aactcaatct tgaataggggg ctgggtaaag    120 tgaggctgag acctcccggg gctgcattcc cagatggtta aggcattcta agtcacaaga    180
tgagatagga agttcgcaca agacactggt cat                                  213
```

<210> SEQ ID NO 248
<211> LENGTH: 20
<212> TYPE: DNA
<213> ORGANISM: Homo sapiens

<400> SEQUENCE: 248

```
tcacctgctc gtgtgagtgt                                                  20
```

<210> SEQ ID NO 249
<211> LENGTH: 20
<212> TYPE: DNA
<213> ORGANISM: Homo sapiens

<400> SEQUENCE: 249

```
ccttaaccat ctgggaatgc                                                  20
```

<210> SEQ ID NO 250
<211> LENGTH: 152
<212> TYPE: DNA
<213> ORGANISM: Homo sapiens

<400> SEQUENCE: 250

```
ttgagtcctc ttaagtagtt actatagtgg agaacttgag tcattctttg tagcgtgctt      60
cgtagagcag cgtgtttgtt agaaggattt gttaatcctg tatagggtct ttacgaaggc    120
tgttttcatg gaagcttctc tttgttgact cc                                   152
```

<210> SEQ ID NO 251
<211> LENGTH: 22
<212> TYPE: DNA
<213> ORGANISM: Homo sapiens

<400> SEQUENCE: 251

```
tggagaactt gagtcattct tt                                               22
```

<210> SEQ ID NO 252
<211> LENGTH: 19
<212> TYPE: DNA
<213> ORGANISM: Homo sapiens

<400> SEQUENCE: 252

```
ggagtcaaca aagagaagc                                                   19
```

<210> SEQ ID NO 253
<211> LENGTH: 174
<212> TYPE: DNA
<213> ORGANISM: Homo sapiens

<400> SEQUENCE: 253

```
cattctctcc agctgcaaac tttcttcaac tttcctaaat tcttactaaa ttcagaggaa      60
taggataaag atcacttaga gaaagggtgc ttatggacat agcctgagtt tcctttaacc    120
tctctgcaat gggtgctttt aactagcttc tacatggcaa gctgtttcag tttg           174
```

<210> SEQ ID NO 254
<211> LENGTH: 21
<212> TYPE: DNA

-continued

<213> ORGANISM: Homo sapiens

<400> SEQUENCE: 254
ctttcttcaa ctttcctaaa t                                             21

<210> SEQ ID NO 255
<211> LENGTH: 19
<212> TYPE: DNA
<213> ORGANISM: Homo sapiens

<400> SEQUENCE: 255
ttgccatgta gaagctagt                                                19

<210> SEQ ID NO 256
<211> LENGTH: 175
<212> TYPE: DNA
<213> ORGANISM: Homo sapiens

<400> SEQUENCE: 256
ggacatctgg aactgcacca gcacagaacc gacacgttgt tactcatcgt cactcggcag   60
ggctgaagac caccagaact catgacaggc agacgtgcct ggcccagttg aggatgtagc  120
ttcagagcca agcgccagtc ctgttggcca cgtgggctgg ggcaggata gacca         175

<210> SEQ ID NO 257
<211> LENGTH: 19
<212> TYPE: DNA
<213> ORGANISM: Homo sapiens

<400> SEQUENCE: 257
accagcacag aaccgacac                                                19

<210> SEQ ID NO 258
<211> LENGTH: 18
<212> TYPE: DNA
<213> ORGANISM: Homo sapiens

<400> SEQUENCE: 258
aacaggactg gcgcttgg                                                 18

<210> SEQ ID NO 259
<211> LENGTH: 182
<212> TYPE: DNA
<213> ORGANISM: Homo sapiens

<400> SEQUENCE: 259
ggctggttct gcccttggga ggtggttcct ttggctggac cagaatgtct gaagatgatc   60
aggagagggc caaggttggg gggtgcccc atgtgcaccc tgagaattgc accaggcaca  120
gtgagcaact tcagccctcc ttgtgcagag ctgcagcgta cagtgccagc cctcgctggc  180
cc                                                                  182

<210> SEQ ID NO 260
<211> LENGTH: 20
<212> TYPE: DNA
<213> ORGANISM: Homo sapiens

<400> SEQUENCE: 260
cttgggaggt ggttcctttg                                               20

<210> SEQ ID NO 261
<211> LENGTH: 18
<212> TYPE: DNA

<213> ORGANISM: Homo sapiens

<400> SEQUENCE: 261
ctgcacaagg agggctga                                                      18

<210> SEQ ID NO 262
<211> LENGTH: 155
<212> TYPE: DNA
<213> ORGANISM: Homo sapiens

<400> SEQUENCE: 262
gttctcactt tactgagaaa cctggcagct tctcaggcca ccgcccaggt cacctgctca        60
ccagcaacgt gaaccacagg aactgaggct gtgcgggagg cggctctgct ctgtgctggg       120 ccccctcct cctcactcac cctcttcagt caaag                                   155

<210> SEQ ID NO 263
<211> LENGTH: 20
<212> TYPE: DNA
<213> ORGANISM: Homo sapiens

<400> SEQUENCE: 263
tactgagaaa cctggcagct                                                    20

<210> SEQ ID NO 264
<211> LENGTH: 20
<212> TYPE: DNA
<213> ORGANISM: Homo sapiens

<400> SEQUENCE: 264
ctttgactga agagggtgag                                                    20

<210> SEQ ID NO 265
<211> LENGTH: 180
<212> TYPE: DNA
<213> ORGANISM: Homo sapiens

<400> SEQUENCE: 265
ttagtattat tattttcata tatattttt ataataatca tatattcaat tttatcatca        60
agaaaaaagt tttaaaattc aaaatccttt catgtgcact gttttaaact taggtagaag       120
aaaaaaagtc actgaaaatc caagatgtaa taaacaggcc caacaaggc caacaaactt       180

<210> SEQ ID NO 266
<211> LENGTH: 20
<212> TYPE: DNA
<213> ORGANISM: Homo sapiens

<400> SEQUENCE: 266 ttcaattta tcatcaagaa                                                    20

<210> SEQ ID NO 267
<211> LENGTH: 20
<212> TYPE: DNA
<213> ORGANISM: Homo sapiens

<400> SEQUENCE: 267
ttgggcctgt ttattacatc                                                    20

<210> SEQ ID NO 268
<211> LENGTH: 196
<212> TYPE: DNA
<213> ORGANISM: Homo sapiens

```
<400> SEQUENCE: 268
agggaacatg gccttgccca cacagatttc agacatctgg ctccagaact gtgggaggac    60
acatttctgt tgtttagaac tgcatgtttt ttatactttg ttatggctgc cctaggcaac   120
taatacagat attattttcc acttctgaac ttagcaaaat attttttaaaa tgaaaattct   180 taaatgttgg cacagt                                                   196

<210> SEQ ID NO 269
<211> LENGTH: 20
<212> TYPE: DNA
<213> ORGANISM: Homo sapiens

<400> SEQUENCE: 269
ttgcccacac agatttcaga                                                20

<210> SEQ ID NO 270
<211> LENGTH: 22
<212> TYPE: DNA
<213> ORGANISM: Homo sapiens

<400> SEQUENCE: 270
tgctaagttc agaagtggaa aa                                             22

<210> SEQ ID NO 271
<211> LENGTH: 120
<212> TYPE: DNA
<213> ORGANISM: Homo sapiens

<400> SEQUENCE: 271
ctggataaag gatgctacac gtccctggtg ggacagagca ggacggcagg ggatttcatt    60
acgccactca gaatggcagg caattgaaaa aacttataaa ttgtttatt ccagaatttt   120

<210> SEQ ID NO 272
<211> LENGTH: 20
<212> TYPE: DNA
<213> ORGANISM: Homo sapiens

<400> SEQUENCE: 272
ggataaagga tgctacacgt                                                20

<210> SEQ ID NO 273
<211> LENGTH: 20
<212> TYPE: DNA
<213> ORGANISM: Homo sapiens

<400> SEQUENCE: 273
aaaattctgg aaataaacaa                                                20

<210> SEQ ID NO 274
<211> LENGTH: 224
<212> TYPE: DNA
<213> ORGANISM: Homo sapiens

<400> SEQUENCE: 274
tgtcagtggt gtaatccgac tgtgaaagat cagtctaaca aaacagcggg gagagagagg    60
gctgaatcag agcaactagg tccaaagccg agggaaccac caacagatcc cctggtgacc   120
caacaagaaa tgctcacagt ctggacccag tcagagtctg caggacacag cagacattct   180
ggaagttaca acagccagga gcaagaggac gcatggcctg actg                    224

<210> SEQ ID NO 275
```

```
<211> LENGTH: 20
<212> TYPE: DNA
<213> ORGANISM: Homo sapiens

<400> SEQUENCE: 275
gggagagaga gggctgaatc                                                 20

<210> SEQ ID NO 276
<211> LENGTH: 21
<212> TYPE: DNA
<213> ORGANISM: Homo sapiens

<400> SEQUENCE: 276
gctcctggct gttgtaactt c                                               21

<210> SEQ ID NO 277
<211> LENGTH: 174
<212> TYPE: DNA
<213> ORGANISM: Homo sapiens

<400> SEQUENCE: 277
cgccagagca ccccttctca gaacagaaag cgtctctaca aagtgatccg gaagtgagtg     60
tgtgagggcg ctgcgtcctc cctgctcccc ttggagttgc cctttcttgc tcagatctgg   120
gtgccttggc cttgtcctgg gcccttccgc agcccccggg gtgatccccg ctag         174

<210> SEQ ID NO 278
<211> LENGTH: 19
<212> TYPE: DNA
<213> ORGANISM: Homo sapiens

<400> SEQUENCE: 278
ccagagcacc ccttctcag                                                  19

<210> SEQ ID NO 279
<211> LENGTH: 18
<212> TYPE: DNA
<213> ORGANISM: Homo sapiens

<400> SEQUENCE: 279
ggaagggccc aggacaag                                                   18

<210> SEQ ID NO 280
<211> LENGTH: 201
<212> TYPE: DNA
<213> ORGANISM: Homo sapiens

<400> SEQUENCE: 280
tatcttacgg atttgtcaac atcatttgag aagaagtcca taggctcagc agatttttat     60
gccaggtggg ccatggcata aaaatgtgaa gaatgtgctc acttagacaa tacctgtgct   120
aaaattggaa caatacagag aagattagca aattaaaaca atgttaggaa gtcagtgtgg   180
tgaggtacgg tgcctcatgc c                                             201

<210> SEQ ID NO 281
<211> LENGTH: 21
<212> TYPE: DNA
<213> ORGANISM: Homo sapiens

<400> SEQUENCE: 281
cagcagattt ttatgccagg t                                               21

<210> SEQ ID NO 282
```

```
<211> LENGTH: 20
<212> TYPE: DNA
<213> ORGANISM: Homo sapiens

<400> SEQUENCE: 282
caccgtacct caccacactg                                              20

<210> SEQ ID NO 283
<211> LENGTH: 275
<212> TYPE: DNA
<213> ORGANISM: Homo sapiens

<400> SEQUENCE: 283
aggcagggcc ctccttgcca catgtaaagc tgcacagagc ggtcactata tgtgtttcca   60
tatttgcaat ccaaccacca ccaactgagt gtgcgtcctg atcagccgag cctgcccacg  120
gtggccacag gccctctaca ttctaatctc gagagcctga gcatgtacaa attaaacgaa  180
gcaaaacgac accacccagt tctggccgta ctataggagg tttccaggaa gggtttgtga  240
acataaacat aagctaggta acactccttt ctgaa                             275

<210> SEQ ID NO 284
<211> LENGTH: 20
<212> TYPE: DNA
<213> ORGANISM: Homo sapiens

<400> SEQUENCE: 284
aaccaccacc aactgagtgt                                              20

<210> SEQ ID NO 285
<211> LENGTH: 20
<212> TYPE: DNA
<213> ORGANISM: Homo sapiens

<400> SEQUENCE: 285
cctcctatag tacggccaga                                              20

<210> SEQ ID NO 286
<211> LENGTH: 230
<212> TYPE: DNA
<213> ORGANISM: Homo sapiens

<400> SEQUENCE: 286
tcagagcatc gcctcagtgg ccatcaatag ctcgggggac tggattgctt ttggctgttc   60
aggtttgtcc ccagcctggg tggtagagat ggactcccca ttagggacca gtgctgcccg  120
gctacaggct tacttgacag ccacccactg ggggtgccct cccctccccc agttgtcttc  180
catggggtgc cctctccccc agccgccttt cagaaggggc cctcccctcc             230

<210> SEQ ID NO 287
<211> LENGTH: 20
<212> TYPE: DNA
<213> ORGANISM: Homo sapiens

<400> SEQUENCE: 287
tggattgctt ttggctgttc                                              20

<210> SEQ ID NO 288
<211> LENGTH: 20
<212> TYPE: DNA
<213> ORGANISM: Homo sapiens

<400> SEQUENCE: 288
```

```
caccccatgg aagacaactg                                              20
```

<210> SEQ ID NO 289
<211> LENGTH: 199
<212> TYPE: DNA
<213> ORGANISM: Homo sapiens

<400> SEQUENCE: 289

```
ctcatgctta catccttagc tgatcattaa actttgtgac catttcatgc tcactgcttt    60
cttgcccggg agctaatggt gaggaaaggt cactgggaac cagcgcacca acctcagaca   120
tcgattttgt tccagccttt tttcctgggc aggggtggct atcacctgct ggtaggcagc   180
ggcaggccca ctgtcctgc                                                199
```

<210> SEQ ID NO 290
<211> LENGTH: 21
<212> TYPE: DNA
<213> ORGANISM: Homo sapiens

<400> SEQUENCE: 290

```
ttaaactttg tgaccatttc a                                             21
```

<210> SEQ ID NO 291
<211> LENGTH: 18
<212> TYPE: DNA
<213> ORGANISM: Homo sapiens

<400> SEQUENCE: 291

```
taccagcagg tgatagcc                                                 18
```

<210> SEQ ID NO 292
<211> LENGTH: 181
<212> TYPE: DNA
<213> ORGANISM: Homo sapiens

<400> SEQUENCE: 292

```
tgacagaaaa gtctcagagc agtgccttct gagctcttct acaccaagca ggcagaatgt    60
tcactgctaa tgaggctgga gctggtcccc agcagtggta ggaagcttcc aacaggctca   120
ggctgtgggt gcttgcaggg gcacagtgtg acggccacgg gcctcagagc tctggtgggc   180
t                                                                   181
```

<210> SEQ ID NO 293
<211> LENGTH: 20
<212> TYPE: DNA
<213> ORGANISM: Homo sapiens

<400> SEQUENCE: 293

```
gacagaaaag tctcagagca                                              20
```

<210> SEQ ID NO 294
<211> LENGTH: 18
<212> TYPE: DNA
<213> ORGANISM: Homo sapiens

<400> SEQUENCE: 294

```
caagcaccca cagcctga                                                 18
```

<210> SEQ ID NO 295
<211> LENGTH: 187
<212> TYPE: DNA
<213> ORGANISM: Homo sapiens

```
<400> SEQUENCE: 295
acatctttct caaataaaga taacagcgat gtattttcac aaaagcaaga gcttagaaag      60
tactccaccc aggtatccct cttggaaaaa atacttaagg aaatatgaca aatggcaaag     120
tgattgttat ggatggaatg tttgtatcct cccaaaattc acatgttgag accctaattc     180
caatatg                                                              187

<210> SEQ ID NO 296
<211> LENGTH: 20
<212> TYPE: DNA
<213> ORGANISM: Homo sapiens

<400> SEQUENCE: 296
attttcacaa aagcaagagc                                                  20

<210> SEQ ID NO 297
<211> LENGTH: 20
<212> TYPE: DNA
<213> ORGANISM: Homo sapiens

<400> SEQUENCE: 297
ttgggaggat acaaacattc                                                  20

<210> SEQ ID NO 298
<211> LENGTH: 180
<212> TYPE: DNA
<213> ORGANISM: Homo sapiens

<400> SEQUENCE: 298
aggggcattc tacaaaacac ccaaccggtc aaggtcgctg aggccaagga gagattgggc      60
aaccgtcaca aaccagagaa gccgaggaga cctttcagcc aacgccatgt ggggtcctga     120
gcaggaccca ccggaagttg gtgcagctgc ctaaagaccg tcctggctga aagaaacag     180

<210> SEQ ID NO 299
<211> LENGTH: 18
<212> TYPE: DNA
<213> ORGANISM: Homo sapiens

<400> SEQUENCE: 299
aaggagagat tgggcaac                                                    18

<210> SEQ ID NO 300
<211> LENGTH: 19
<212> TYPE: DNA
<213> ORGANISM: Homo sapiens

<400> SEQUENCE: 300
gtttcttctc agccaggac                                                   19

<210> SEQ ID NO 301
<211> LENGTH: 228
<212> TYPE: DNA
<213> ORGANISM: Homo sapiens

<400> SEQUENCE: 301
tggccctgac ctgccagagc tgttggcctc cagctggcgg gtaaaaccca cggccttctc      60
agaacaggtt tctcaacaca tgagacagaa cacaccagac ttccaagggg aacacctgga     120
tggagctggt tacccagatc gttcaacacc gaggggcagc ggcttgaggg tctttccacg     180
aaggcttgga ttaacaagag gagcasrggt ctctccagga tgggccca                  228
```

```
<210> SEQ ID NO 302
<211> LENGTH: 20
<212> TYPE: DNA
<213> ORGANISM: Homo sapiens

<400> SEQUENCE: 302
catgagacag aacacaccag                                                   20

<210> SEQ ID NO 303
<211> LENGTH: 20
<212> TYPE: DNA
<213> ORGANISM: Homo sapiens

<400> SEQUENCE: 303
tcttgttaat ccaagccttc                                                   20

<210> SEQ ID NO 304
<211> LENGTH: 223
<212> TYPE: DNA
<213> ORGANISM: Homo sapiens

<400> SEQUENCE: 304
ccacccagtg tcacgtcacg gccccggcac gccatccacg gaccctggat ggagcccagc       60
tgcctccagg agcgcagttt aactacaaag gagccctggc tgcccgcccc gcccagacgc      120
actgacctgt tgttctctgt ggctgctgat ggcccatccc caaccactgg tgactcttcc      180
ctggggcccc aagctcagcc cctaaccccc tgttgctgga agt                        223

<210> SEQ ID NO 305
<211> LENGTH: 18
<212> TYPE: DNA
<213> ORGANISM: Homo sapiens

<400> SEQUENCE: 305
cacggaccct ggatggag                                                     18

<210> SEQ ID NO 306
<211> LENGTH: 18
<212> TYPE: DNA
<213> ORGANISM: Homo sapiens

<400> SEQUENCE: 306
cagggaagag tcaccagt                                                     18

<210> SEQ ID NO 307
<211> LENGTH: 186
<212> TYPE: DNA
<213> ORGANISM: Homo sapiens

<400> SEQUENCE: 307
cagaggactg ggctgcgggg tcaggaatgg gcacacttcc taactgcagg acactctaag       60
ggctttggtc atgcacacgc agccaagaga aggtgtcgct gacacacagc cttccaggag      120
cggacttgga gacctcgcca aggaccagga ctccccagca ctcacactcc cttaggcgct      180
gaagtc                                                                 186

<210> SEQ ID NO 308
<211> LENGTH: 20
<212> TYPE: DNA
<213> ORGANISM: Homo sapiens

<400> SEQUENCE: 308
```

```
actctaaggg ctttggtcat                                          20
```

<210> SEQ ID NO 309
<211> LENGTH: 20
<212> TYPE: DNA
<213> ORGANISM: Homo sapiens

<400> SEQUENCE: 309

```
ctaagggagt gtgagtgctg                                          20
```

<210> SEQ ID NO 310
<211> LENGTH: 185
<212> TYPE: DNA
<213> ORGANISM: Homo sapiens

<400> SEQUENCE: 310

```
gaagaggaca acacggggct gtctgcagag cacctgccac gcgccaggct ctgtgtccac   60
aagcacggcg gctgctccca catgacagag ctcgtgcggc agctccagga ctgtctggtg  120
ccagagcccc agctctccgc cagccccagg ccactgtgcg aggccctcag tgaagagggg  180
gccgt                                                             185
```

<210> SEQ ID NO 311
<211> LENGTH: 18
<212> TYPE: DNA
<213> ORGANISM: Homo sapiens

<400> SEQUENCE: 311

```
cgccaggctc tgtgtcca                                            18
```

<210> SEQ ID NO 312
<211> LENGTH: 18
<212> TYPE: DNA
<213> ORGANISM: Homo sapiens

<400> SEQUENCE: 312

```
ggcccctct tcactgag                                             18
```

<210> SEQ ID NO 313
<211> LENGTH: 173
<212> TYPE: DNA
<213> ORGANISM: Homo sapiens

<400> SEQUENCE: 313

```
tctaaataat gttaatgatc aaatttagtc agatctcaat cttcatatgt tagttgcctt   60
cttaataaat attctgtttt ctttatcgtt ctttatttgt atctccacct tcatttctga  120
ttaaattaag aagttttgtc tcttccattt aataattaat gtatttaata acc         173
```

<210> SEQ ID NO 314
<211> LENGTH: 22
<212> TYPE: DNA
<213> ORGANISM: Homo sapiens

<400> SEQUENCE: 314

```
tttagtcaga tctcaatctt ca                                       22
```

<210> SEQ ID NO 315
<211> LENGTH: 22
<212> TYPE: DNA
<213> ORGANISM: Homo sapiens

<400> SEQUENCE: 315

| | |
|---|---|
| aatggaagag acaaaacttc tt | 22 |

<210> SEQ ID NO 316
<211> LENGTH: 194
<212> TYPE: DNA
<213> ORGANISM: Homo sapiens

<400> SEQUENCE: 316

| | |
|---|---|
| cacactccac actggcccca cgcgggtggc gaaggactca gccagagcct ggcaggatcc | 60 |
| tggggtgtct atttccaagg aatgttctgg aagaaacata cacacatact tgtttgccag | 120 |
| atttacctgt gtggtcttcc agatgagaag cagcctgtgt cactccataa gggagagtgc | 180 |
| gtgcagcatt gaga | 194 |

<210> SEQ ID NO 317
<211> LENGTH: 18
<212> TYPE: DNA
<213> ORGANISM: Homo sapiens

<400> SEQUENCE: 317

| | |
|---|---|
| gaaggactca gccagagc | 18 |

<210> SEQ ID NO 318
<211> LENGTH: 20
<212> TYPE: DNA
<213> ORGANISM: Homo sapiens

<400> SEQUENCE: 318

| | |
|---|---|
| ctctccctta tggagtgaca | 20 |

<210> SEQ ID NO 319
<211> LENGTH: 225
<212> TYPE: DNA
<213> ORGANISM: Homo sapiens

<400> SEQUENCE: 319

| | |
|---|---|
| aagaaactcc caaggaacgc attgtcccaa gttgctgcac cagtcagtgt acattcccac | 60 |
| aaacagtgca tgagagttcc tgttgcttgt gaaataaatg gtcagcattc agtgttgtca | 120 |
| gcttttaaaa ttttctcctt tctagtgggc atgtaatggt ctcacattat agttttaatt | 180 |
| tgcattttcc tggtgacatg tgatacggaa ccttcctccc atgct | 225 |

<210> SEQ ID NO 320
<211> LENGTH: 19
<212> TYPE: DNA
<213> ORGANISM: Homo sapiens

<400> SEQUENCE: 320

| | |
|---|---|
| accagtcagt gtacattcc | 19 |

<210> SEQ ID NO 321
<211> LENGTH: 19
<212> TYPE: DNA
<213> ORGANISM: Homo sapiens

<400> SEQUENCE: 321

| | |
|---|---|
| ggaaaatgca aattaaaac | 19 |

<210> SEQ ID NO 322
<211> LENGTH: 170
<212> TYPE: DNA
<213> ORGANISM: Homo sapiens -continued

```
<400> SEQUENCE: 322
gtgcaattta attacaaacg cttaaatggg gaggtcaggg gcagagggat gatgtcacaa    60
acacacccac gtgtgcttgg tgcaaaacag taaaacaaac agcaagaagg tccatgaagg   120
aaagatcgcc tctgtcagtg ggagtaatga gagtggctga tggacaggtg              170

<210> SEQ ID NO 323
<211> LENGTH: 20
<212> TYPE: DNA
<213> ORGANISM: Homo sapiens

<400> SEQUENCE: 323
cgcttaaatg gggaggtcag                                                20

<210> SEQ ID NO 324
<211> LENGTH: 20
<212> TYPE: DNA
<213> ORGANISM: Homo sapiens

<400> SEQUENCE: 324
cctgtccatc agccactctc                                                20

<210> SEQ ID NO 325
<211> LENGTH: 189
<212> TYPE: DNA
<213> ORGANISM: Homo sapiens

<400> SEQUENCE: 325
acgccaagca ggagatgcca gacacagagt ccatcctgag agagtctgtt cctgtccaag    60
ctcagaaaca caggaagcca cctgtgctgt agcagcacac ggagatgcat cctttctggt   120
ccaccccacg gccctcattg cagtcaggga tcctctccca gaaagtccct gctgccagcc   180
cctgcccctt                                                          189

<210> SEQ ID NO 326
<211> LENGTH: 20
<212> TYPE: DNA
<213> ORGANISM: Homo sapiens

<400> SEQUENCE: 326
agcaggagat gccagacaca                                                20

<210> SEQ ID NO 327
<211> LENGTH: 20
<212> TYPE: DNA
<213> ORGANISM: Homo sapiens

<400> SEQUENCE: 327
ggtggaccag aaaggatgca                                                20

<210> SEQ ID NO 328
<211> LENGTH: 170
<212> TYPE: DNA
<213> ORGANISM: Homo sapiens

<400> SEQUENCE: 328
catgagaaag actttgttcc catgagaaca acaagagaaa ctcaaacaaa attaaaattg    60
tacttttcta aaagaccggg gtggggggtcg tggtcaggca gcagcatgaa gaaagccttg   120
agaactgaat tccagaaaga aacaagcata ggcaagaaag agagatgaca                170

<210> SEQ ID NO 329
```

```
<211> LENGTH: 22
<212> TYPE: DNA
<213> ORGANISM: Homo sapiens

<400> SEQUENCE: 329
cccatgagaa caacaagaga aa                                              22

<210> SEQ ID NO 330
<211> LENGTH: 20
<212> TYPE: DNA
<213> ORGANISM: Homo sapiens

<400> SEQUENCE: 330
ctctttcttg cctatgcttg                                                 20

<210> SEQ ID NO 331
<211> LENGTH: 167
<212> TYPE: DNA
<213> ORGANISM: Homo sapiens

<400> SEQUENCE: 331
aagatttaga acagctgaag cagcgagaaa aaacccagca tgagtcagaa ctggagcaac     60
tgaggattta ttttgaaaag aagttaaggg atgctgagaa aacttaccaa gaagacctaa   120
ccctgttaca gcagaggctg caggggcga gggaagatgc tcttctg                   167

<210> SEQ ID NO 332
<211> LENGTH: 21
<212> TYPE: DNA
<213> ORGANISM: Homo sapiens

<400> SEQUENCE: 332
cagctgaagc agcgagaaaa a                                               21

<210> SEQ ID NO 333
<211> LENGTH: 19
<212> TYPE: DNA
<213> ORGANISM: Homo sapiens

<400> SEQUENCE: 333
cccctgcagc tctgctgt                                                   19

<210> SEQ ID NO 334
<211> LENGTH: 174
<212> TYPE: DNA
<213> ORGANISM: Homo sapiens

<400> SEQUENCE: 334
gggaaactga cttggctttt gcaagggtca ttgcttcctg atgcatgttt aactgtcctg     60
tgttcacttt gttgccgcag gtttttagag gaacgtaaag agatcaccga gaaattcagt   120
gcggaacaag atgccttcct gcaggaggcc caggagcagc atgcccgtga gctg          174

<210> SEQ ID NO 335
<211> LENGTH: 22
<212> TYPE: DNA
<213> ORGANISM: Homo sapiens

<400> SEQUENCE: 335
gggaaactga cttggctttt gc                                              22

<210> SEQ ID NO 336
<211> LENGTH: 20
<212> TYPE: DNA
```

```
<213> ORGANISM: Homo sapiens

<400> SEQUENCE: 336
ggcatcttgt tccgcactga                                               20

<210> SEQ ID NO 337
<211> LENGTH: 175
<212> TYPE: DNA
<213> ORGANISM: Homo sapiens

<400> SEQUENCE: 337
ccctgcacac tgacctgcat gccctcgtca cctgcactct gcatgctcac catctgacgg   60
actcctgcga cgggcatggg aaggtcgccg ccgccggcag ccttgcgagc actttggatg  120
tgtgcacccg gcatgccagg cccgagtcaa cagactggcc gaccttggcg tcctg       175

<210> SEQ ID NO 338
<211> LENGTH: 20
<212> TYPE: DNA
<213> ORGANISM: Homo sapiens

<400> SEQUENCE: 338
gccctcgtca cctgcactct                                               20

<210> SEQ ID NO 339
<211> LENGTH: 20
<212> TYPE: DNA
<213> ORGANISM: Homo sapiens

<400> SEQUENCE: 339
ccaaggtcgg ccagtctgtt                                               20

<210> SEQ ID NO 340
<211> LENGTH: 155
<212> TYPE: DNA
<213> ORGANISM: Homo sapiens

<400> SEQUENCE: 340
tttattgctg agtggtattc cattttatgg gtccattata gtttatttgt ccagacactt   60
catggaaaga catcagtgtt tcctgttttt caatcataaa ttgatgttta attttaaaat  120
tttggaattg tagaagaaat gcaattcttt tttcc                              155

<210> SEQ ID NO 341
<211> LENGTH: 22
<212> TYPE: DNA
<213> ORGANISM: Homo sapiens

<400> SEQUENCE: 341
tgggtccatt atagtttatt tg                                            22

<210> SEQ ID NO 342
<211> LENGTH: 22
<212> TYPE: DNA
<213> ORGANISM: Homo sapiens

<400> SEQUENCE: 342
tgcatttctt ctacaattcc aa                                            22

<210> SEQ ID NO 343
<211> LENGTH: 208
<212> TYPE: DNA
<213> ORGANISM: Homo sapiens
```

-continued

<400> SEQUENCE: 343

```
ctttggtgca gaatcatgct gcaggcaagg tgggcccacc tccctggaat ttcatccccc    60
ccgtcagtta aacccatggt ggttttattt tctaggccac ctgatctggg aggaccacct   120
ccaagaaaag cagtcctatc gatgaacggt ctaagttatg gtgttatcag agtggatact   180
gaagaaaagt tgtcagtcct tactgttc                                      208
```

<210> SEQ ID NO 344
<211> LENGTH: 20
<212> TYPE: DNA
<213> ORGANISM: Homo sapiens

<400> SEQUENCE: 344

```
ggcccacctc cctggaattt                                                20
```

<210> SEQ ID NO 345
<211> LENGTH: 22
<212> TYPE: DNA
<213> ORGANISM: Homo sapiens

<400> SEQUENCE: 345

```
tccactctga taacaccata ac                                             22
```

<210> SEQ ID NO 346
<211> LENGTH: 232
<212> TYPE: DNA
<213> ORGANISM: Homo sapiens

<400> SEQUENCE: 346

```
atcacctggt ttggtgcatc ctcgcagaaa gagagccata cagtgaagtg gaaacacacc    60
caaaagctct gcaatattcc tagaagttct cgaatctcct ccttaacaga gctgcagaag   120
ggaaacacag acaggaagca cctgtttgac tcagacagca gccctaatgc agtgccactc   180
aggagcattc cctcatttga agaccccca attacatgaa attatcaacc cc            232
```

<210> SEQ ID NO 347
<211> LENGTH: 20
<212> TYPE: DNA
<213> ORGANISM: Homo sapiens

<400> SEQUENCE: 347

```
acacccaaaa gctctgcaat                                                20
```

<210> SEQ ID NO 348
<211> LENGTH: 20
<212> TYPE: DNA
<213> ORGANISM: Homo sapiens

<400> SEQUENCE: 348

```
caaatgaggg aatgctcctg                                                20
```

<210> SEQ ID NO 349
<211> LENGTH: 240
<212> TYPE: DNA
<213> ORGANISM: Homo sapiens

<400> SEQUENCE: 349

```
ggaactgcag gagatccctg ctgccttcca gttcatggga tgatggcctc cacttctgcc    60
cctgtttgct tctcctttca aatcttacat gaaggtatac agtttgaaga agccagtttg   120
```

```
actccaatat ctgtgcaatg gaatactgct cattaaaaag gaattaaact attgatacac    180
acaacatggg tgaagatcaa actgtctcct tcccttttgat tcaagggaat ctgagaaatg   240
```

<210> SEQ ID NO 350
<211> LENGTH: 19
<212> TYPE: DNA
<213> ORGANISM: Homo sapiens

<400> SEQUENCE: 350

```
acttctgccc ctgtttgct                                                  19
```

<210> SEQ ID NO 351
<211> LENGTH: 21
<212> TYPE: DNA
<213> ORGANISM: Homo sapiens

<400> SEQUENCE: 351

```
tgatcttcac ccatgttgtg t                                               21
```

<210> SEQ ID NO 352
<211> LENGTH: 187
<212> TYPE: DNA
<213> ORGANISM: Homo sapiens

<400> SEQUENCE: 352

```
tggagaaagt tgttgcaaac tgcccagaga ccctgggagt cactccagtt ttctgaaacc    60
cagatatttc agtgcctcag gagagacaag tcctgacctt ctctcctcca gctctcccag   120
gagataggca agcccctaac tccctaacta agcccttcag acctgaaatc cattgagtgg   180
cttctttt                                                             187
```

<210> SEQ ID NO 353
<211> LENGTH: 18
<212> TYPE: DNA
<213> ORGANISM: Homo sapiens

<400> SEQUENCE: 353

```
gcaaactgcc cagagacc                                                   18
```

<210> SEQ ID NO 354
<211> LENGTH: 20
<212> TYPE: DNA
<213> ORGANISM: Homo sapiens

<400> SEQUENCE: 354

```
ttagggagtt aggggcttgc                                                 20
```

<210> SEQ ID NO 355
<211> LENGTH: 184
<212> TYPE: DNA
<213> ORGANISM: Homo sapiens

<400> SEQUENCE: 355

```
agggccatgg gatgatgcag gtggagactg gagtgctaca gctgcaagca aatacatttc    60
tgtgctgtga agccacccat ttggtggtac tacgttaaaa cagctctagg aaattaatac   120
agatgttgcc tgtattttttg tttctcatat tactactcat tgttttaatg atgactgttt   180
tatt                                                                 184
```

-continued

```
<210> SEQ ID NO 356
<211> LENGTH: 20
<212> TYPE: DNA
<213> ORGANISM: Homo sapiens

<400> SEQUENCE: 356
aggtggagac tggagtgcta                                              20

<210> SEQ ID NO 357
<211> LENGTH: 22
<212> TYPE: DNA
<213> ORGANISM: Homo sapiens

<400> SEQUENCE: 357
agaaacaaaa atacaggcaa ca                                           22
```